United States Patent
Hoshino et al.

(10) Patent No.: US 12,344,864 B2
(45) Date of Patent: Jul. 1, 2025

(54) ARTIFICIALLY SYNTHESIZED mRNA AND USE OF SAME

(71) Applicant: PUBLIC UNIVERSITY CORPORATION NAGOYA CITY UNIVERSITY, Nagoya (JP)

(72) Inventors: Shinichi Hoshino, Nagoya (JP); Nao Hosoda, Nagoya (JP)

(73) Assignee: PUBLIC UNIVERSITY CORPORATION NAGOYA CITY UNIVERSITY, Nagoya (JP)

(*) Notice: Subject to any disclaimer, the term of this patent is extended or adjusted under 35 U.S.C. 154(b) by 156 days.

(21) Appl. No.: 17/769,655

(22) PCT Filed: Oct. 16, 2020

(86) PCT No.: PCT/JP2020/039160
§ 371 (c)(1),
(2) Date: Apr. 15, 2022

(87) PCT Pub. No.: WO2021/075567
PCT Pub. Date: Apr. 22, 2021

(65) Prior Publication Data
US 2024/0026311 A1 Jan. 25, 2024

(30) Foreign Application Priority Data
Oct. 17, 2019 (JP) .................. 2019-189929

(51) Int. Cl.
C12N 9/02 (2006.01)
C07K 14/47 (2006.01)
C12N 9/04 (2006.01)

(52) U.S. Cl.
CPC ............ C12N 9/0008 (2013.01); C07K 14/47 (2013.01); C07K 14/4717 (2013.01); C12N 9/0006 (2013.01); C12Y 101/01027 (2013.01); C12Y 102/01012 (2013.01)

(58) Field of Classification Search
CPC ................ C12N 9/0008; C12N 9/0006; C12N 101/01027; C12N 102/01012; C12N 15/67; C12N 15/85; C12N 15/11; C12N 15/63; C07K 14/47; C07K 14/4717; C12Y 102/01; C12Y 102/01009
See application file for complete search history.

(56) References Cited

U.S. PATENT DOCUMENTS

| | | | | |
|---|---|---|---|---|
| 9,822,378 B2* | 11/2017 | Kruse | ............... | C12Q 1/6865 |
| 11,015,204 B2* | 5/2021 | Limphong | ........... | C07K 14/472 |
| 2009/0181427 A1 | 7/2009 | Abu Khabar | | |
| 2015/0218554 A1 | 8/2015 | Thess | | |
| 2017/0233761 A1 | 8/2017 | Ding | | |
| 2018/0353618 A1 | 12/2018 | Burkhardt et al. | | |
| 2019/0345504 A1* | 11/2019 | Grund | ............... | A61P 3/02 |
| 2020/0024365 A1 | 1/2020 | Xie et al. | | |

FOREIGN PATENT DOCUMENTS

| | | |
|---|---|---|
| CN | 104284979 A | 1/2015 |
| CN | 106929513 A | 7/2017 |
| CN | 109104870 A | 12/2018 |
| JP | 2012-100593 A | 5/2012 |
| JP | 2015-221026 A | 12/2015 |
| JP | 2015-226531 A | 12/2015 |
| JP | 2018-74954 A | 5/2018 |
| WO | WO 2013/143700 A2 | 10/2013 |
| WO | WO 2014/186334 A1 | 11/2014 |
| WO | WO 2018/089846 A1 | 5/2018 |

OTHER PUBLICATIONS

Aytekin et al., Regulation of the expression of the oncogene EVI1 through the use of alternative mRNA 5V-ends. Gene, 2005, vol. 356: 160-168. (Year: 2005).*
Ellis CJ., Expression Of p21 C,P/WAF1 Transcript Variants Upon DNA Damage. M.Sc., Thesis, 2007, pp. 1-120, Dalhousie Univ., Canada, pp. 1-120 (Year: 2007).*
Lai et al., mRNAs and lncRNAs intrinsically form secondary structures with short end-to-end distances. Nature, 2018, vol. 9:4328, pp. 1-11. (Year: 2018).*
Lai et al., Supplementary Information For mRNAs and lncRNAs intrinsically form secondary structures with short end-to-end distances Nature, 2018, vol. 9:4328, pp. 119. (Year: 2018).*
Muhlrad et al., Deadenylation of the unstable mRNA encoded by the yeast MFA2 gene leads to decapping followed by 5-3' digestion of the transcript. Genes & Development., 1994, vol. 8: 855-856. (Year: 1994).*
Stoecklin et al., Functional Hierarchy of AUUUA Motifs in Mediating Rapid Interleukin-3 mRNA Decay*. The J. Biol. Chem., 1994, vol. 269(46): 28591-28597. (Year: 1994).*
Wilson et al., Removal of poly(A) and consequent degradation of c-fos mRNA facilitated by 3' AU-rich sequences. Nature, 1988, vol. 336(24): 396-399 (Year: 1998).*
Chinese Office Action and Search Report for Chinese Application No. 202080072851.0, dated Aug. 23, 2023, with an English translation.
Malhotra et al., "*Homo sapiens* glyceraldehyde-3-phosphate dehydrogenase (GAPDH), transcript variant 7, mRNA," GenBank [online], Accession No. NM_001357943.2, 2019, 4 pages total.
Adibzadeh et al., "Enhancing Stability of Destabilized Green Fluorescent Protein Using Chimeric mRNA Containing Human Beta-Globin 5' and 3' Untranslated Regions," Avicenna Journal of Medical Biotechnology, vol. 11, No. 1, 2019, pp. 112-117.

(Continued)

*Primary Examiner* — Ganapathirama Raghu
(74) *Attorney, Agent, or Firm* — Birch, Stewart, Kolasch & Birch, LLP

(57) ABSTRACT

Provided is a technique for improving the translation efficiency of mRNA. The mRNA includes: a 5' untranslated region of an mRNA encoding a protein; and a 3' untranslated region having 40% or more and 80% or less complementarity to 5' untranslated region.

11 Claims, 28 Drawing Sheets

Specification includes a Sequence Listing.

(56) References Cited

OTHER PUBLICATIONS

Elfakess et al., "A Translation Initiation Element Specific to mRNAs with Very Short 5'UTR that Also Regulates Transcription," PLOS One, vol. 3, Issue 8, e3094, 2008, pp. 1-12.
Elfakess et al., "Unique translation initiation of mRNAs-containing TISU element," Nucleic Acids Research, vol. 39, No. 17, 2011, pp. 7598-7609.
Ruiz De Los Mozos et al., "Base Pairing Interaction between 5'- and 3'-UTRs Controls icaR mRNA Translation in *Staphylococcus aureus*," PLOS Genetics, vol. 9, Issue 12, e1004001, 2013, pp. 1-18.
Supplementary Partial European Search Report for European Application No. 20877848, dated Aug. 24, 2023.
*Homo sapiens* glyceraldehyde-3-phosphate dehydrogenase (GAPDH), transcript variant 1, mRNA (Retrieved from GenBank [online] Accession No. NM_002046.7), Retrieved on Dec. 4, 2020, <URL: https://www.ncbi.nlm.nih.gov/nuccore/1519316078?sat=47&satkey=122936675>, total 8 pages.
International Search Report for PCT/JP2020/039160 mailed on Dec. 15, 2020.
Mehta et al., "Derepression of the Her-2 uORF is mediated by a novel post-transcriptional control mechanism in cancer cells", Genes & Development, 2006, vol. 20, pp. 939-953.
Ricci et al., "miRNA repression of translation in vitro takes place during 43S ribosomal scanning", Nucleic Acids Research, 2013, vol. 41, No. 1, pp. 586-598.
Written Opinion of the International Searching Authority for PCT/JP2020/039160 mailed on Dec. 15, 2020.

\* cited by examiner

Fig.17

Fig.19 cap — GCUCUGCUCCUCCUGUUCGACAGUCAGCCGCAUCUUCUUUUGCGUCGCCAGCCGACCAU  
AAAAA --- CGAGACGAGGAGGACAAGCUGUCAGUCGGCGUAGAAGAAAACGCAGCGGUCGGCUGGUA

SEQ ID NO: 27
SEQ ID NO: 33

EGFP ORF

ARTIFICIALLY SYNTHESIZED mRNA AND USE OF SAME

TECHNICAL FIELD

The present invention relates to an artificially synthesized mRNA and use of the same. The present application claims priority based on Japanese Patent Application No. 2019-189929 filed on Oct. 17, 2019, the contents of which are incorporated herein by reference in its entirety.

REFERENCE TO SEQUENCE LISTING

This application includes an electronically submitted sequence listing in .txt format. The .txt file contains a sequence listing entitled "7144-0106PUS1_ST25.txt" created on Dec. 13, 2024 and is 45,835 bytes in size. The sequence listing contained in this .txt file is part of the specification and is hereby incorporated by reference herein in its entirety.

BACKGROUND ART

Gene therapies have been performed so far using DNA such as a virus as a vector, but the risk of carcinogenesis or the like caused by incorporation thereof into a genome remains as a major problem. On the other hand, mRNA has attracted attention as a safe nucleic acid medicine having no risk caused, for example, by insertion thereof into a genome, unlike DNA, but instability and low translation efficiency inherent in RNA are pointed out as disadvantages (for example, PTL 1 to PTL 3).

PTL 1 discloses a method in which a function suppressive substance against 2'-5'-oligoadenylate synthase is used for mRNA of a gene of interest, as a technique for suppressing the generation of an intracellular degradation mechanism of mRNA, through elucidation of this mechanism.

CITATION LIST

Patent Literature

[PTL 1] JP 2018-74954 A
[PTL 2] JP 2015-221026 A
[PTL 3] JP 2015-226531 A

SUMMARY OF INVENTION

Technical Problem

Indeed, the technique described in PTL 1 improves instability inherent in RNA. However, there is room for improvement in improving the translation efficiency of mRNA.

Hence, through diligent research, the present inventors have invented a method for improving the translation efficiency of mRNA.

Solution to Problem

The present invention has been made to solve the problem, and can be realized as the following forms.

(1) According to one embodiment of the present invention, an artificially synthesized mRNA is provided. This artificially synthesized mRNA includes: a 5' untranslated region of an mRNA encoding a protein; and a 3' untranslated region having 40% or more and 80% or less complementarity to the 5' untranslated region.

(2) In the artificially synthesized mRNA described above, the protein may be selected from the group consisting of glyceraldehyde-3-phosphate dehydrogenase, ß-globin, RPS8, and LDHB.

(3) In the artificially synthesized mRNA described above, the 3' untranslated region may have 50% or more and 75% or less complementarity to the 5' untranslated region.

(4) According to other embodiment of the present invention, provided is a method including the step of introducing the artificially synthesized mRNA described above into a cell.

(5) According to other embodiment of the present invention, provided is a cell including the artificially synthesized mRNA described above introduced thereinto.

(6) According to other embodiment of the present invention, a method for manufacturing an artificially synthesized mRNA is provided. This method for manufacturing an artificially synthesized mRNA includes the step of preparing an artificially synthesized mRNA which includes: a 5' untranslated region of an mRNA encoding a protein; and a 3' untranslated region having 40% or more and 80% or less complementarity to the 5' untranslated region.

(7) According to other embodiment of the present invention, an artificially synthesized mRNA is provided. This artificially synthesized mRNA includes: a 5' untranslated region of an mRNA encoding glyceraldehyde-3-phosphate dehydrogenase; and a 3' untranslated region of the mRNA encoding glyceraldehyde-3-phosphate dehydrogenase.

(8) According to other embodiment of the present invention, a method for manufacturing an artificially synthesized mRNA is provided. This method for manufacturing an artificially synthesized mRNA includes the step of preparing an mRNA which includes: a 5' untranslated region of an mRNA encoding glyceraldehyde-3-phosphate dehydrogenase; and a 3' untranslated region of the mRNA encoding glyceraldehyde-3-phosphate dehydrogenase.

(9) According to other embodiment of the present invention, provided is a method including the step of introducing the artificially synthesized mRNA of (7) above into a cell.

(10) According to other embodiment of the present invention, provided is a cell including the artificially synthesized mRNA of (7) above introduced thereinto.

BRIEF DESCRIPTION OF DRAWINGS

FIG. 17 (SEQ ID NOS: 27 and 34-38) A view illustrating artificially synthesized mRNAs produced.

FIG. 19 (SEQ ID NOS: 27 and 33) A view illustrating an artificially synthesized mRNA produced.

DESCRIPTION OF EMBODIMENTS

Figure 1:
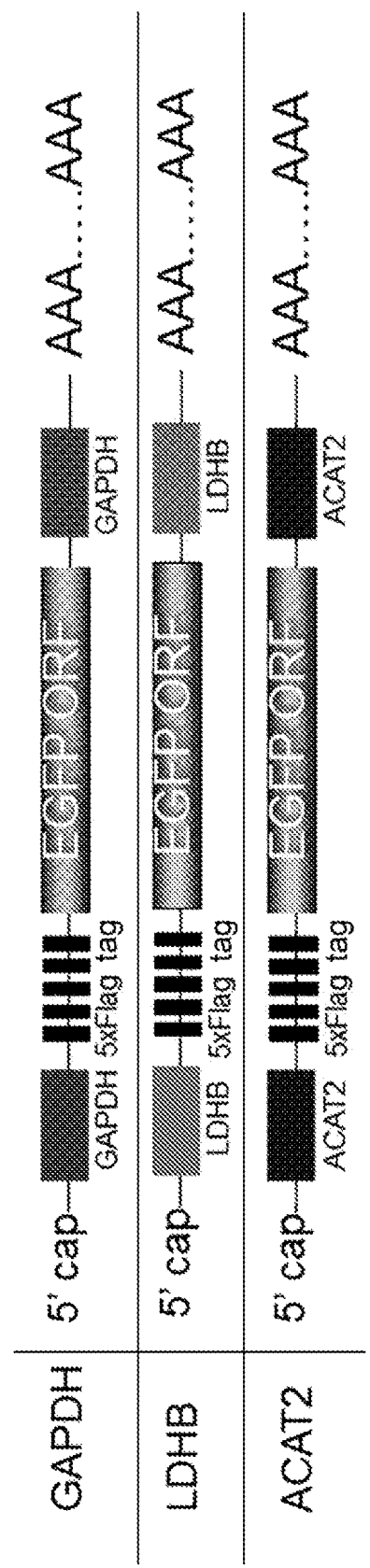
FIG. 1 A view illustrating artificially synthesized mRNAs produced.

The disclosure of the present specification relates to an artificially synthesized mRNA having a high translation efficiency and use of the same. In addition, the mRNA of the present invention is sometimes referred to as "artificially synthesized mRNA" for the purpose of representing the characteristic of being prepared by artificial manipulation and distinguishing it from intracellular (endogenous) mRNA. Here, in the present specification, the "mRNA" refers to an RNA having base sequence information and a structure that can be translated into a protein. The two terms "suppression" and "inhibition" overlap in meaning, and are often used interchangeably. The term "suppression" is used consistently throughout the present specification, unless it is particularly necessary to distinguish between these two terms from the context. The "high translation efficiency" means an increase in amount of mRNA to be translated.

1. mRNA

The mRNA of the present invention includes a coding region of a gene of interest (a region encoding a protein that is an expression product of the gene of interest). The "gene of interest" is a gene to be expressed in a cell using the mRNA of the present invention. Various genes can be adopted as the gene of interest. A cell expressing the gene of interest by introducing the mRNA of the present invention is also referred to as "target cell" in the present specification. Examples of the gene of interest include genes such as enzymes (e.g. nucleases (ZFN (Zinc Finger Nuclease), TALEN (Transcription Activator-Like Effector Nuclease), and CRISPR-Cas9), cytokines, hormones, and neurotransmitters; genes that cause a disease due to deterioration in function (for example, due to mutation), deficiency, or the like thereof; genes that normally function but whose expression is desired to be enhanced; genes that are not originally possessed by the target cell and, when expressed, are useful for survival, maintenance, and the like of the target cell; genes encoding proteins that act on the target cell and enhance the function originally possessed by the target cell or proteins that exert a function different from the function originally possessed by the target cell; and genes encoding proteins that do not act on the target cell and are secreted from the target cell and act on surrounding cells (e.g. proteins involved in intercellular networks). A gene encoding a protein that does not substantially act on the target cell or surrounding cells can also serve as the gene of interest. Examples of such a gene include genes encoding proteins or the like used in medicinal products or the like (such as human erythropoietin gene, human fibrinogen gene, human serum albumin gene, human lactoferrin gene, and human α-glucosidase gene). Such a gene can be used to produce a recombinant protein that can be used as a medicinal product or the like, in the target cell.

The target cell is not particularly limited, and, for example, various eukaryotic cells can be used as the target cell. More specifically, examples of cells that can be used as the target cell include various cells of mammals (human, monkey, cow, horse, rabbit, mouse, rat, guinea pig, hamster, and the like) such as cardiomyocytes, smooth muscle cells, adipocytes, fibroblasts, osteocytes, chondrocytes, osteoclasts, parenchymal cells, epidermal keratinocytes, epithelial cells (skin epithelial cells, corneal epithelial cells, conjunctival epithelial cells, oral mucosal epithelia, hair follicle epithelial cells, oral mucosal epithelial cells, airway mucosal epithelial cells, intestinal mucosal epithelial cells, and the like), endothelial cells (corneal endothelial cells, vascular endothelial cells, and the like), neurons, glial cells, splenocytes, pancreatic ß cells, mesangial cells, Langerhans cells, hepatocytes, progenitor cells or stem cells thereof, or induced pluripotent stem cells (iPS cells), mesenchymal stem cells (MSCs), embryonic stem cells (ES cells), embryonic germ cells (EG cells), and embryonic tumor cells (EC cells). In addition, as the target cell, for example, passaged cells, cells induced to differentiate into a specific cell lineage, established cells (for example, HeLa cells, CHO cells, Vero cells, HEK 293 cells, HepG2 cells, COS-7 cells, NIH3T3 cells, and Sf9 cells), and the like can be used.

The mRNA of the present invention may be introduced into the target cell in a state of being separated from a living body (that is, the isolated target cell) or the target cell in a state of constituting a living body. Therefore, the present invention can be carried out under all environments of in vitro, in vivo, and ex vivo. Here, the "isolated" indicates a state in which the target cell is in a state of being taken out from its original environment (for example, a state of constituting a living body). Therefore, usually, the isolated target cell is present in a culture vessel or a storage vessel, and can be artificially manipulated in vitro. Specifically, a cell (including an established cell) that has been separated from a living body and is in a state of being cultured in vitro has eligibility as the isolated target cell. As long as the target cell is in an isolated state in the above meaning, it is an isolated cell even in a state of forming an organism.

The isolated target cell can be prepared from a living body (for example, a patient). On the other hand, cells obtained from Riken BioResource Center, National Institute of Technology and Evaluation, ATCC (American Type Culture Collection), DSMZ (German Collection of Microorganisms and Cell Cultures), or the like may be used as the isolated target cell.

The mRNA of the present invention includes a 5' untranslated region (5' UTR) and a 3' untranslated region (3' UTR).

An mRNA of an embodiment of the present invention includes a 5' UTR of an mRNA encoding a protein and a 3' UTR having 40% or more and 80% or less complementarity to the 5' UTR. In other words, the mRNA of the embodiment of the present invention includes a translated region encoding a protein of interest, a 5'UTR of an mRNA encoding a protein different from the protein of interest, and a 3' UTR having 40% or more and 80% or less complementarity to the 5' UTR. According to this form, the translation efficiency can be improved. From the viewpoint of further improving the translation efficiency, the complementarity of the 3' UTR to the 5' UTR is preferably 50% or more and 75% or less. The translation efficiency can be improved, so that the expression efficiency of the protein of interest can be improved.

The 5' UTR of an mRNA encoding a protein is not particularly limited, and is, for example, preferably a 5' UTR of an mRNA encoding a protein having a protein expression level of 106 molecules or more per cell (for example, HeLa cell). This protein is more preferably a protein selected from the group consisting of glyceraldehyde-3-phosphate dehydrogenase, B-globin, RPS8, and LDHB.

Further, an mRNA of another embodiment of the present invention includes a 5' UTR of an mRNA encoding glyceraldehyde-3-phosphate dehydrogenase (GAPDH) and a 3' UTR of the mRNA encoding GAPDH. In other words, the mRNA of the embodiment of the present invention includes a 5' UTR of an mRNA encoding GAPDH, a 3' UTR of the mRNA encoding GAPDH, and an ORF (Open Reading Frame) encoding a protein that is not GAPDH. According to this form, the translation efficiency can be improved. In the present specification, the "UTR of an mRNA encoding . . . " is also simply referred to as "UTR of . . . ". For example, the "5' UTR of an mRNA encoding GAPDH" is also referred to as "UTR of GAPDH".

In the present specification, as the UTR of GAPDH, the UTR of human-derived GAPDH is used, but the present invention is not limited thereto. As the UTR of GAPDH, for example, a UTR of GAPDH derived from another organism (for example, mice) may be used. In addition, a length of the UTR of GAPDH included in the mRNA of the present invention is preferably 70% or more and 130% or less, more preferably 80% or more and 120% or less, and still more preferably 90% or more and 110% or less of the UTR of organism-derived GAPDH. In addition, a matching rate of the UTR of GAPDH included in the mRNA of the present invention with the UTR of organism-derived GAPDH is preferably 70% or more, more preferably 80% or more, and still more preferably 90% or more.

An mRNA of another embodiment of the present invention includes a 5' UTR of an mRNA encoding GAPDH and a 3' UTR having 40% or more and 80% or less complementarity to the 5' UTR. In other words, the mRNA of the embodiment of the present invention includes a 5' UTR of an mRNA encoding GAPDH, a 3' UTR having 40% or more and 80% or less complementarity to the 5' UTR, and an ORF encoding a protein that is not GAPDH. According to this form, the translation efficiency can be improved. From the viewpoint of further improving the translation efficiency, the complementarity of the 3' UTR to the 5' UTR is preferably 50% or more and 75% or less.

The mRNA of the present embodiment may have a 5' cap structure (structure in which $m^7G$ (7-methylguanosine) binds to the 5' end nucleoside via a 5'-5' triphosphate bridge) and a poly (A) tail necessary for translation thereof. A length of the poly (A) tail is not particularly limited, and is, for example, 30 to 200 bases. A translation initiation factor eIF4E binds to the 5' cap structure, and a poly (A)-binding protein PABP binds to the poly (A) tail, so that they form a complex via a translation initiation factor eIF4G which is a scaffold protein, whereby the mRNA forms a cyclic structure (Wells S E, et al. Mol Cell. 1998; 2:135-140). Furthermore, a translation termination factor eRF3 loops out the 3' UTR by forming a complex with PABP-eIF4G (Uchida N, et al. J Biol Chem. 2002; 277:50286-50292). Such circularization of mRNA greatly contributes to the efficiency of translation initiation by physically bringing the translation termination site and the translation initiation site close to each other and recycling a ribosome that has terminated translation from a termination codon to next translation initiation not through the 3' UTR. The 5' end cap structure and the poly (A) tail stabilize mRNA by not only such an improvement in translation efficiency but also inhibiting mRNA degradation from the terminal by exonuclease, and greatly contribute to gene expression regulation after transcription in both processes of translation efficiency improvement and mRNA stabilization.

The mRNA of the present invention can be prepared, for example, by a method such as an in vitro transcription system or chemical synthesis. By using a kit for in vitro transcription (for example, RiboMAXsystem provided by Promega Corporation, CUGA7 in vitro transcription kit provided by NIPPON GENE CO., LTD., or MEGAscript T7 kit provided by Life Technologies Corporation), it is possible to easily prepare an mRNA of interest. The addition of the 5' cap structure can also be performed by a known method, and, for example, 3'-O-Me-m7G(5')ppp(5')G RNA Cap Structure Analog provided by New England Biolabs can be used.

As the mRNA of the present invention, two or more mRNAs may be used in combination. For example, an mRNA having a coding region of a specific gene and an mRNA having a region encoding an expression product that interacts with an expression product of the gene can be used in combination.

An amount of the mRNA of the present invention may be set so that a sufficient amount of expression product can be obtained in the target cell in consideration of the purpose of use, the characteristics of the gene of interest to be used, the type of target cell, and the like. As an example of the amount of the mRNA, 0.5 to 1.0 μg of the mRNA may be contained per 3-cm culture dish as a single batch.

For example, exonuclease inhibitors, endonuclease inhibitors, phospholipids, calcium phosphate, polyethyleneimine, polyethylene glycol-polycations which are nanomicelle forming agents, buffers, inorganic salts, divalent ions and the like may be used for the purpose of protecting the artificially synthesized mRNA; antibiotics and the like may be used for the purpose of preventing contamination of bacteria; and animal serum, growth factors, sugars, vitamins, divalent ions and the like may be used for the purpose of enhancing the proliferation capability of cells. In addition, other pharmaceutically acceptable components (for example, carriers, excipients, disintegrants, buffers, emulsifiers, suspension agents, soothing agents, stabilizers, preservatives, antiseptics, physiological saline, etc.) can be used. Furthermore, for the purpose of enhancing an efficiency of introducing an active ingredient into cells, a special synthetic medium such as Opti-MEM provided by Life Technologies Corporation may be used.

2. Introduction Method

In order to express the gene of interest in the target cell using the present invention, a step of introducing the mRNA of the gene of interest into the target cell is performed.

The introduction of the mRNA into the target cell can be performed by a known method. For example, the introduction can be performed by a calcium phosphate co-precipitation method, electroporation (Potter, H. et al., Proc. Natl. Acad. Sci. U.S.A. 81, 7161-7165(1984)), lipofection (Felgner, P. L. et al., Proc. Natl. Acad. Sci. U.S.A. 84, 7413-7417(1987)), microinjection (Graessmann, M. & Graessmann, A., Proc. Natl. Acad. Sci. U.S.A. 73, 366-370(1976)), a method of Hanahan (Hanahan, D., J. Mol. Biol. 166, 557-580(1983)), a lithium acetate method (Schiestl, R. H. et al., Curr. Genet. 16, 339-346(1989)), a protoplast-polyethylene glycol method (Yelton, M. M. et al., Proc. Natl. Acad. Sci. 81, 1470-1474(1984)), an ultrasonic gene introduction method, a method using a cationic polyamine acid (see, for example, JP 2011-173802 A), a method using a polyion complex (PIC) type polymer micelle including a block copolymer having a cationic polymer segment and a non-crosslinked hydrophilic polymer segment (for example, see JP 2004-352972 A and WO 2012/005376 A), or the like.

3. Application

According to the mRNA of the present invention, the translation efficiency is improved in the target cell, and thus the protein of interest is highly expressed. Therefore, the present invention can be applied to various applications in which high expression of the protein of interest is desired. Examples of the application of the present invention include (A) treatment of various viral diseases (e.g. hepatitis B, acquired immunodeficiency syndrome AIDS, and adult T-cell leukemia) and genetic diseases (e.g. Duchenne muscular dystrophy, cystic fibrosis, beta-thalassemia, Hurler syndrome, retinitis pigmentosa, and X-linked nephrogenic diabetes insipidus), (B) cancer immunotherapy, (C) production of iPS cells, and (D) induction of differentiation of stem cells (for example, multipotent stem cells such as iPS cells and ES cells) or progenitor cells.

The above applications (A) and (B) utilize the present invention as a so-called RNA medicine. In the treatment of hepatitis B as a specific example of the application (A), for example, an mRNA in which a nuclease (ZFN, TALEN, or CRISPR-Cas9) gene that cleaves and degrades a viral DNA incorporated in a genome is incorporated as a gene of interest is used, thereby making it possible to perform viral treatment without a risk of carcinogenesis that is a problem in a conventional method using a viral vector. Thus, the present invention is also useful as a virus-removing agent. In the treatment of genetic diseases, the present invention is applied, for example, using a disease-causing gene (gene that causes a disease due to deterioration in function or deficiency thereof) as the gene of interest. In the application (B), mRNA of a cancer antigen is introduced into antigen-presenting cells using the present invention, and a cancer vaccine is produced in the body. When the present invention is applied to the applications (C) and (D), it becomes possible to introduce an initialization factor without using a viral vector, so that the problem of canceration of cells can be overcome.

Formulation when the present invention is used as an RNA medicine can be performed according to a conventional method. At the time of formulation, other components permitted in the formulation (for example, buffers, excipients, disintegrants, emulsifiers, suspension agents, soothing agents, stabilizers, preservatives, antiseptics, physiological saline, carriers, etc.) can be incorporated. As the buffer, a phosphate buffer, a citrate buffer and the like can be used. As the excipient, lactose, starch, sorbitol, D-mannitol, white sugar and the like can be used. As the disintegrant, starch, carboxymethyl cellulose, calcium carbonate and the like can be used. As the buffer, phosphate, citrate, acetate or the like can be used. As the emulsifier, gum arabic, sodium alginate, tragacanth and the like can be used. As the suspension agents monostearate, aluminum monostearate, methyl cellulose, carboxymethyl cellulose, hydroxymethyl cellulose, sodium lauryl sulfate and the like can be used. As the soothing agent, benzyl alcohol, chlorobutanol, sorbitol and the like can be used. As the stabilizer, propylene glycol, ascorbic acid and the like can be used. As the preservative, phenol, benzalkonium chloride, benzyl alcohol, chlorobutanol, methylparaben and the like can be used. As the antiseptic, benzalkonium chloride, paraoxybenzoic acid, chlorobutanol and the like can be used.

A dosage form for formulation is also not particularly limited. Examples of the dosage form are injections, tablets, powders, fine granules, granules, capsules and syrups.

The RNA medicine of the present invention is orally or parenterally administered depending on its dosage form (intravenous, intraarterial, subcutaneous, intradermal, intramuscular, or intraperitoneal injection, transdermal, nasal, transmucosal, etc.) to be applied to the subject. These administration routes are not mutually exclusive, and arbitrarily selected two or more administration routes may be used in combination (for example, intravenous injection or the like is performed simultaneously with oral administration or after a lapse of a predetermined time). The "subject" as used herein is not particularly limited, and includes humans and mammals other than humans (including pet animals, livestock, and experimental animals. Specific examples of the subject include mouse, rat, guinea pig, hamster, monkey, cow, pig, goat, sheep, dog, cat, chicken, and quail. In a preferred embodiment, the RNA medicine of the present invention is applied to humans.

A dosage of the RNA medicine of the present invention is set so as to obtain the expected therapeutic effect. Symptoms, age, gender, body weight, etc. of the patient are generally taken into account when setting a therapeutically effective dosage. Those skilled in the art can set an appropriate dosage in consideration of these matters. As an administration schedule, for example, once to several times a day, once every two days, or once every three days can be adopted. In preparation of the administration schedule, the patient's symptoms and the duration of the effect of the active ingredient can be taken into consideration.

EXAMPLES

1. Purpose

For the purpose of improving the translation efficiency of an artificially synthesized mRNA, which is expected to be used in various clinical applications, in target cells, the following study was conducted.

2. Research Material and Method (1) Plasmid

As a vector for RNA transfection, pBK-5F-EGFP-pA72 was used. As a method for producing pBK-5F-EGFP-pA72, a method described in Nogimori et al., "Dom34 mediates targeting of exogenous RNA in the antiviral OAS/RNase L pathway" Nucleic Acids Research, Volume 47, Issue 1, 10 Jan. 2019, Pages 432-449 was used.

(2) Insertion of Untranslated Region.

Insertion of 5' UTR of GAPDH

Regarding the 5' UTR sequence of GAPDH, oligonucleotides shown in SEQ ID NO: 1 and SEQ ID NO: 2 were hybridized and inserted into the KpnI and XhoI sites of pBK-5F-EGFP-pA72. The 5' UTR sequence of GAPDH is shown in SEQ ID NO: 27.

Insertion of 3' UTR of GAPDH

The 3' UTR sequence of GAPDH was isolated by reverse transcription PCR using total RNA extracted from HeLa cells and oligonucleotides shown in SEQ ID NO: 3 and SEQ ID NO: 4. The isolated sequence was inserted into the EcoRI and XbaI sites of pBK-5F-EGFP-pA72. The 3' UTR sequence of GAPDH is shown in SEQ ID NO: 28.

Insertion of 5' UTR of ACAT2

The 5' UTR sequence of ACAT2 was isolated by reverse transcription PCR using total RNA extracted from HeLa cells and oligonucleotides shown in SEQ ID NO: 5 and SEQ ID NO: 6. The isolated sequence was inserted into the KpnI and XhoI sites of pBK-5F-EGFP-pA72. The 5' UTR sequence of ACAT2 is shown in SEQ ID NO: 29.

Insertion of 3' UTR of ACAT2

The 3' UTR sequence of ACAT2 was isolated by reverse transcription PCR using total RNA extracted from HeLa cells and oligonucleotides shown in SEQ ID NO: 7 and SEQ ID NO: 8. The isolated sequence was inserted into the EcoRI and XbaI sites of pBK-5F-EGFP-pA72. The 3' UTR sequence of ACAT2 is shown in SEQ ID NO: 30.

Insertion of 5' UTR of LDHB

The 5' UTR sequence of LDHB was isolated by reverse transcription PCR using total RNA extracted from HeLa cells and oligonucleotides shown in SEQ ID NO: 9 and SEQ ID NO: 10. The isolated sequence was inserted into the KpnI and XhoI sites of pBK-5F-EGFP-pA72. The 5' UTR sequence of LDHB is shown in SEQ ID NO: 31.

Insertion of 3' UTR of LDHB

The 3' UTR sequence of LDHB was isolated by reverse transcription PCR using total RNA extracted from HeLa cells and oligonucleotides shown in SEQ ID NO: 11 and SEQ ID NO: 12. The isolated sequence was inserted into the EcoRI and XbaI sites of pBK-5F-EGFP-pA72. The 3' UTR sequence of LDHB is shown in SEQ ID NO: 32.

Insertion of 3' UTR completely complementary to 5' UTR sequence of GAPDH

Regarding the 3' UTR sequence completely complementary to the 5' UTR sequence of GAPDH, oligonucleotides shown in SEQ ID NO: 13 and SEQ ID NO: 14 were hybridized and inserted into the KpnI and XhoI sites of pBK-5F-EGFP-pA72. The 3' UTR sequence completely complementary to the 5' UTR sequence of GAPDH is shown in SEQ ID NO: 33.

Insertion of 3' UTR with 94% complementarity to 5' UTR sequence of GAPDH

Regarding the 3' UTR sequence with 94% complementarity to the 5' UTR sequence of GAPDH, oligonucleotides shown in SEQ ID NO: 15 and SEQ ID NO: 16 were hybridized and inserted into the KpnI and XhoI sites of pBK-5F-EGFP-pA72. The 3' UTR sequence with 94% complementarity to the 5' UTR sequence of GAPDH is shown in SEQ ID NO: 34.

Insertion of 3' UTR with 88% complementarity to 5' UTR sequence of GAPDH

Regarding the 3' UTR sequence with 88% complementarity to the 5' UTR sequence of GAPDH, oligonucleotides shown in SEQ ID NO: 17 and SEQ ID NO: 18 were hybridized and inserted into the KpnI and XhoI sites of pBK-5F-EGFP-pA72. The 3' UTR sequence with 88% complementarity to the 5' UTR sequence of GAPDH is shown in SEQ ID NO: 35.

Insertion of 3' UTR with 75% complementarity to 5' UTR sequence of GAPDH

Regarding the 3' UTR sequence with 75% complementarity to the 5' UTR sequence of GAPDH, oligonucleotides shown in SEQ ID NO: 19 and SEQ ID NO: 20 were hybridized and inserted into the KpnI and XhoI sites of pBK-5F-EGFP-pA72. The 3' UTR sequence with 75% complementarity to the 5' UTR sequence of GAPDH is shown in SEQ ID NO: 36.

Insertion of 3' UTR with 50% complementarity to 5' UTR sequence of GAPDH

Regarding the 3' UTR sequence with 50% complementarity to the 5' UTR sequence of GAPDH, oligonucleotides shown in SEQ ID NO: 21 and SEQ ID NO: 22 were hybridized and inserted into the KpnI and XhoI sites of pBK-5F-EGFP-pA72. The 3' UTR sequence with 50% complementarity to the 5' UTR sequence of GAPDH is shown in SEQ ID NO: 37.

Insertion of 3' UTR with 25% complementarity to 5' UTR sequence of GAPDH

Regarding the 3' UTR sequence with 25% complementarity to the 5' UTR sequence of GAPDH, oligonucleotides shown in SEQ ID NO: 23 and SEQ ID NO: 24 were hybridized and inserted into the KpnI and XhoI sites of pBK-5F-EGFP-pA72. The 3' UTR sequence with 25% complementarity to the 5' UTR sequence of GAPDH is shown in SEQ ID NO: 38.

Insertion of 5' UTR of B-globin

Regarding the 5' UTR sequence of B-globin, oligonucleotides shown in SEQ ID NO: 41 and SEQ ID NO: 42 were hybridized and inserted into the KpnI and XhoI sites of pBK-5F-EGFP-pA72. The 5' UTR sequence of 8-globin is shown in SEQ ID NO: 94.

Insertion of 3' UTR completely complementary to 5' UTR sequence of 6-globin

Regarding the 3' UTR sequence completely complementary to the 5' UTR sequence of B-globin, oligonucleotides shown in SEQ ID NO: 43 and SEQ ID NO: 44 were hybridized and inserted into the EcoRI and XbaI sites of pBK-5F-EGFP-pA72. The 3' UTR sequence completely complementary to the 5' UTR sequence of B-globin is shown in SEQ ID NO: 95.

Insertion of 3' UTR with 92% complementarity to 5' UTR sequence of 8-globin

Regarding the 3' UTR sequence with 92% complementarity to the 5' UTR sequence of B-globin, oligonucleotides shown in SEQ ID NO: 45 and SEQ ID NO: 46 were hybridized and inserted into the EcoRI and XbaI sites of pBK-5F-EGFP-pA72. The 3' UTR sequence with 92% complementarity to the 5' UTR sequence of 6-globin is shown in SEQ ID NO: 96.

Insertion of 3' UTR with 88% complementarity to 5' UTR sequence of-globin

Regarding the 3' UTR sequence with 88% complementarity to the 5' UTR sequence of B-globin, oligonucleotides shown in SEQ ID NO: 47 and SEQ ID NO: 48 were hybridized and inserted into the EcoRI and XbaI sites of pBK-5F-EGFP-pA72. The 3' UTR sequence with 88% complementarity to the 5' UTR sequence of B-globin is shown in SEQ ID NO: 97.

Insertion of 3' UTR with 74% complementarity to 5' UTR sequence of B-globin

Regarding the 3' UTR sequence with 74% complementarity to the 5' UTR sequence of B-globin, oligonucleotides shown in SEQ ID NO: 49 and SEQ ID NO: 50 were hybridized and inserted into the EcoRI and XbaI sites of pBK-5F-EGFP-pA72. The 3' UTR sequence with 74% complementarity to the 5' UTR sequence of B-globin is shown in SEQ ID NO: 98.

Insertion of 3' UTR with 50% complementarity to 5' UTR sequence of 8-globin

Regarding the 3' UTR sequence with 50% complementarity to the 5' UTR sequence of B-globin, oligonucleotides shown in SEQ ID NO: 51 and SEQ ID NO: 52 were hybridized and inserted into the EcoRI and XbaI sites of pBK-5F-EGFP-pA72. The 3' UTR sequence with 50% complementarity to the 5' UTR sequence of B-globin is shown in SEQ ID NO: 99.

Insertion of 3' UTR with 24% complementarity to 5' UTR sequence of B-globin

Regarding the 3' UTR sequence with 24% complementarity to the 5' UTR sequence of B-globin, oligonucleotides shown in SEQ ID NO: 53 and SEQ ID NO: 54 were hybridized and inserted into the EcoRI and XbaI sites of pBK-5F-EGFP-pA72. The 3' UTR sequence with 24% complementarity to the 5' UTR sequence of B-globin is shown in SEQ ID NO: 100.

Insertion of 5' UTR of RPS8

Regarding the 5' UTR sequence of RPS8, oligonucleotides shown in SEQ ID NO: 55 and SEQ ID NO: 56 were hybridized and inserted into the KpnI and XhoI sites of pBK-5F-EGFP-pA72. The 5' UTR sequence of RPS8 is shown in SEQ ID NO: 101.

Insertion of 3' UTR completely complementary to 5' UTR sequence of RPS8

Regarding the 3' UTR sequence completely complementary to the 5' UTR sequence of RPS8, oligonucleotides shown in SEQ ID NO: 57 and SEQ ID NO: 58 were hybridized and inserted into the EcoRI and XbaI sites of pBK-5F-EGFP-pA72. The 3' UTR sequence completely complementary to the 5' UTR sequence of RPS8 is shown in SEQ ID NO: 102.

Insertion of 3' UTR with 93% complementarity to 5' UTR sequence of RPS8

Regarding the 3' UTR sequence with 93% complementarity to the 5' UTR sequence of RPS8, oligonucleotides shown in SEQ ID NO: 59 and SEQ ID NO: 60 were hybridized and inserted into the EcoRI and XbaI sites of pBK-5F-EGFP-pA72. The 3' UTR sequence with 93% complementarity to the 5' UTR sequence of RPS8 is shown in SEQ ID NO: 103.

Insertion of 3' UTR with 86% complementarity to 5' UTR sequence of RPS8

Regarding the 3' UTR sequence with 86% complementarity to the 5' UTR sequence of RPS8, oligonucleotides shown in SEQ ID NO: 61 and SEQ ID NO: 62 were hybridized and inserted into the EcoRI and XbaI sites of pBK-5F-EGFP-pA72. The 3' UTR sequence with 86% complementarity to the 5' UTR sequence of RPS8 is shown in SEQ ID NO: 104.

Insertion of 3' UTR with 71% complementarity to 5' UTR sequence of RPS8

Regarding the 3' UTR sequence with 71% complementarity to the 5' UTR sequence of RPS8, oligonucleotides shown in SEQ ID NO: 63 and SEQ ID NO: 64 were hybridized and inserted into the EcoRI and XbaI sites of pBK-5F-EGFP-pA72. The 3' UTR sequence with 71% complementarity to the 5' UTR sequence of RPS8 is shown in SEQ ID NO: 105.

Insertion of 3' UTR with 50% complementarity to 5' UTR sequence of RPS8

Regarding the 3' UTR sequence with 50% complementarity to the 5' UTR sequence of RPS8, oligonucleotides shown in SEQ ID NO: 65 and SEQ ID NO: 66 were hybridized and inserted into the EcoRI and XbaI sites of pBK-5F-EGFP-pA72. The 3' UTR sequence with 50% complementarity to the 5' UTR sequence of RPS8 is shown in SEQ ID NO: 106.

Insertion of 3' UTR with 29% complementarity to 5' UTR sequence of RPS8

Regarding the 3' UTR sequence with 29% complementarity to the 5' UTR sequence of RPS8, oligonucleotides shown in SEQ ID NO: 67 and SEQ ID NO: 68 were hybridized and inserted into the EcoRI and XbaI sites of pBK-5F-EGFP-pA72. The 3' UTR sequence with 29% complementarity to the 5' UTR sequence of RPS8 is shown in SEQ ID NO: 107.

Insertion of 3' UTR with 14% complementarity to 5' UTR sequence of RPS8

Regarding the 3' UTR sequence with 14% complementarity to the 5' UTR sequence of RPS8, oligonucleotides shown in SEQ ID NO: 69 and SEQ ID NO: 70 were hybridized and inserted into the EcoRI and XbaI sites of pBK-5F-EGFP-pA72. The 3' UTR sequence with 14% complementarity to the 5' UTR sequence of RPS8 is shown in SEQ ID NO: 108.

Insertion of 3' UTR completely complementary to 5' UTR sequence of LDHB

Regarding the 3' UTR sequence completely complementary to the 5' UTR sequence of LDHB, oligonucleotides shown in SEQ ID NO: 71 and SEQ ID NO: 72 were hybridized and inserted into the EcoRI and XbaI sites of pBK-5F-EGFP-pA72. The 3' UTR sequence completely complementary to the 5' UTR sequence of LDHB is shown in SEQ ID NO: 109.

Insertion of 3' UTR with 93% complementarity to 5' UTR sequence of LDHB

Regarding the 3' UTR sequence with 93% complementarity to the 5' UTR sequence of LDHB, oligonucleotides shown in SEQ ID NO: 73 and SEQ ID NO: 74 were hybridized and inserted into the EcoRI and XbaI sites of pBK-5F-EGFP-pA72. The 3' UTR sequence with 93% complementarity to the 5' UTR sequence of LDHB is shown in SEQ ID NO: 110.

Insertion of 3' UTR with 87% complementarity to 5' UTR sequence of LDHB

Regarding the 3' UTR sequence with 87% complementarity to the 5' UTR sequence of LDHB, oligonucleotides shown in SEQ ID NO: 75 and SEQ ID NO: 76 were hybridized and inserted into the EcoRI and XbaI sites of pBK-5F-EGFP-pA72. The 3' UTR sequence with 87% complementarity to the 5' UTR sequence of LDHB is shown in SEQ ID NO: 111.

Insertion of 3' UTR with 75% complementarity to 5' UTR sequence of LDHB

Regarding the 3' UTR sequence with 75% complementarity to the 5' UTR sequence of LDHB, oligonucleotides shown in SEQ ID NO: 77 and SEQ ID NO: 78 were hybridized and inserted into the EcoRI and XbaI sites of pBK-5F-EGFP-pA72. The 3' UTR sequence with 75% complementarity to the 5' UTR sequence of LDHB is shown in SEQ ID NO: 112.

Insertion of 3' UTR with 50% complementarity to 5' UTR sequence of LDHB

Regarding the 3' UTR sequence with 50% complementarity to the 5' UTR sequence of LDHB, oligonucleotides shown in SEQ ID NO: 79 and SEQ ID NO: 80 were hybridized and inserted into the EcoRI and XbaI sites of pBK-5F-EGFP-pA72. The 3' UTR sequence with 50% complementarity to the 5' UTR sequence of LDHB is shown in SEQ ID NO: 113.

Insertion of 3' UTR with 25% complementarity to 5' UTR sequence of LDHB

Regarding the 3' UTR sequence with 25% complementarity to the 5' UTR sequence of LDHB, oligonucleotides shown in SEQ ID NO: 81 and SEQ ID NO: 82 were hybridized and inserted into the EcoRI and XbaI sites of pBK-5F-EGFP-pA72. The 3' UTR sequence with 25% complementarity to the 5' UTR sequence of LDHB is shown in SEQ ID NO: 114.

Production of Cas9 mRNA synthesis plasmid

The cDNA sequence of Cas9 was isolated by a PCR using the hCas9 plasmid (Addgene plasmid #41815) described in Mail et al "RNA-guided human genome engineering via Cas9" Science. 2013 Feb. 15; 339 (6121): 823-6 and oligonucleotides shown in SEQ ID NO: 83 and SEQ ID NO: 84. A pBK-F-hCas9-pA72 plasmid was obtained by inverse PCR using a plasmid in which the isolated sequence was inserted into the HindIII site of pBK-5F-EGFP-pA72 and oligonucleotides shown in SEQ ID NO: 83 and SEQ ID NO: 85. The cDNA sequence of hCas9 is shown in SEQ ID NO: 115, and the amino acid sequence of hCas9 is shown in SEQ ID NO: 116.

Insertion of 5' UTR of GAPDH into Cas9 mRNA synthesis plasmid

The 5' UTR of GAPDH was inserted by inverse PCR using the pBK-F-hCas9-pA72 plasmid and oligonucleotides shown in SEQ ID NO: 86 and SEQ ID NO: 87. The 5' UTR sequence of GAPDH is shown in SEQ ID NO: 27.

Insertion of 3' UTR with 75% complementarity to 5' UTR sequence of GAPDH into Cas9 mRNA synthesis plasmid The 3' UTR with 75% complementarity to the 5' UTR sequence of GAPDH was inserted by inverse PCR using the pBK-F-hCas9-pA72 plasmid and oligonucleotides shown in SEQ ID NO: 88 and SEQ ID NO: 89. The 3' UTR sequence with 75% complementarity to the 5' UTR sequence of GAPDH is shown in SEQ ID NO: 36.

Insertion of 3' UTR with 50% complementarity to 5' UTR sequence of GAPDH into Cas9 mRNA synthesis plasmid The 3' UTR with 50% complementarity to the 5' UTR sequence of GAPDH was inserted by inverse PCR using the pBK-F-hCas9-pA72 plasmid and oligonucleotides shown in SEQ ID NO: 90 and SEQ ID NO: 91. The 3' UTR sequence with 50% complementarity to the 5' UTR sequence of GAPDH is shown in SEQ ID NO: 37.

Insertion of cDNA of p53

The cDNA sequence of p53 was isolated by reverse transcription PCR using total RNA extracted from U2OS cells and oligonucleotides shown in SEQ ID NO: 25 and SEQ ID NO: 26. The isolated cDNA sequence of p53 was inserted into the HindIII site of pBK-5F-EGFP-pA72. The cDNA sequence of p53 is shown in SEQ ID NO: 39, and the amino acid sequence of p53 is shown in SEQ ID NO: 40.

(3) RNA Synthesis

Products obtained by treating the various pBK-5F-EGFP-pA72, various pBK-5F-p53-pA72 and various pBK-F-hCas9-pA72 plasmids with BsmBI were used as templates to synthesize 5×Flag-EGFP-pA72, 5×Flag-p53-pA72 and Flag-hCas9-pA72 mRNAs. RNA synthesis was performed using T7 RNA polymerase (Takara Bio Inc.) according to the instruction manual for this T7 RNA polymerase.

(4) Transfection

HeLa cells, 293T cells, and U2OS cells were all cultured at 37° C. in the presence of 5% $CO_2$ using Dulbecco's Modified Eagle's Medium (NISSUI PHARMACEUTICAL CO., LTD.) added with 5% fetal bovine serum. The HeLa cells were seeded on a 35-mm dish so as to be about 50% confluent, and then cultured for 24 hours. Thereafter, the various synthesized RNAs were introduced using Lipofectamine RNAiMAX (Life Technologies Japan Ltd.) according to the instruction manual therefor.

(5) Analysis of RNA

Total RNA from the HeLa cells after RNA transfection was isolated by an AGPC (acid guanidinium thiocyanate-phenol-chloroform extraction) method which is a method using guanidine thiocyanate, acidic phenol and chloroform. The prepared total RNA was separated with an agarose MOPS buffer gel (20 mM MOPS (pH 7.0), 5 mM sodium acetate, 1 mM EDTA, 2.0% Agarose, and 2.46 M formaldehyde), and then transcribed to a nylon membrane Biodyne-B (Nihon Pall Ltd.) in a 20×SSC buffer. The nylon membrane after transcription was fixed with UV, followed by hybridization using a DIG-labeled probe. Production of the DIG-labeled probe and hybridization were performed using DIG RNA Labeling Mix (Roche Diagnostics K.K.) and DIG Wash and Block Buffer Set (Roche Diagnostics K.K.) according to the instruction manual. Using a chemiluminescent reagent CDP-Star (Roche Diagnostics K.K.), mRNA was detected by LAS 3000 mini (Fuji Photo Film Co., Ltd.).

(6) Analysis of Protein

Intracellular expression of a proteins was performed by the following Western blotting. A protein lysate from the cells after introduction was adjusted using an SDS-PAGE sample buffer (50 mM Tris-HCl (pH 6.8), 4% glycerol, 2% SDS, 2% 2-mercaptoethanol, and 0.004% bromophenol blue). The protein lysate was separated by SDS-PAGE using 8, 10, 12, or 15% acrylamide, and then electrically transcribed to a nitrocellulose membrane BioTrace NC (Nihon Pall Ltd.). The nitrocellulose membrane after transcription was incubated with an anti-Flag M2 mouse monoclonal antibody (Sigma-Aldrich Japan K.K.), an anti-GAPDH antibody (Saito et al JBC), an anti-PABPC1 antibody (Osawa et al RNA (2012)), and a peroxidase-added anti-mouse IgG (Jackson ImmunoResearch Laboratories, Inc.) or peroxidase-added anti-rabbit IgG (Jackson ImmunoResearch Laboratories, Inc.). The peroxidase enzyme activity on the nitrocellulose membrane was detected by LAS 3000 mini (Fuji Photo Film Co., Ltd.) using luminol chemiluminescence.

(7) Quantification of AAVS Region Genome Editing Efficiency

The genome editing efficiency was quantified by a T7 endonuclease assay method which will be indicated below. Various hCas9 mRNAs synthesized with sgRNA recognizing the AAVS region (Thermo Fisher Scientific Inc.) were introduced into Hela cells. The introduced cells were treated with 50 mM NaOH to adjust genomic DNAs. The AAVS genome sequences were amplified by PCR using the adjusted genomic DNAs and oligonucleotides shown in SEQ ID NO: 92 and SEQ ID NO: 93. The amplified genome sequences were heat denatured and then annealed to obtain sequences containing a mismatch. The annealed AAVS genome sequences were treated with T7 endonuclease I (New England Biolabs Inc.). The AAVS genome sequences after treatment were separated by agarose gel electrophoresis, then stained with ethidium bromide and detected by Typhoon 9400 (GE Healthcare).

3. Experimental Results (i) Experiment 1

FIG. 1 is a view illustrating the artificially synthesized mRNAs produced. The artificially synthesized mRNAs illustrated in FIG. 1 are, from top to bottom, an artificially synthesized mRNA having the 5' UTR sequence of GAPDH and the 3' UTR sequence of GAPDH, an artificially synthesized mRNA having the 5' UTR sequence of LDHB and the 3' UTR sequence of LDHB, and an artificially synthesized mRNA having the 5' UTR sequence of ACAT2 and the 3' UTR sequence of ACAT2. A cap structure is added to the 5' end of the artificially synthesized mRNA used in this experiment, and a 72-base poly-A tail is added to the 3' end thereof. The ORE, which is the protein coding region of the artificially synthesized mRNAs used in this experiment, has enhanced green fluorescent protein (EGFP) added with a 5x Flag tag.

Figure 2:
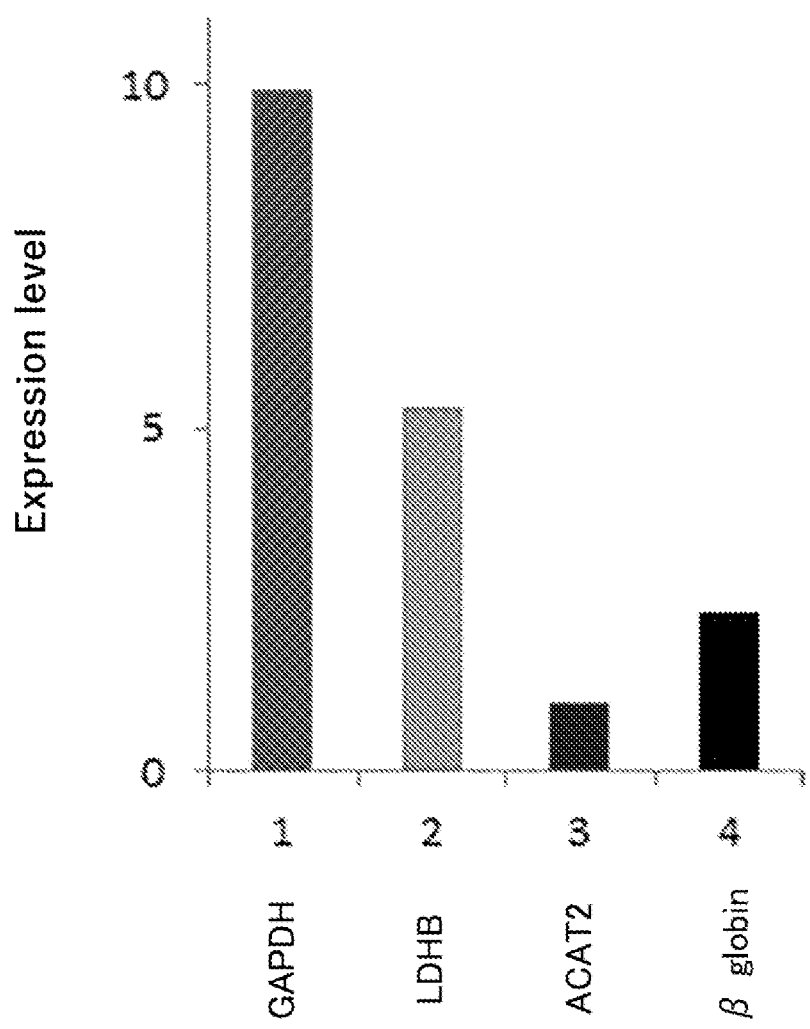
FIG. 2 A view illustrating results of measuring expression levels of proteins from the artificially synthesized mRNAs.

FIG. 2 is a view illustrating results of measuring expression levels of proteins from the artificially synthesized mRNAs. The protein expression levels were measured by introducing the artificially synthesized mRNAs illustrated in FIG. 1 into HeLa cells. FIG. 2 illustrates the expression level of each of the artificially synthesized mRNAs.

FIG. 2 illustrates relative values of the expression levels when the expression level of the artificially synthesized mRNA having the UTR sequences of ACAT2 is 1. In FIG. 2, results of an artificially synthesized mRNA having a 3' UTR of B-globin are also illustrated for reference.

From the results of FIG. 2, it was found that the expression level of the artificially synthesized mRNA having the UTR sequences of GAPDH was about 10 times as large as that of the artificially synthesized mRNA having the UTR sequences of ACAT2. In addition, it was found that the expression level of the artificially synthesized mRNA having the UTR sequences of GAPDH was about 5 times as large as that of the artificially synthesized mRNA having the 3' UTR sequence of B-globin that is normally used as an artificially synthesized mRNA having a high expression efficiency.

Figure 3:
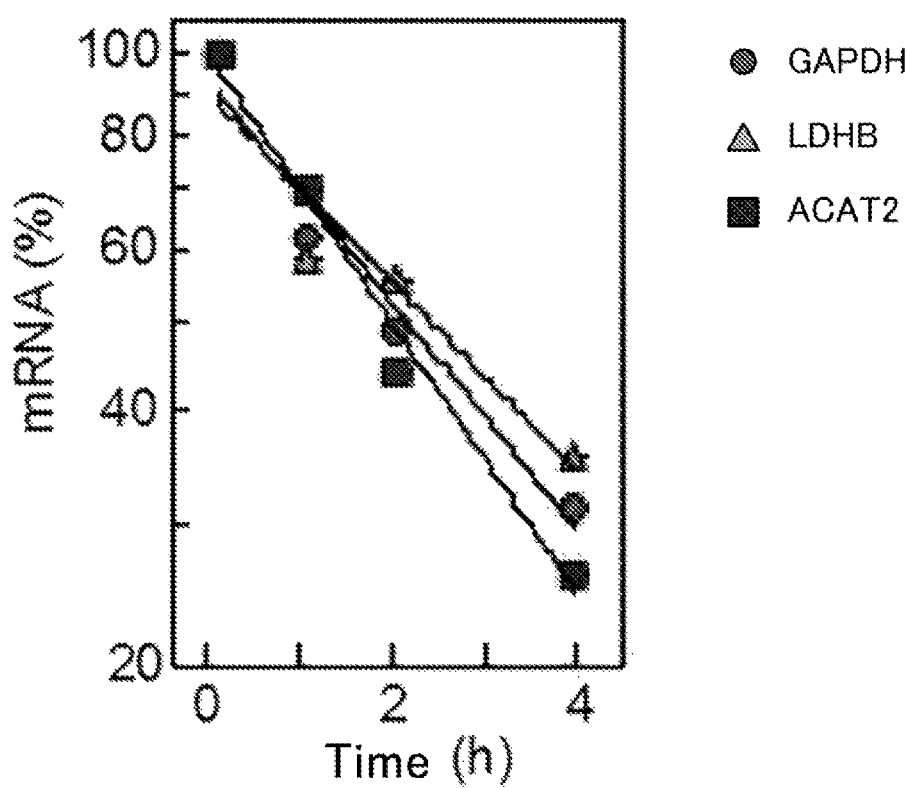
FIG. 3 A view illustrating stability of the artificially synthesized mRNAs illustrated in FIG. 1.

FIG. 3 is a view illustrating stability of the artificially synthesized mRNAs illustrated in FIG. 1. The horizontal axis in FIG. 3 represents the elapsed time from the introduction of the artificially synthesized mRNA into the cell, and the vertical axis in FIG. 3 represents the amount of mRNA when the amount of mRNA when the artificially synthesized mRNA was introduced into the cell is 100%.

From the results of FIG. 3, it was found that all the artificially synthesized mRNAs showed similar degradation rates in the HeLa cells. From the results illustrated in FIGS. 2 and 3, it was found that the effect exhibited by the 5' UTR sequence of GAPDH and the 3' UTR sequence of GAPDH is not an effect of improving the stability, but an effect of improving the translation efficiency.

(ii) Experiment 2

Figure 4:
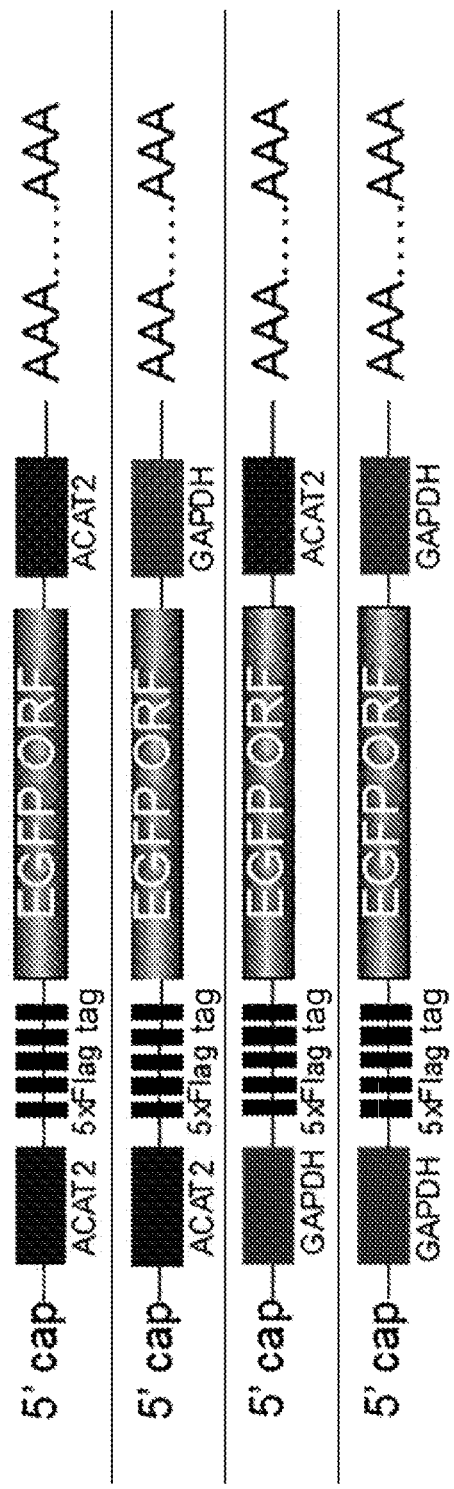
FIG. 4 A view illustrating artificially synthesized mRNAs produced.

FIG. 4 is a view illustrating artificially synthesized mRNAs produced. The artificially synthesized mRNAs illustrated in FIG. 4 are, from top to bottom, an artificially synthesized mRNA having the 5' UTR sequence of ACAT2 and the 3' UTR sequence of ACAT2, an artificially synthesized mRNA having the 5' UTR sequence of ACAT2 and the 3' UTR sequence of GAPDH, an artificially synthesized mRNA having the 5'UTR sequence of GAPDH and the 3' UTR sequence of ACAT2, and an artificially synthesized mRNA having the 5' UTR sequence of GAPDH and the 3' UTR sequence of GAPDH. A cap structure is added to the 5' end of the artificially synthesized mRNA used in this experiment, and a 72-base poly-A tail is added to the 3' end thereof. In addition, the ORF, which is the protein coding region of the artificially synthesized mRNAs used in this experiment, has EGFP added with a 5x Flag tag.

Figure 5:
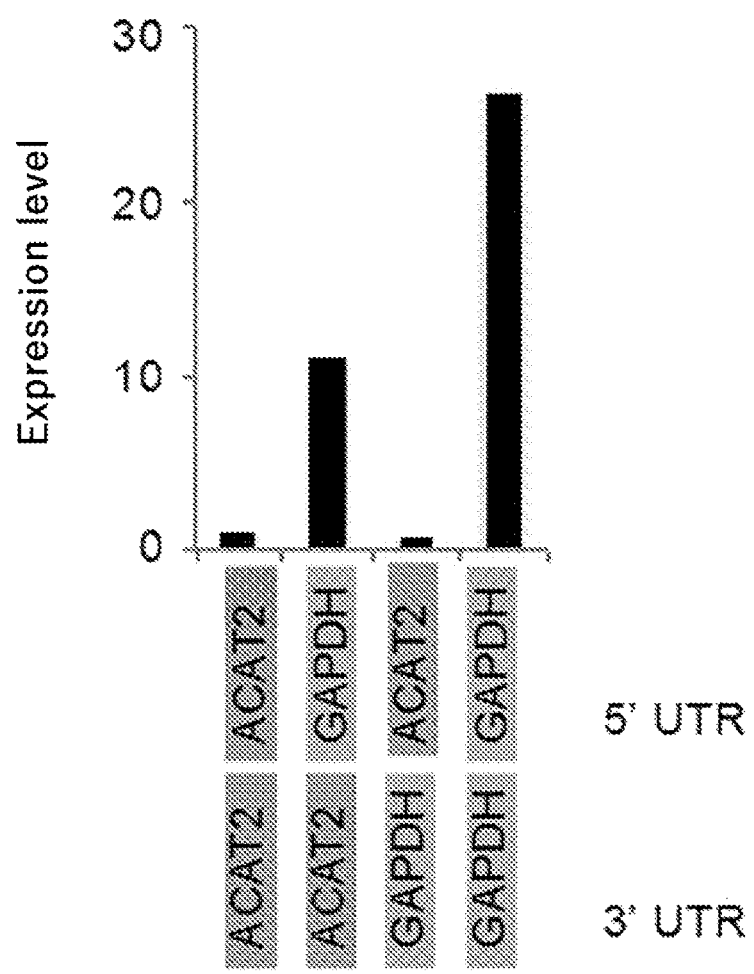
FIG. 5 A view illustrating an expression level for each of the artificially synthesized mRNAs.

FIG. 5 is a view illustrating the expression level of each of the artificially synthesized mRNAs. The protein expression levels were measured by introducing the artificially synthesized mRNAs illustrated in FIG. 4 into HeLa cells. FIG. 5 illustrates relative values of the expression levels when the expression level of the artificially synthesized mRNA having the 5' UTR sequence of ACAT2 and the 3' UTR sequence of ACAT2 is 1.

From the results of FIG. 5, it was found that the expression level of the artificially synthesized mRNA having the 5' UTR sequence of GAPDH and the 3' UTR sequence of ACAT2 was about 10 times as large as that of the artificially synthesized mRNA having the 5' UTR sequence of ACAT2 and the 3' UTR sequence of ACAT2. Further, it was found that the expression level of the artificially synthesized mRNA having the 5' UTR sequence of GAPDH and the 3' UTR sequence of GAPDH was about 25 times as large as that of the artificially synthesized mRNA having the 5' UTR sequence of ACAT2 and the 3' UTR sequence of ACAT2. That is, it was found that the effect of improving the translation efficiency can be obtained due to inclusion of the artificially synthesized mRNA has the 5' UTR sequence of GAPDH, and further that a synergistic effect of improving the translation efficiency can be obtained due to inclusion of the 3' UTR sequence of GAPDH.

Figure 6:
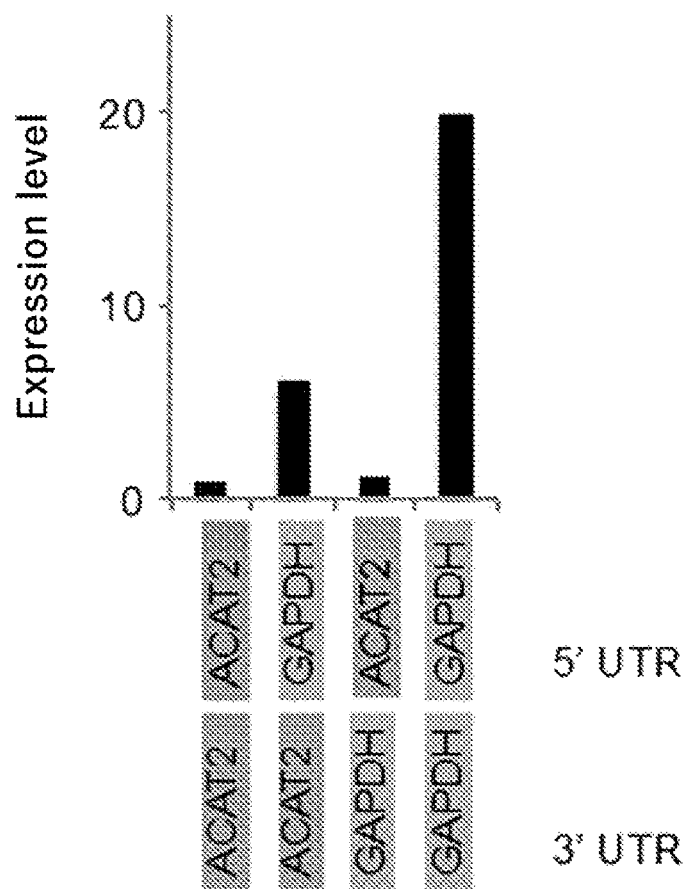
FIG. 6 A view illustrating an expression level for each of the artificially synthesized mRNAs when the artificially synthesized mRNA is introduced into HEK 293 cells derived from kidney.

FIG. 6 is a view illustrating an expression level for each of the artificially synthesized mRNAs when the artificially synthesized mRNA is introduced into HEK 293 cells derived from kidney. The experiment was performed in the same manner as in the experiment related to FIG. 5, except that the cells to be introduced were changed. Also from the results of FIG. 6, the same tendency as that found from the results of FIG. 5 was observed. That is, it was found that the effect of improving the translation efficiency can be obtained due to inclusion of the artificially synthesized mRNA has the 5' UTR sequence of GAPDH, and further that a synergistic effect of improving the translation efficiency can be obtained due to inclusion of the 3' UTR sequence of GAPDH. From the experimental results related to FIGS. 5 and 6, it was found that the effect of improving the translation efficiency obtained due to inclusion of the UTR sequences of GAPDH was effective also in all the cells and was not cell specific.

(iii) Experiment 3

Figure 7:
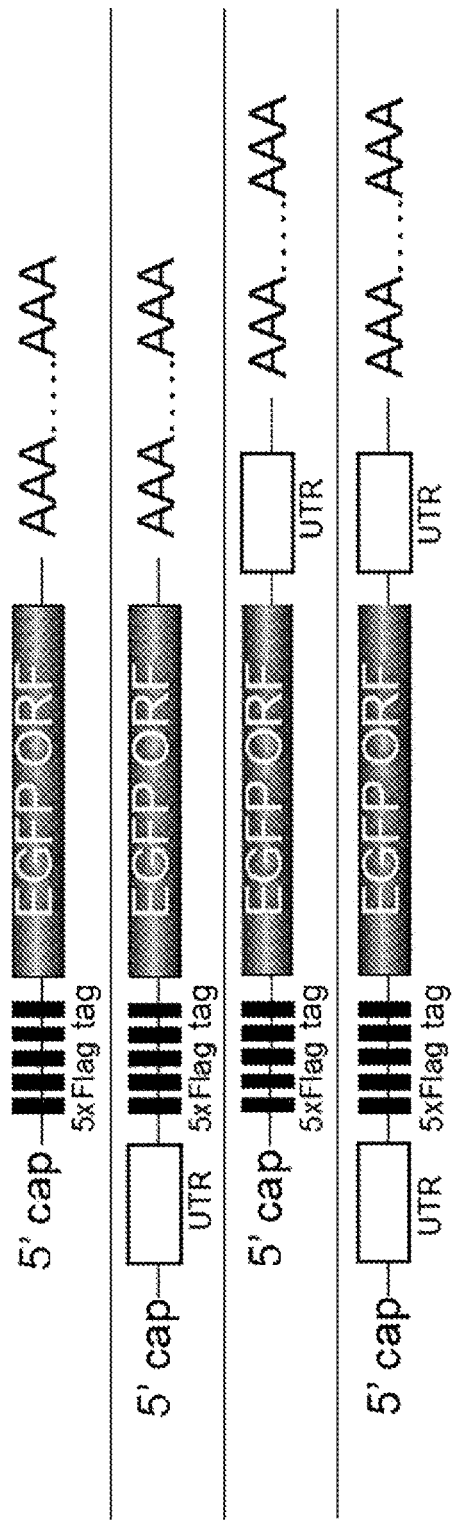
FIG. 7 A view illustrating artificially synthesized mRNAs produced.

FIG. 7 is a view illustrating artificially synthesized mRNAs produced. The artificially synthesized mRNAs illustrated in FIG. 7 are, from top to bottom, an artificially synthesized mRNA having no UTR sequence, an artificially synthesized mRNA having a 5'UTR sequence, but having no 3' UTR sequence, an artificially synthesized mRNA having no 5' UTR sequence, but having a 3' UTR sequence, and an artificially synthesized mRNA having a 5' UTR sequence and a 3' UTR sequence. A cap structure is added to the 5' end of the artificially synthesized mRNA used in this experiment, and a 72-base poly-A tail is added to the 3' end thereof. In addition, the ORF, which is the protein coding region of the artificially synthesized mRNAs used in this experiment, has EGFP added with a 5x Flag tag.

Figure 8:
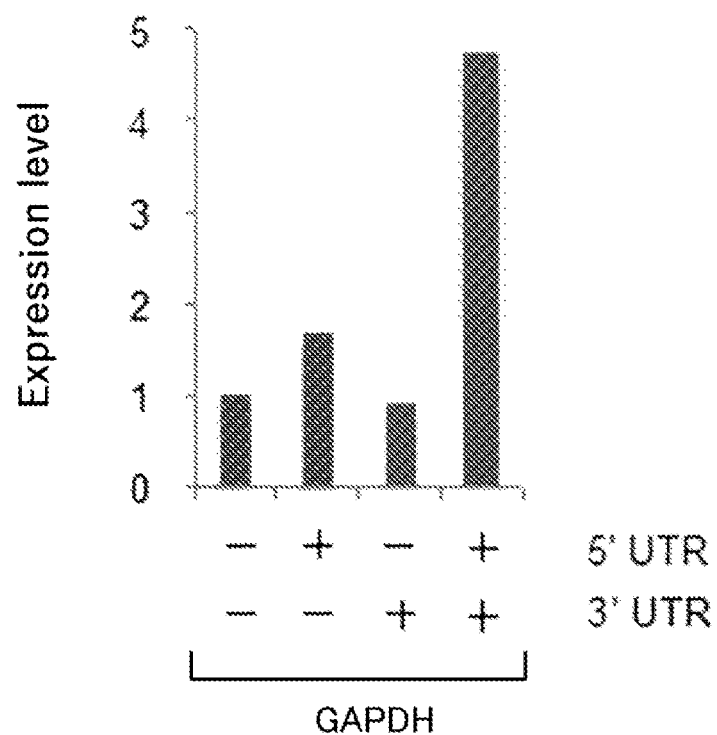
FIG. 8 A view illustrating a difference in expression level caused by the presence or absence of UTR sequences of GAPDH.
Figure 9:
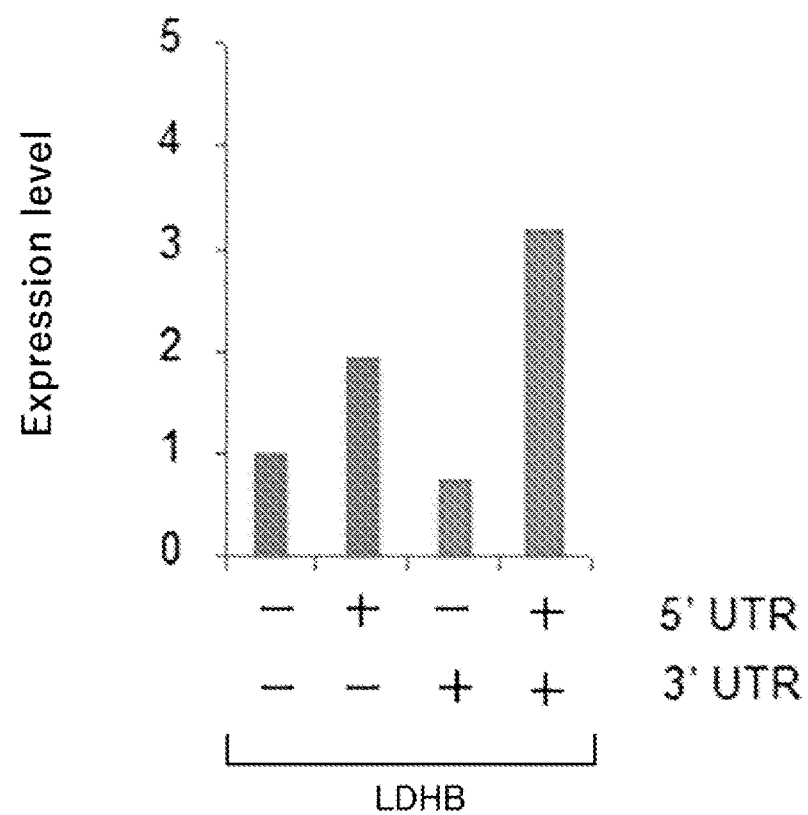
FIG. 9 A view illustrating a difference in expression level caused by the presence or absence of UTR sequences of LDHB.
Figure 10:
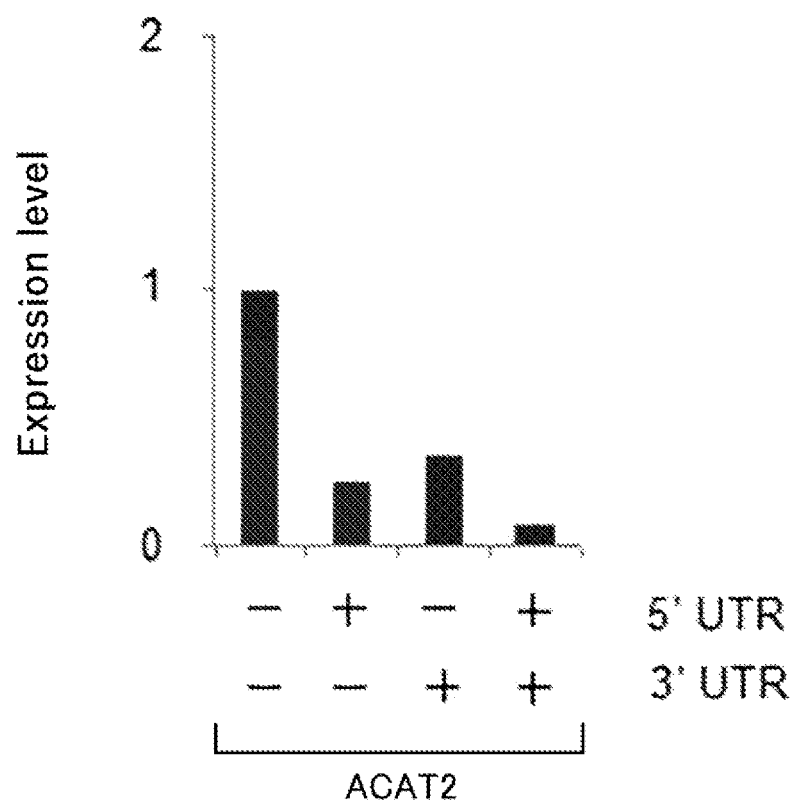
FIG. 10 A view illustrating a difference in expression level caused by the presence or absence of UTR sequences of ACAT2.

FIG. 8 is a view illustrating a difference in expression level caused by the presence or absence of the UTR sequences of GAPDH. FIG. 9 is a view illustrating a difference in expression level caused by the presence or absence of the UTR sequences of LDHB. FIG. 10 is a view illustrating a difference in expression level caused by the presence or absence of the UTR sequences of ACAT2. The protein expression levels were measured by introducing the artificially synthesized mRNAs illustrated in FIG. 7 into HeLa cells. FIGS. 8, 9 and 10 each illustrate relative values of the expression levels when the expression level of the artificially synthesized mRNA having no UTR sequence is 1.

From the results of FIG. 8, the expression level of the artificially synthesized mRNA having the 5' UTR sequence of GAPDH and the 3' UTR sequence of GAPDH is larger than the sum of the expression level of the artificially synthesized mRNA having the 5' UTR sequence, but having no 3' UTR sequence and the expression level of the artificially synthesized mRNA having no 5' UTR sequence, but having the 3' UTR sequence. That is, it was found that a synergistic effect of improving the translation efficiency can be obtained due to inclusion of the artificially synthesized mRNA has the 5' UTR sequence of GAPDH and the 3' UTR sequence of GAPDH.

From the results of FIG. 9, the expression level of the artificially synthesized mRNA having the 5' UTR sequence of LDHB and the 3' UTR sequence of LDHB was equal to the sum of the expression level of the artificially synthesized mRNA having the 5' UTR sequence, but having no 3' UTR sequence and the expression level of the artificially synthesized mRNA having no 5' UTR sequence, but having the 3' UTR sequence. That is, the effect obtained by inclusion of the 5' UTR sequence of LDHB and the 3' UTR sequence of LDHB was only an additive effect.

From the results of FIG. 10, it was found that the expression level of the artificially synthesized mRNA having the UTR sequences of ACAT2 was reduced in translation efficiency as compared with the expression level of the artificially synthesized mRNA having no UTR sequence. From the results of FIGS. 8 to 10, it was found that the synergistic effect of improving the translation efficiency obtained due to inclusion of the 5' UTR sequence and the 3' UTR sequence was characteristic of GAPDH.

(iv) Experiment 4

Figure 11:
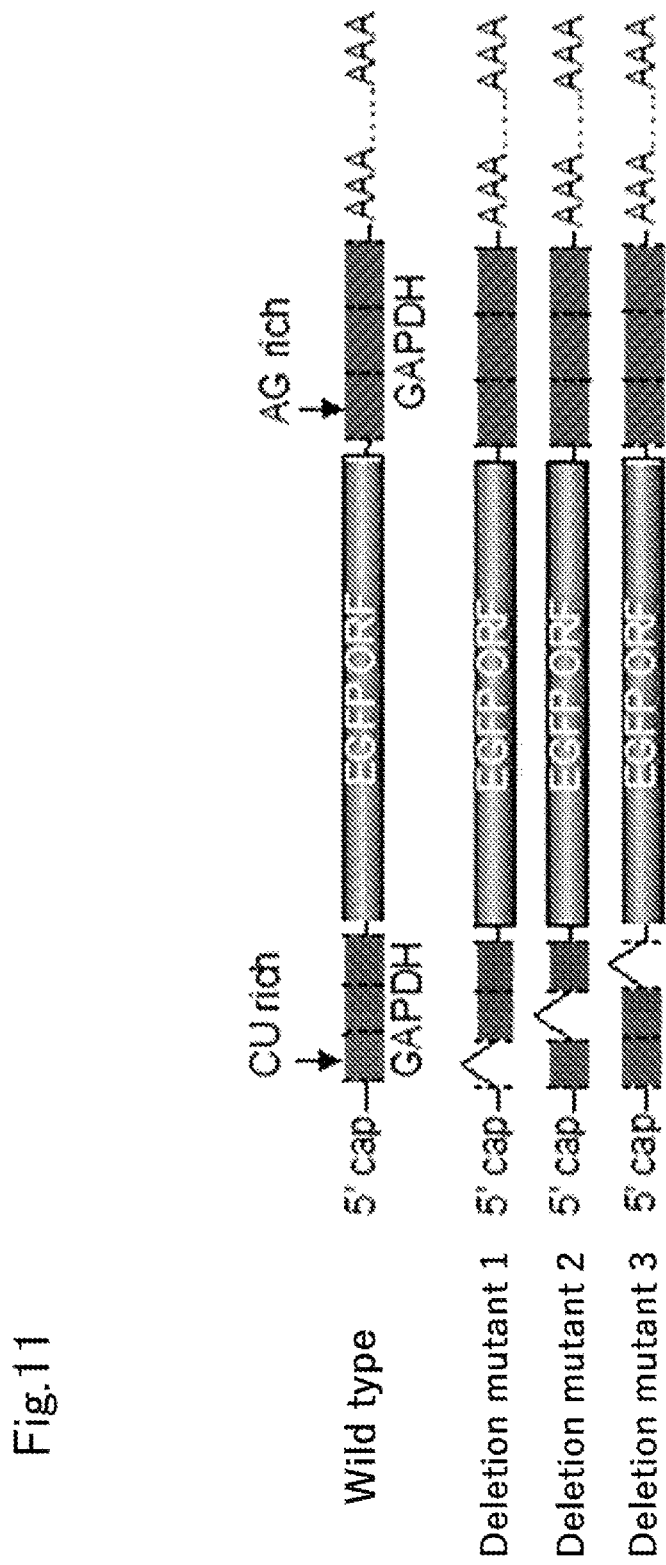
FIG. 11 A view illustrating artificially synthesized mRNAs produced.

FIG. 11 is a view illustrating artificially synthesized mRNAs produced. The artificially synthesized mRNAs illustrated in FIG. 11 are, from top to bottom, artificially synthesized mRNA (hereinafter, also referred to as "wild type") having the 5' UTR sequence of GAPDH and the 3' UTR sequence of GAPDH, an artificially synthesized mRNA (deletion mutant 1) in which, among three portions into which the 5' UTR sequence was divided, a portion located closest to the 5' end side was deleted, an artificially synthesized mRNA (deletion mutant 2) in which, among three portions into which the 5' UTR sequence was divided, a central portion was deleted, and an artificially synthesized mRNA (deletion mutant 3) in which, among three portions into which the 5' UTR sequence was divided, a portion located closest to the 3' end side was deleted. A cap structure is added to the 5' end of the artificially synthesized mRNA used in this experiment, and a 72-base poly-A tail is added to the 3' end thereof. In addition, the ORF, which is the protein coding region of the artificially synthesized mRNAs used in this experiment, has EGFP.

Figure 12:
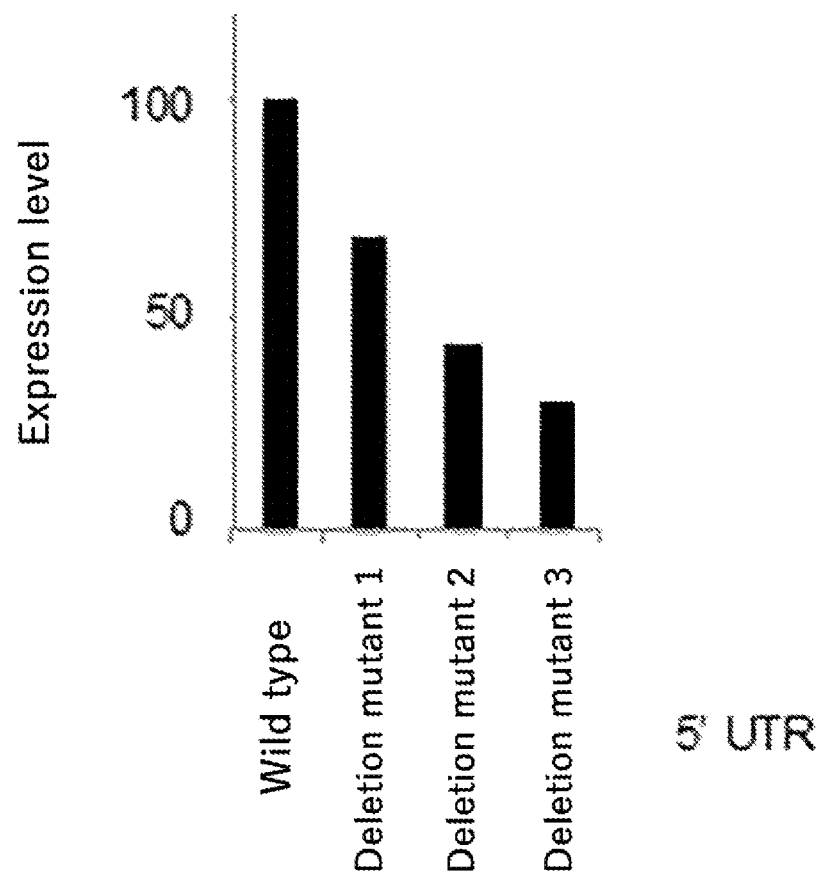
FIG. 12 A view illustrating a difference in expression level caused by the presence or absence of a 5' UTR sequence of GAPDH.

FIG. 12 is a view illustrating a difference in expression level caused by the presence or absence of the 5' UTR sequence of GAPDH. The protein expression levels were measured by introducing the artificially synthesized mRNAs illustrated in FIG. 11 into HeLa cells. FIG. 12 illustrates relative values of the expression levels when the expression level of the wild type is 100.

Figure 13:
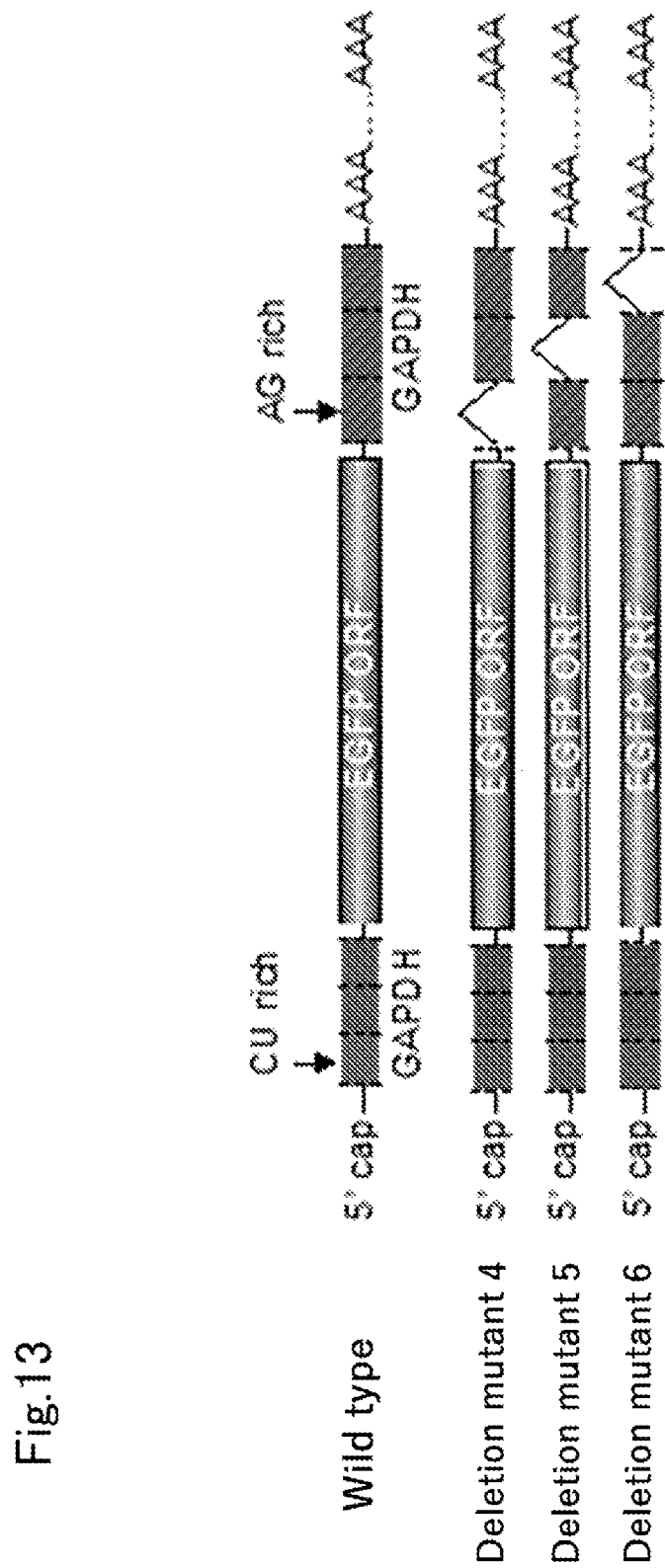
FIG. 13 A view illustrating artificially synthesized mRNAs produced.

FIG. 13 is a view illustrating artificially synthesized mRNAs produced. The artificially synthesized mRNAs illustrated in FIG. 13 are, from top to bottom, artificially synthesized mRNA (wild type) having the 5' UTR sequence of GAPDH and the 3' UTR sequence of GAPDH, an artificially synthesized mRNA (deletion mutant 4) in which, among three portions into which the 3' UTR sequence was divided, a portion located closest to the 5' end side was deleted, an artificially synthesized mRNA (deletion mutant 5) in which, among three portions into which the 3' UTR sequence was divided, a central portion was deleted, and an artificially synthesized mRNA (deletion mutant 6) in which, among three portions into which the 3' UTR sequence was divided, a portion located closest to the 3' end side was deleted. A cap structure is added to the 5' end of the artificially synthesized mRNA used in this experiment, and a 72-base poly-A tail is added to the 3' end thereof. In addition, the ORF, which is the protein coding region of the artificially synthesized mRNAs used in this experiment, has EGFP.

Figure 14:
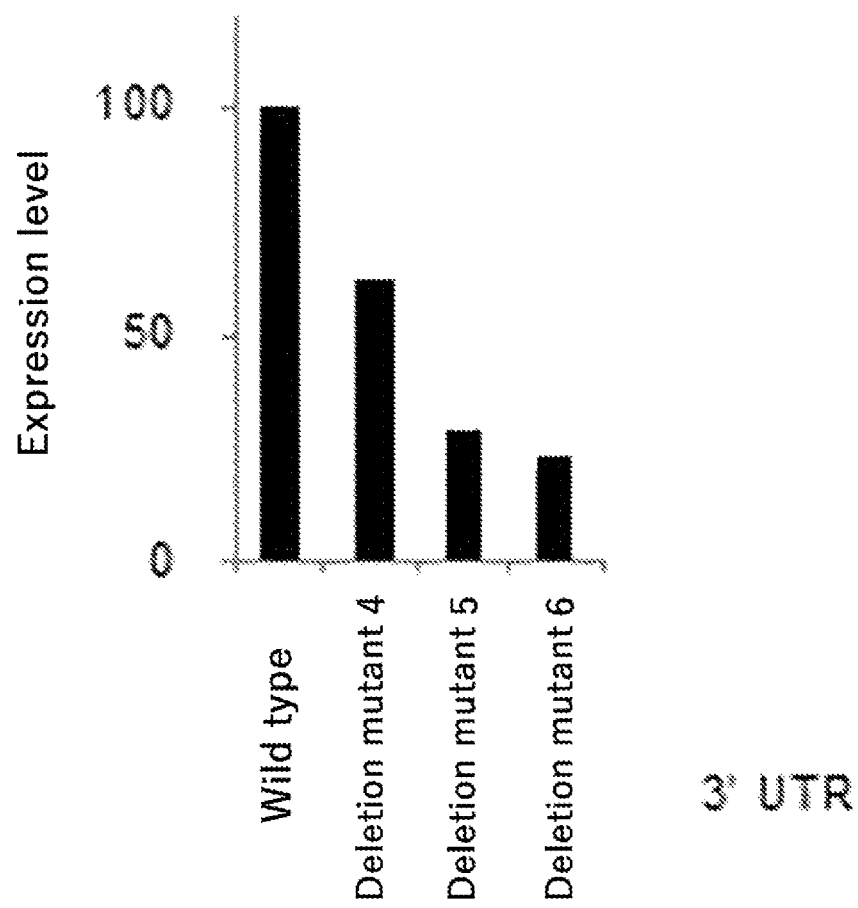
FIG. 14 A view illustrating a difference in expression level caused by the presence or absence of a 3' UTR sequence of GAPDH.

FIG. 14 is a view illustrating a difference in expression level caused by the presence or absence of the 3' UTR sequence of GAPDH. The protein expression levels were measured by introducing the artificially synthesized mRNAs illustrated in FIG. 13 into HeLa cells. FIG. 14 illustrates relative values of the expression levels when the expression level of the wild type is 100.

From the results of FIGS. 12 and 14, it was found that all the deletion mutants were reduced in expression efficiency as compared with the wild-type. From this, it was found that the presence of the entire regions of both the 5'UTR sequence of GAPDH and the 3' UTR sequence of GAPDH contributes to the effect of improving the translation efficiency.

(v) Experiment 5

Figure 15:
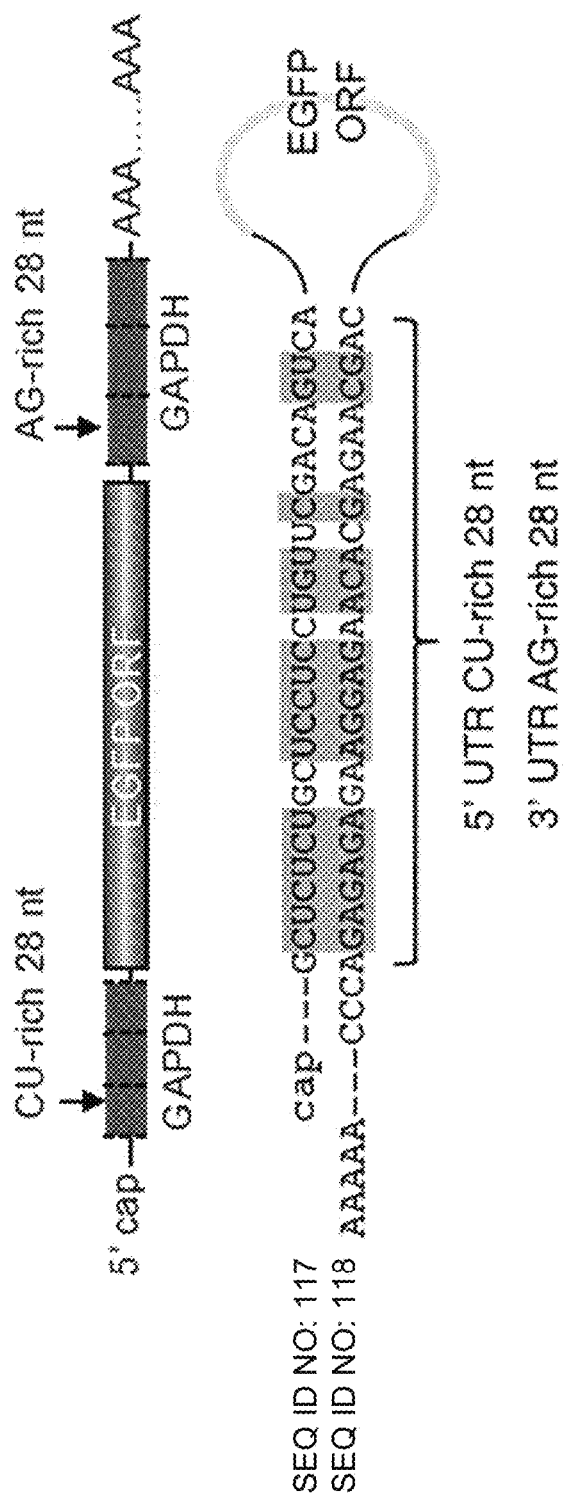
FIG. 15 (SEQ ID NOS: 117 and 118) A view illustrating artificially synthesized mRNAs produced.

FIG. 15 is a view illustrating artificially synthesized mRNAs produced. In general, the 5' UTR sequence of GAPDH (SEQ ID NO: 117) has complementarity to the 3' UTR sequence of GAPDH (SEQ ID NO: 118) over the entire region. In this experiment, artificially synthesized mRNAs having a part of the 5' UTR sequence and a part of the 3' UTR sequence, which were regions having particularly high complementarity to each other, were used. Specifically, as the 5' UTR sequence, there was used a CU-rich region (28 nucleotides) (hereinafter, also referred to as "5' UTR 28 nt"), which was a portion located closest to the 5' end side, among three portions into which the 5' UTR sequence of GAPDH was divided. As the 3' UTR sequence of GAPDH, there was used an AG-rich region (28 nucleotides) (hereinafter, also referred to as "3' UTR 28 nt"), which was a portion located closest to the 5' end side, among three portions into which the 3' UTR sequence of GAPDH was divided.

Figure 16:
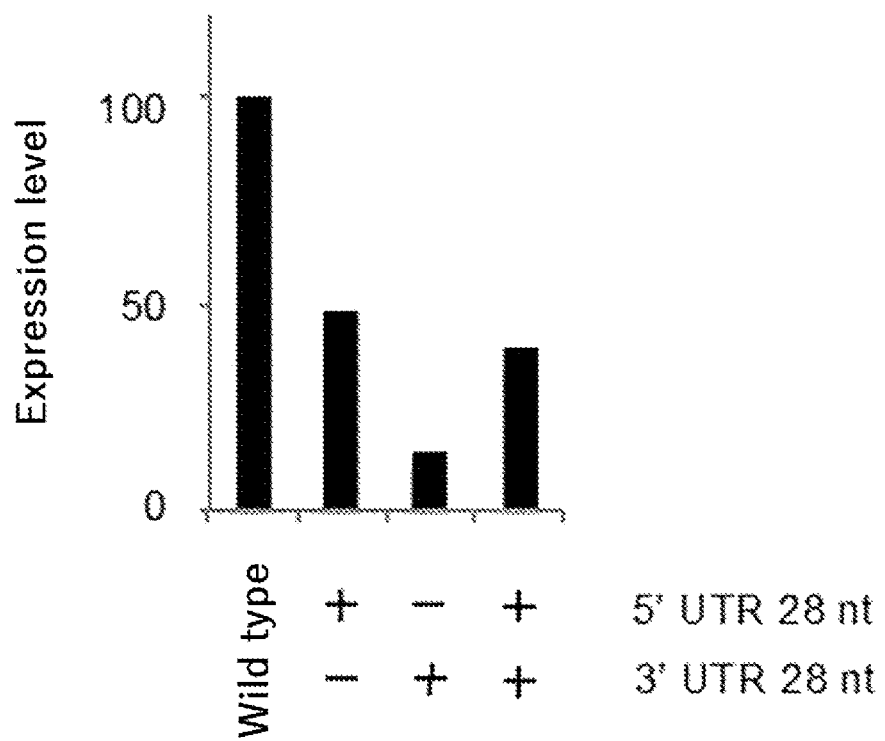
FIG. 16 A view illustrating a difference in expression level due to the presence or absence of 5' UTR 28 nt and 3' UTR 28 nt.

FIG. 16 is a view illustrating a difference in expression level due to the presence or absence of 5' UTR 28 nt and 3' UTR 28 nt. The protein expression levels were measured by introducing the artificially synthesized mRNA into HeLa cells. FIG. 16 illustrates relative values of the expression levels when the expression level of the wild type is 1.

From the results of FIG. 16, it was found that the artificially synthesized mRNAs having at least one of 5' UTR 28 nt and 3' UTR 28 nt were reduced in translation efficiency as compared with the wild type. Also from the results, it was found that the presence of the entire regions of both the 5' UTR sequence of GAPDH and the 3' UTR sequence of GAPDH contributes to the effect of improving the translation efficiency.

(vi) Experiment 6

Figure 17:
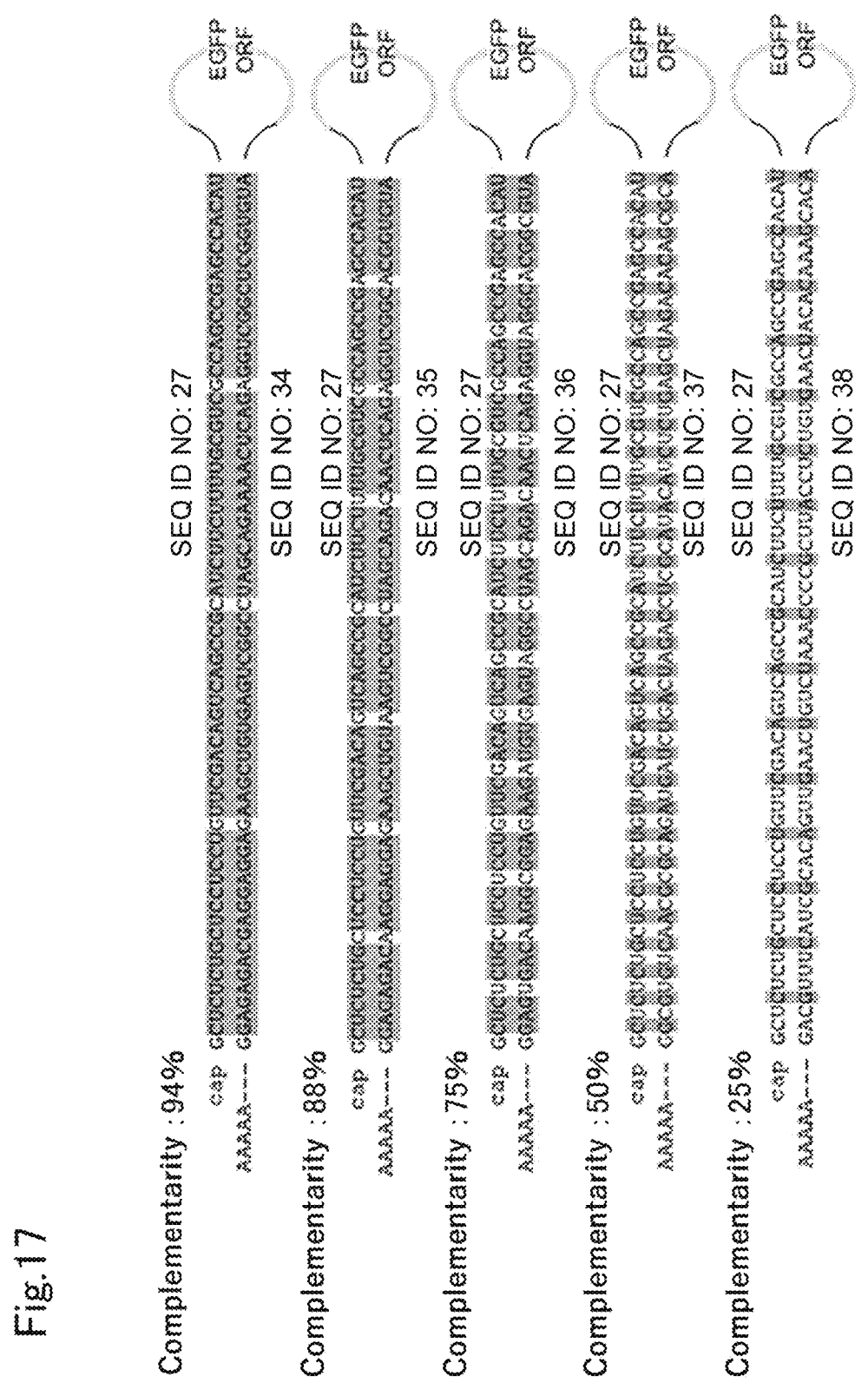

FIG. 17 is a view illustrating artificially synthesized mRNAs produced. In this experiment, artificially synthesized mRNAs having the 5' UTR sequence of GAPDH and having a 3' UTR sequence with predetermined complementarity to the 5' UTR sequence of GAPDH were used. Specifically, the artificially synthesized mRNAs illustrated in FIG. 17 are, from top to bottom, an artificially synthesized mRNA having a 3' UTR sequence with 94% complementarity to the 5' UTR sequence of GAPDH (SEQ ID NOS: 27 and 34), an artificially synthesized mRNA having a 3' UTR sequence with 88% complementarity to the 5' UTR sequence of GAPDH (SEQ ID NOS: 27 and 35), an artificially synthesized mRNA having a 3' UTR sequence with 75% complementarity to the 5' UTR sequence of GAPDH (SEQ ID NOS: 27 and 36), an artificially synthesized mRNA having a 3' UTR sequence with 50% complementarity to the 5' UTR sequence of GAPDH (SEQ ID NOS: 27 and 37), and an artificially synthesized mRNA having a 3' UTR sequence with 25% complementarity to the 5'UTR sequence of GAPDH (SEQ ID NOS: 27 and 38). A cap structure is added to the 5' end of the artificially synthesized mRNA used in this experiment, and a 72-base poly-A tail is added to the 3' end thereof. In addition, the ORF, which is the protein coding region of the artificially synthesized mRNAs used in this experiment, has EGFP.

Figure 18:
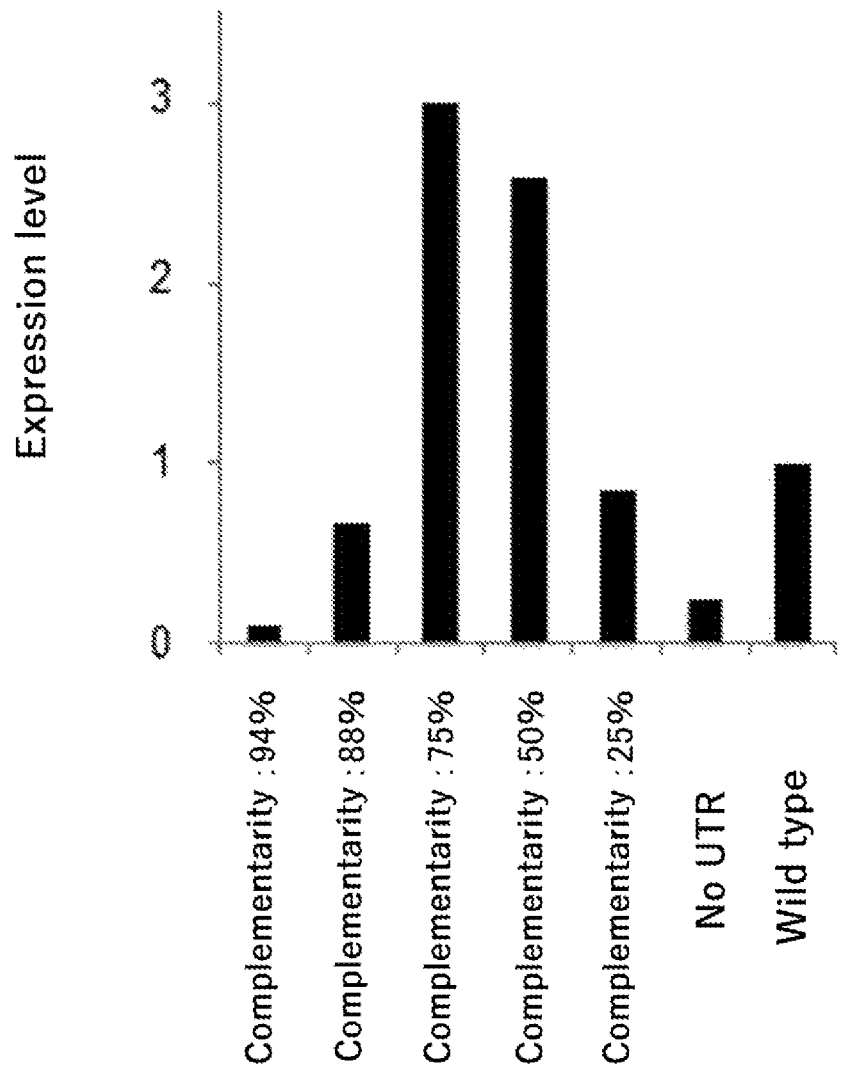
FIG. 18 A view illustrating a difference in expression level due to complementarity.

FIG. 18 is a view illustrating a difference in expression level due to complementarity. The protein expression levels were measured by introducing the artificially synthesized mRNA into HeLa cells. FIG. 18 illustrates relative values of the expression levels when the expression level of the wild type is 1.

From the results of FIG. 18, it was found that the artificially synthesized mRNA having the 3' UTR sequence with 50% complementarity to the 5' UTR sequence of GAPDH and the artificially synthesized mRNA having the 3' UTR sequence with 75% complementarity to the 5' UTR sequence of GAPDH showed a translation efficiency 2.5 times or more higher than that of the wild type.

FIG. 19 is a view illustrating an artificially synthesized mRNA produced. In this experiment, an artificially synthesized mRNA having the 5' UTR sequence of GAPDH and having a 3' UTR sequence with 100% complementarity to the 5' UTR sequence of GAPDH was used (SEQ ID NOS: 27 and 33). A cap structure is added to the 5' end of the artificially synthesized mRNA used in this experiment, and a 72-base poly-A tail is added to the 3' end thereof. In addition, the ORF, which is the protein coding region of the artificially synthesized mRNAs used in this experiment, has EGFP.

Figure 20:
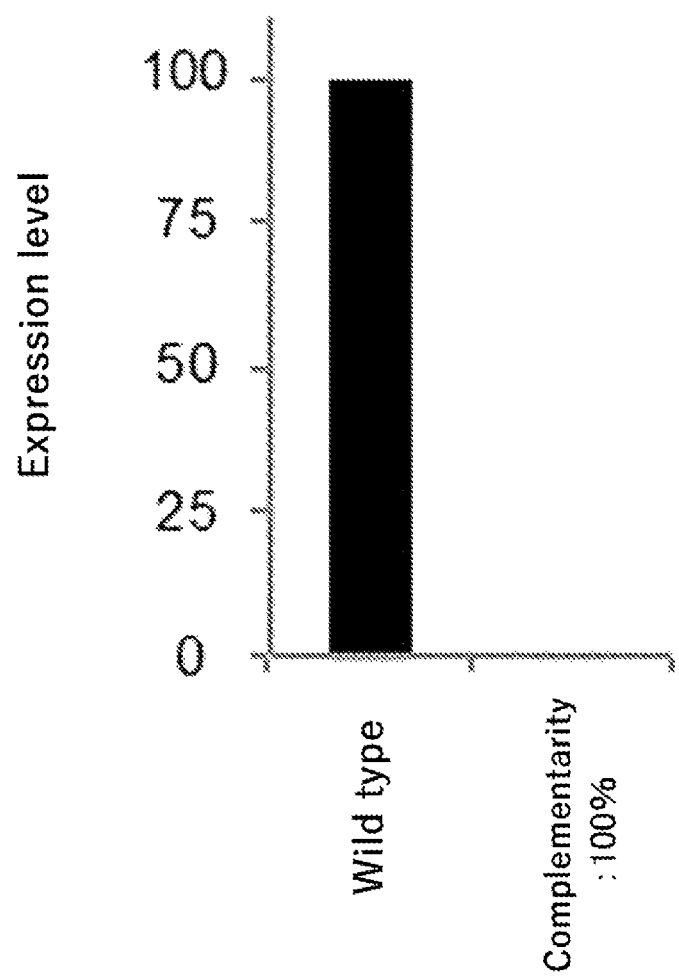
FIG. 20 A view illustrating a difference in expression level due to complementarity.

FIG. 20 is a view illustrating a difference in expression level due to complementarity. The protein expression levels were measured by introducing the artificially synthesized mRNA into HeLa cells. FIG. 20 illustrates a relative value of the expression level when the expression level of the wild type is 100.

From the results of FIG. 20, no protein expression was observed in the artificially synthesized mRNA having the 3' UTR sequence with 100% complementarity to the 5' UTR sequence of GAPDH. From the results, it was found to be important to include a 3' UTR sequence with partial complementarity to the 5' UTR sequence of GAPDH.

(vii) Experiment 7

Figure 21:
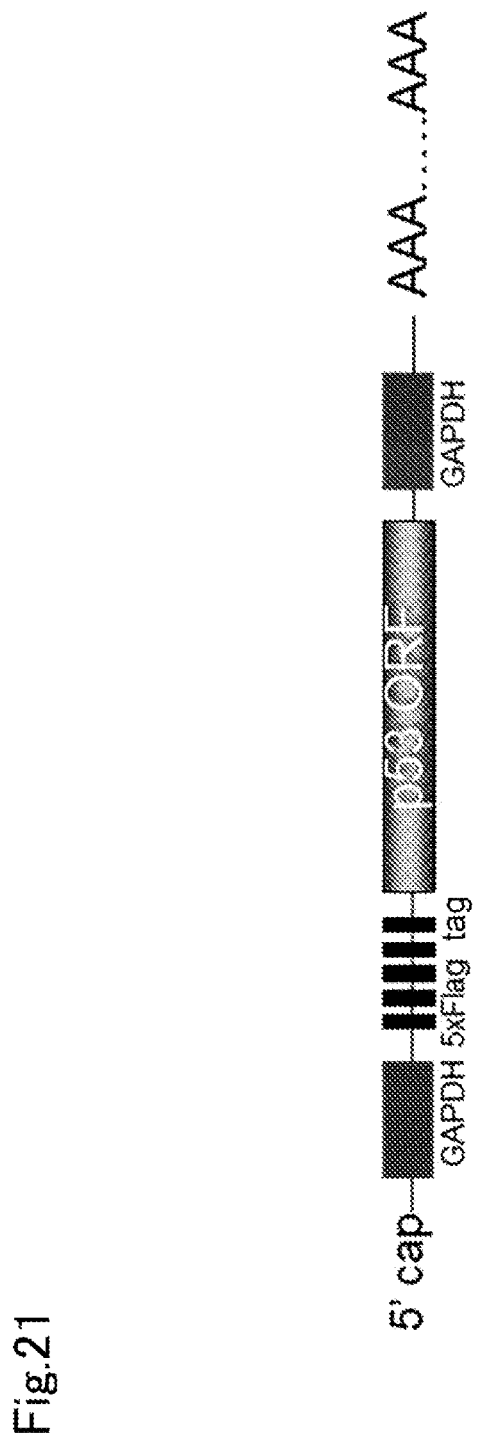
FIG. 21 A view illustrating an artificially synthesized mRNA produced.

FIG. 21 is a view illustrating an artificially synthesized mRNA produced. A cap structure is added to the 5' end of the artificially synthesized mRNA used in this experiment, and a 72-base poly-A tail is added to the 3' end thereof. In addition, for the purpose of practical use, this experiment used an ORF of a cancer suppressor gene p53 as a protein coding region. A 5x Flag tag was added to the ORF.

Figure 22:
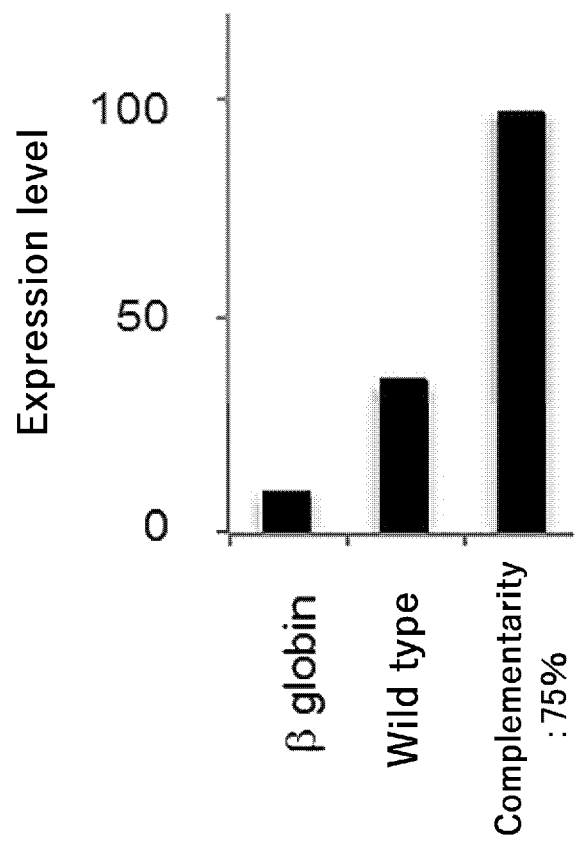
FIG. 22 A view illustrating a difference in expression level when a cancer suppressor gene p53 was used.

FIG. 22 is a view illustrating a difference in expression level when the cancer suppressor gene p53 was used. The protein expression level was measured by introducing the artificially synthesized mRNA into U2OS cells. FIG. 22 shows relative values of the expression levels when the expression level of the artificially synthesized mRNA having the 3' UTR sequence with 75% complementarity to the 5' UTR sequence of GAPDH is 100.

From the results of FIG. 22, it was found that the wild type showed a translation efficiency about 4 times higher than that of the artificially synthesized mRNA having the 3' UTR sequence of B-globin that is standardly used as an artificially synthesized mRNA with a high expression efficiency; and that the artificially synthesized mRNA having the 3' UTR sequence with 75% complementarity to the 5' UTR sequence of GAPDH showed a translation efficiency about 10 times higher than that thereof.

Figure 23:
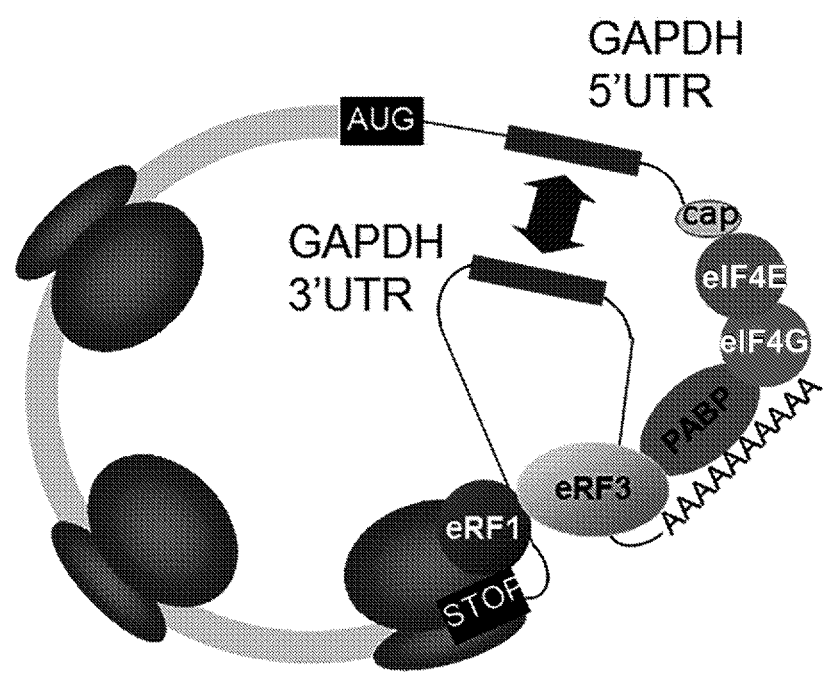
FIG. 23 A view for explaining a mechanism for estimating obtained effects.

FIG. 23 is a view for explaining a mechanism for estimating the obtained effects. The artificially synthesized mRNA of the present embodiment includes a 5' untranslated region of GAPDH and a 3' untranslated region of GAPDH. Alternatively, the artificially synthesized mRNA of the present embodiment includes a 5' untranslated region and a 3' untranslated region having 40% or more and 80% or less complementarity to the 5' untranslated region. In other words, in the artificially synthesized mRNA of the present embodiment, the 3' UTR sequence has partial complementarity to the 5' UTR sequence of GAPDH in any case. It is considered that such partial complementarity promotes circularization of mRNA, thereby efficiently recycling ribosomes, and thus that the translation efficiency is improved.

(viii) Experiment 8

Figure 24:
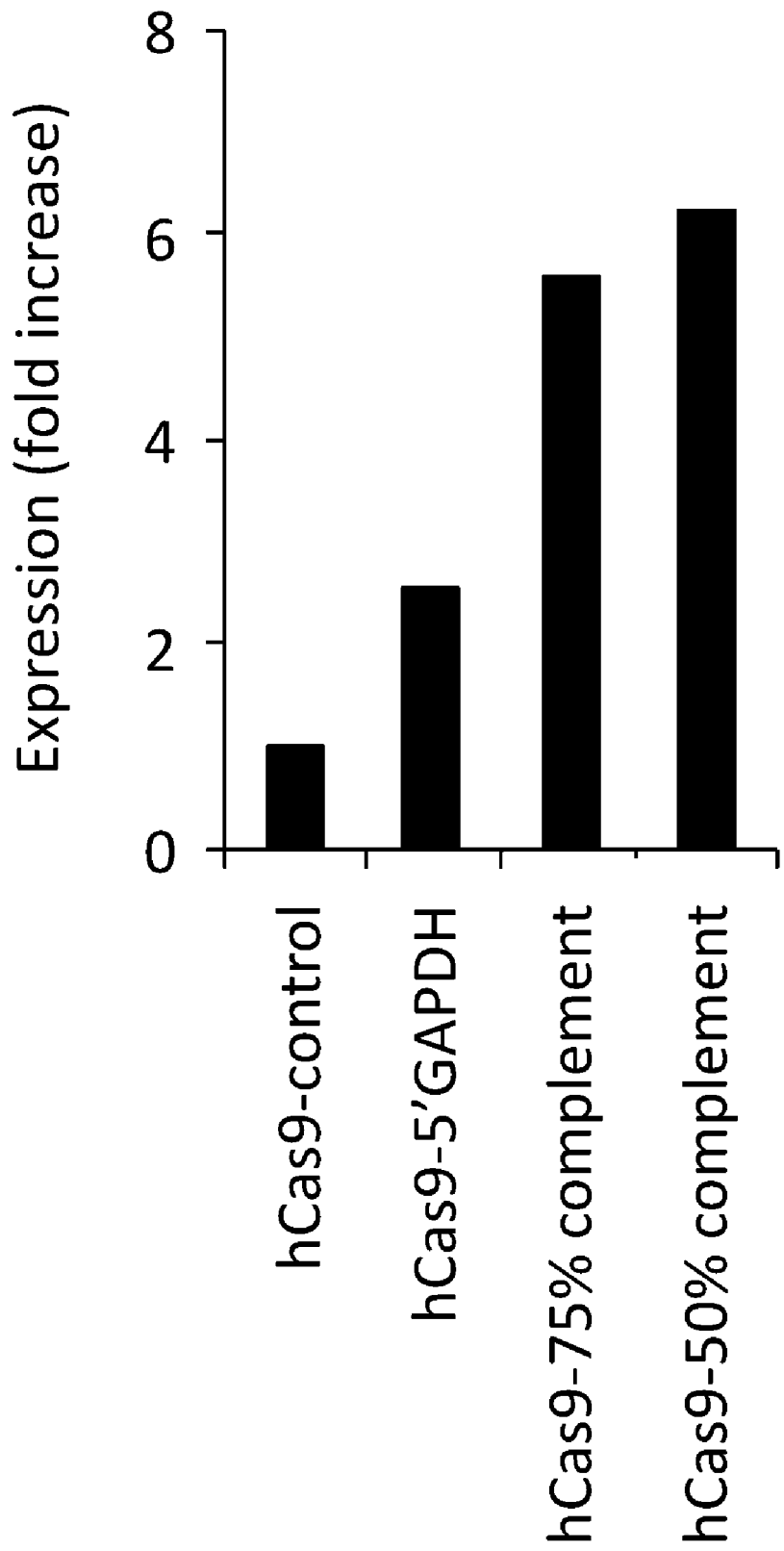
FIG. 24 A view illustrating a difference in expression level when a genome-edited gene hCas9 was used.

FIG. 24 is a view illustrating a difference in expression level when the genome-edited gene hCas9 was used. The vertical axis in the figure represents the expression level (expression (fold increase)). In this experiment, the following mRNAs were used. This figure illustrates relative values of the expression levels when the expression level of the artificially synthesized mRNA having no 5' UTR sequence or 3' UTR sequence is 1.

Genome-edited gene hCas9 having no 5' UTR sequence or 3' UTR sequence (control).

Artificially synthesized mRNA having 5' UTR sequence of GAPDH.

Artificially synthesized mRNA having 5'UTR sequence of GAPDH and 3' UTR sequence with 75% complementarity to the 5' UTR sequence of GAPDH.

Artificially synthesized mRNA having 5'UTR sequence of GAPDH and 3' UTR sequence with 50% complementarity to the 5' UTR sequence of GAPDH From the results of FIG. 24, it was found that the artificially synthesized mRNA having the 5' UTR sequence of GAPDH showed a translation efficiency 2 times or more higher than that of the genome-edited gene hCas9 having no 5' UTR sequence or 3' UTR sequence; and that the artificially synthesized mRNA having the 3' UTR sequence with 75% complementarity to the 5' UTR sequence of GAPDH and the artificially synthesized mRNA having the 3' UTR sequence having the 3' UTR sequence with 50% complementarity to the 5'UTR sequence of GAPDH showed a translation efficiency 5 times or more higher than that thereof.

Figure 25:
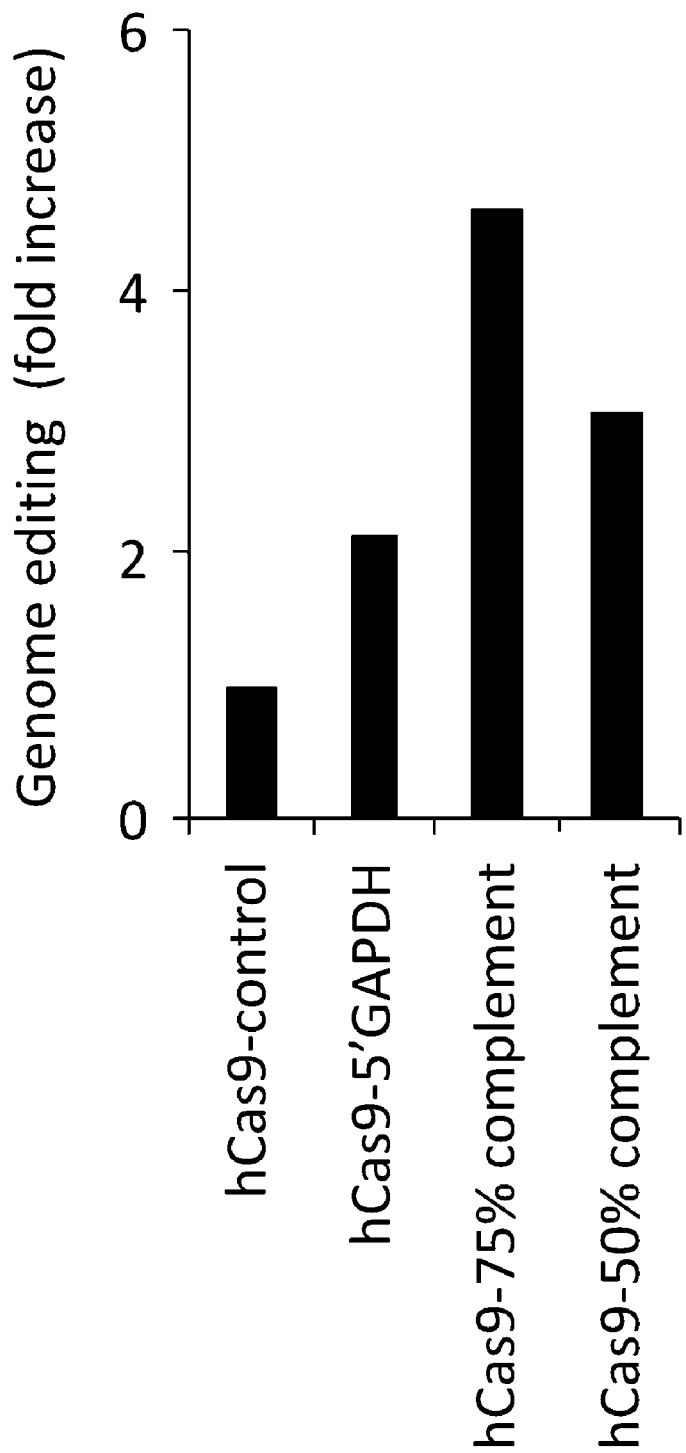
FIG. 25 A view illustrating a difference in genome editing level when the genome-edited gene hCas9 was used.

FIG. 25 is a view illustrating a difference in genome editing level when the genome-edited gene hCas9 was used. The vertical axis of the figure represents the genome editing level (Genome editing (fold increase)). In this experiment, the same mRNAs as in FIG. 24 were used. The figure illustrates relative values of the genome editing levels when the genome editing level of the genome-edited gene hCas9 having no 5' UTR sequence or 3' UTR sequence is 1.

From the results of FIG. 25, it was found that the artificially synthesized mRNA having the 5' UTR sequence of GAPDH showed a genome editing level 2 times or more higher than that of the genome edited gene hCas9 having no 5' UTR sequence or 3' UTR sequence; and that the artificially synthesized mRNA having the 3' UTR sequence with 75% complementarity to the 5' UTR sequence of GAPDH and the artificially synthesized mRNA having the 3' UTR sequence with 50% complementarity to the 5' UTR sequence of GAPDH showed a genome editing level 3 times or more higher than that thereof.

(ix) Experiment 9

Figure 26:
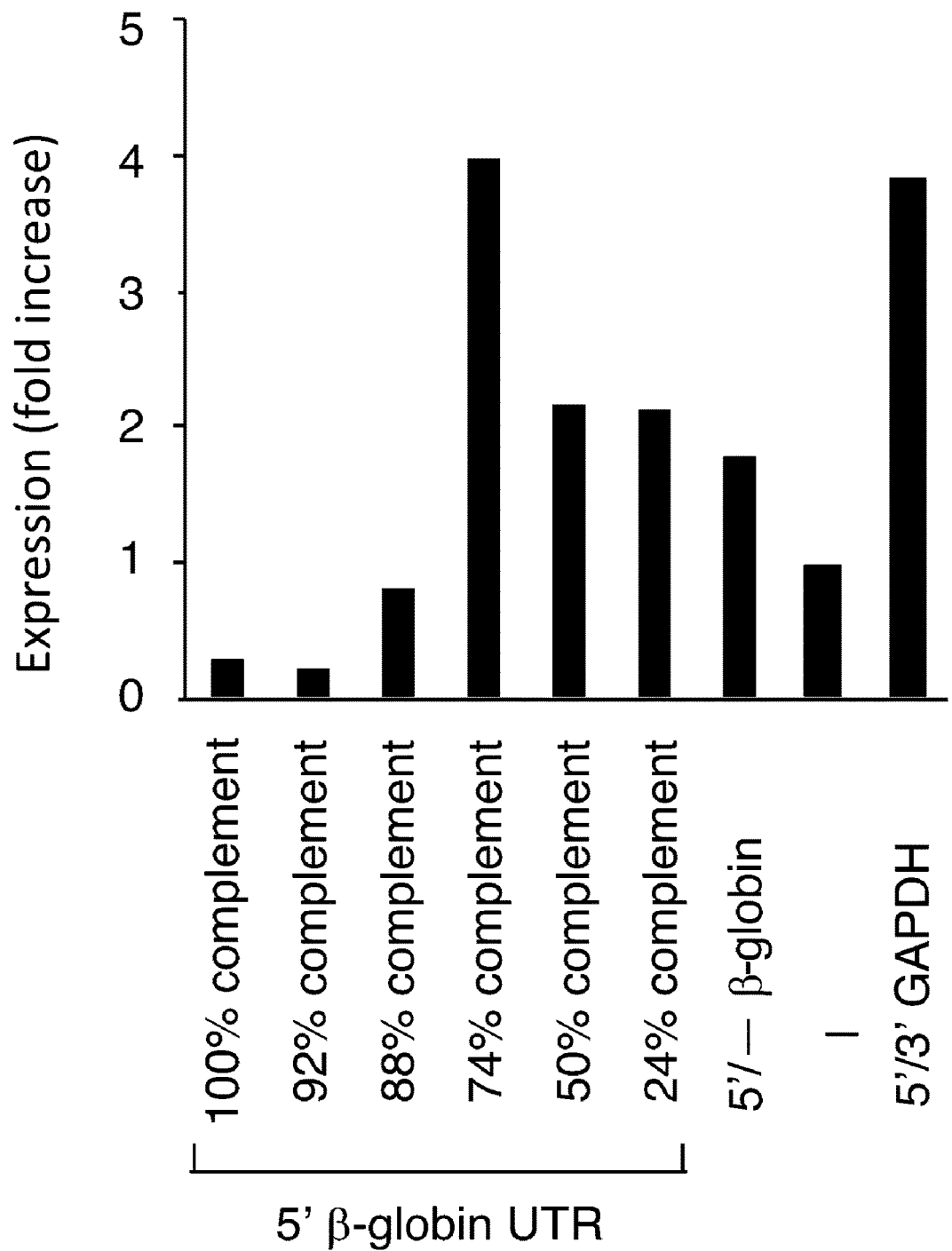
FIG. 26 A view illustrating a difference in expression level when a 5' UTR of B-globin was used.

FIG. 26 is a view illustrating a difference in expression level when the 5' UTR of B-globin was used. The vertical axis in the figure represents the expression level (expression (fold increase)). In this experiment, the following mRNAs were used. This figure illustrates relative values of the expression levels when the expression level of the artificially synthesized mRNA having no 5' UTR sequence or 3' UTR sequence is 1.

Artificially synthesized mRNA having 5' UTR sequence of B-globin and 3' UTR sequence with 100% complementarity to the 5' UTR sequence of 8-globin.

Artificially synthesized mRNA having 5' UTR sequence of B-globin and 3' UTR sequence with 92% complementarity to the 5' UTR sequence of 8-globin Artificially synthesized mRNA having 5' UTR sequence of B-globin and 3' UTR sequence with 88% complementarity to the 5' UTR sequence of 6-globin.

Artificially synthesized mRNA having 5' UTR sequence of B-globin and 3' UTR sequence with 74% complementarity to the 5' UTR sequence of B-globin Artificially synthesized mRNA having 5'UTR sequence of B-globin and 3' UTR sequence with 50% complementarity to the 5' UTR sequence of 8-globin Artificially synthesized mRNA having 5'UTR sequence of B-globin and 3' UTR sequence with 24% complementarity to the 5' UTR sequence of B-globin.

Artificially synthesized mRNA having 5' UTR sequence of B-globin and having no 3' UTR sequence Artificially synthesized mRNA having no 5' UTR sequence or 3' UTR sequence.

Artificially synthesized mRNA having 5' UTR sequence of GAPDH and 3' UTR sequence of GAPDH From the results of FIG. 26, it was found that the artificially synthesized mRNA having the 3' UTR sequence with 74% complementarity to the 5' UTR sequence of B-globin and the artificially synthesized mRNA having the 3' UTR sequence having the 3' UTR sequence with 50% complementarity to the 5' UTR sequence of B-globin showed an excellent translation efficiency.

(x) Experiment 10

Figure 27:
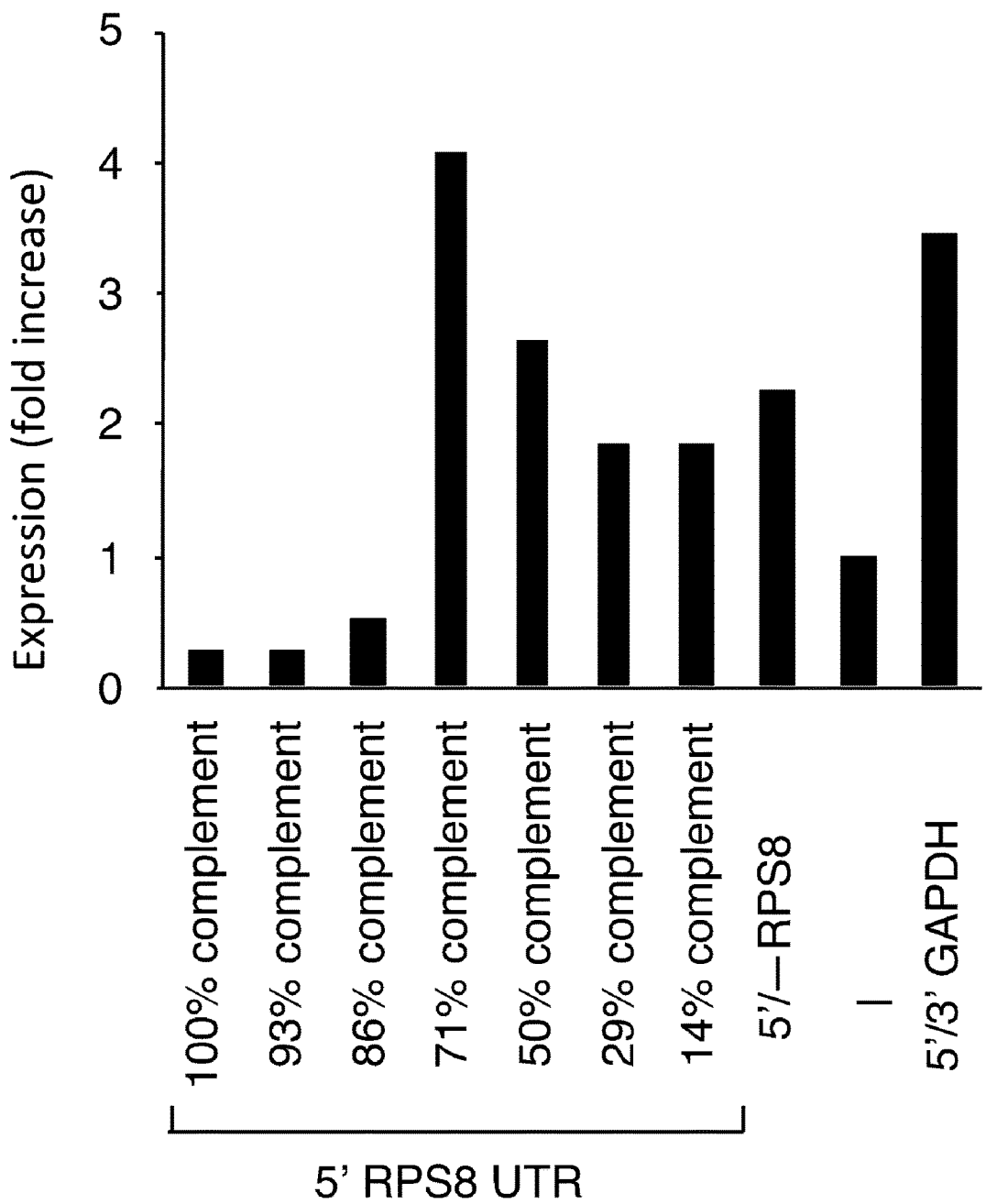
FIG. 27 A view illustrating a difference in expression level when a 5' UTR of RPS8 was used.

FIG. 27 is a view illustrating a difference in expression level when the 5' UTR of RPS8 was used. The vertical axis in the figure represents the expression level (expression (fold increase)). In this experiment, the following mRNAs were used. This figure illustrates relative values of the expression levels when the expression level of the artificially synthesized mRNA having no 5' UTR sequence or 3' UTR sequence is 1.

Artificially synthesized mRNA having 5' UTR sequence of RPS8 and 3' UTR sequence with 100% complementarity to the 5' UTR sequence of RPS8.

Artificially synthesized mRNA having 5' UTR sequence of RPS8 and 3' UTR sequence with 93% complementarity to the 5' UTR sequence of RPS8

Artificially synthesized mRNA having 5' UTR sequence of RPS8 and 3' UTR sequence with 86% complementarity to the 5' UTR sequence of RPS8.

Artificially synthesized mRNA having 5' UTR sequence of RPS8 and 3' UTR sequence with 71% complementarity to the 5' UTR sequence of RPS8.

Artificially synthesized mRNA having 5' UTR sequence of RPS8 and 3' UTR sequence with 50% complementarity to the 5' UTR sequence of RPS8.

Artificially synthesized mRNA having 5' UTR sequence of RPS8 and 3' UTR sequence with 29% complementarity to the 5' UTR sequence of RPS8

Artificially synthesized mRNA having 5' UTR sequence of RPS8 and 3' UTR sequence with 14% complementarity to the 5' UTR sequence of RPS8.

Artificially synthesized mRNA having 5' UTR sequence of RPS8 and having no 3' UTR sequence.

Artificially synthesized mRNA having no 5' UTR sequence or 3' UTR sequence.

Artificially synthesized mRNA having 5'UTR sequence of GAPDH and 3' UTR sequence of GAPDH From the results of FIG. 27, it was found that the artificially synthesized mRNA having the 3' UTR sequence with 71% complementarity to the 5' UTR sequence of RPS8 and the artificially synthesized mRNA having the 3' UTR sequence having the 3' UTR sequence with 50% complementarity to the 5' UTR sequence of RPS8 showed an excellent translation efficiency.

(x) Experiment 10

Figure 28:
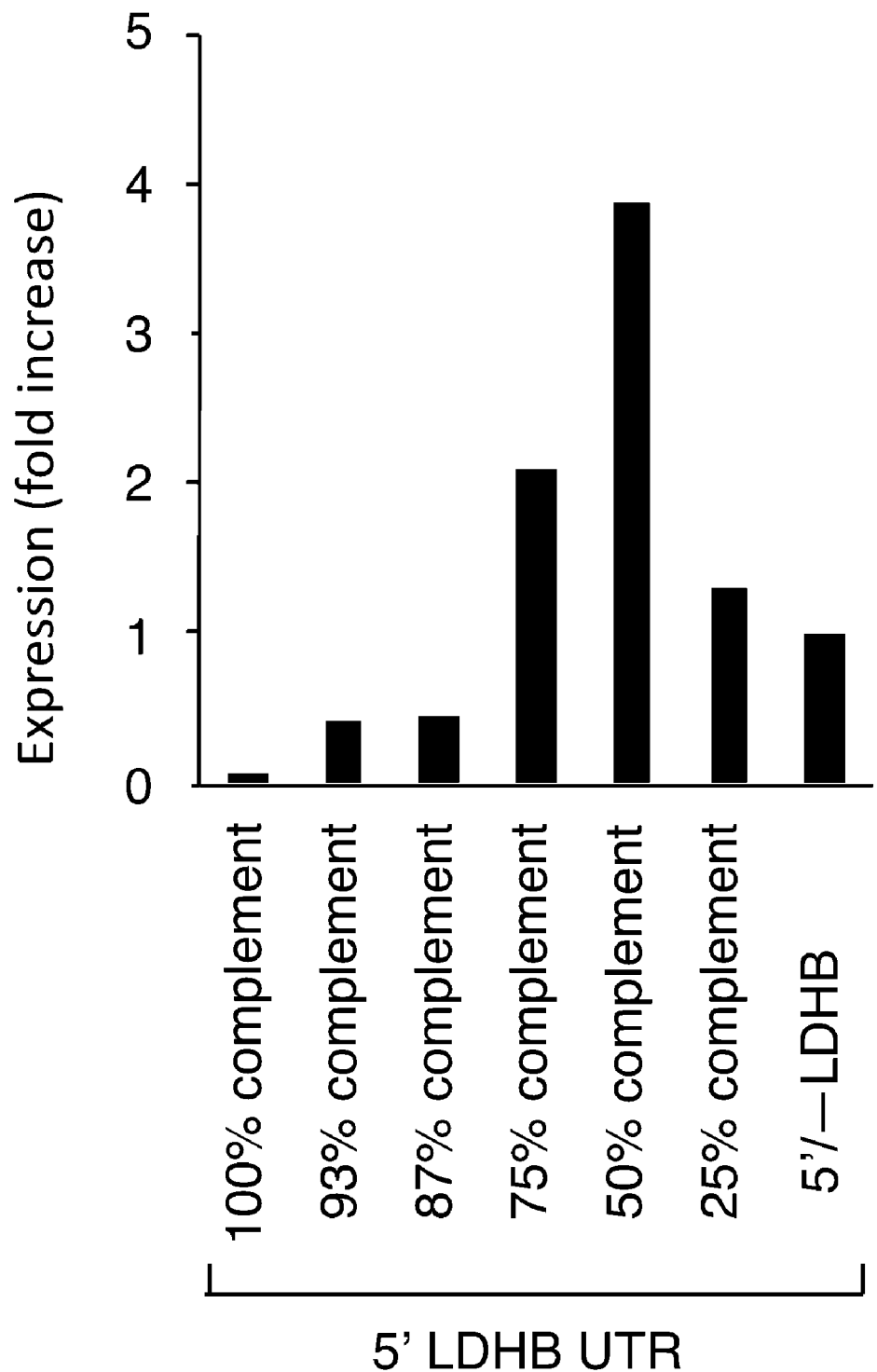
FIG. 28 A view illustrating a difference in expression level when a 5' UTR of LDHB was used.

FIG. 28 is a view illustrating a difference in expression level when the 5' UTR of LDHB was used. The vertical axis in the figure represents the expression level (expression (fold increase)). In this experiment, the following mRNAs were used. This figure illustrates relative values of the expression levels when the expression level of the artificially synthesized mRNA having the 5' UTR sequence of LDHB and having no 3' UTR sequence is 1.

Artificially synthesized mRNA having 5' UTR sequence of LDHB and 3' UTR sequence with 100% complementarity to the 5' UTR sequence of LDHB Artificially synthesized mRNA having 5' UTR sequence of LDHB and 3' UTR sequence with 93% complementarity to the 5' UTR sequence of LDHB.

Artificially synthesized mRNA having 5' UTR sequence of LDHB and 3' UTR sequence with 87% complementarity to the 5' UTR sequence of LDHB Artificially synthesized mRNA having 5' UTR sequence of LDHB and 3' UTR sequence with 75% complementarity to the 5' UTR sequence of LDHB.

Artificially synthesized mRNA having 5' UTR sequence of LDHB and 3' UTR sequence with 50% complementarity to the 5' UTR sequence of LDHB.

Artificially synthesized mRNA having 5' UTR sequence of LDHB and 3' UTR sequence with 25% complementarity to the 5' UTR sequence of LDHB.

Artificially synthesized mRNA having 5' UTR sequence of LDHB and having no 3' UTR sequence From the results of FIG. 28, it was found that the artificially synthesized mRNA having the 3' UTR sequence with 75% complementarity to the 5' UTR sequence of LDHB and the artificially synthesized mRNA having the 3' UTR sequence having the 3' UTR sequence with 50% complementarity to the 5' UTR sequence of LDHB showed an excellent translation efficiency.

INDUSTRIAL APPLICABILITY

According to the present invention, the translation efficiency of the artificially synthesized mRNA introduced into the target cell is improved, and high expression of the gene of interest can be attained. As the applications of the present invention, for example, mRNA medicines (treatment of various viral diseases, cancer immunotherapy, etc.), production of iPS cells, and induction of differentiation of stem cells or progenitor cells are assumed.

The present invention is not limited to the above embodiments and examples of the invention at all. Various modifications are also included in the present invention as long as they can be easily conceived by those skilled in the art without departing from the scope of the claims. The contents of the papers, published patent gazettes, patent gazettes, etc. clarified in the present specification shall be incorporated by reference in their entirety.

The invention claimed is:

1. An artificially synthesized mRNA comprising a 5' untranslated region (5' UTR) of an mRNA encoding a protein, wherein the 5' UTR of comprises SEQ ID NO: 27 and encoding glyceraldehyde-3-phosphate dehydrogenase; and a 3' untranslated region (3' UTR) having 50% or more and 80% or less complementarity to the 5' UTR.

2. The artificially synthesized mRNA according to claim 1, wherein the 3' untranslated region has 50% or more and 75% or less complementarity to the 5' untranslated region.

3. A method comprising the step of introducing the artificially synthesized mRNA according to claim 1 into an isolated cell, wherein said mRNA further comprises a coding region containing a gene of interest located between said 5' untranslated region and said 3' untranslated region and said gene of interest can be expressed in said isolated cell.

4. An isolated cell comprising the artificially synthesized mRNA according to claim 1 introduced thereinto, wherein said mRNA further comprises a coding region containing a gene of interest located between said 5' untranslated region and said 3' untranslated region and said gene of interest can be expressed in said isolated cell.

5. A method for manufacturing an artificially synthesized mRNA, comprising the step of:
    preparing an artificially synthesized mRNA which comprises: a 5' untranslated region (5' UTR) of an mRNA encoding a protein; and a 3' untranslated region (3' UTR) having 50% or more and 80% or less complementarity to the 5' UTR, wherein the 5' UTR comprises SEQ ID NO: 27 and encoding glyceraldehyde-3-phosphate dehydrogenase.

6. A method for manufacturing an artificially synthesized mRNA, comprising the step of:
    preparing an mRNA which comprises a 5' untranslated region (5' UTR) of an mRNA, wherein the 5' UTR comprises SEQ ID NO:27 and encoding glyceraldehyde-3-phosphate dehydrogenase; and a 3' untranslated region (3' UTR) of the mRNA and encoding glyceraldehyde-3-phosphate dehydrogenase.

7. A method comprising the step of:
    introducing an artificially synthesized mRNA comprising a 5' untranslated region (5' UTR) of an mRNA encoding glyceraldehyde-3-phosphate dehydrogenase, wherein the 5' UTR comprises SEQ ID NO:27; and a 3' untranslated region (3' UTR) of the mRNA encoding glyceraldehyde-3-phosphate dehydrogenase into an isolated cell, wherein said mRNA further comprises a coding region containing a gene of interest located between said 5' UTR and said 3' UTR and said gene of interest can be expressed in said isolated cell.

8. An isolated cell comprising an artificially synthesized mRNA comprising a 5' untranslated region (5' UTR) of an mRNA encoding glyceraldehyde-3-phosphate dehydrogenase, wherein the 5' UTR comprises SEQ ID NO:27 and a 3' untranslated region (3' UTR) of the mRNA encoding glyceraldehyde-3-phosphate dehydrogenase introduced thereinto, wherein said mRNA further comprises a coding region containing a gene of interest located between said 5' UTR and said 3' UTR and said gene of interest can be expressed in said isolated cell.

9. The artificially synthesized mRNA according to claim 1, wherein said artificially synthesized mRNA further comprises a coding region located between said 5' UTR and said 3' UTR.

10. The method according to claim 6, wherein said artificially synthesized mRNA further comprises a coding region located between said 5' UTR and said 3' UTR.

11. The method according to claim 10, wherein said coding region contains a gene of interest located between said 5' UTR and said 3' UTR.

* * * * *

SEQUENCE LISTING

```
<160> NUMBER OF SEQ ID NOS: 118

<210> SEQ ID NO 1
<211> LENGTH: 66
<212> TYPE: DNA
<213> ORGANISM: Artificial Sequence
<220> FEATURE:
<223> OTHER INFORMATION: primer

<400> SEQUENCE: 1
cgctctctgc tcctcctgtt cgacagtcag ccgcatcttc ttttgcgtcg ccagccgagc      60
cacatc                                                                66

<210> SEQ ID NO 2
<211> LENGTH: 74
<212> TYPE: DNA
<213> ORGANISM: Artificial Sequence
<220> FEATURE:
<223> OTHER INFORMATION: primer

<400> SEQUENCE: 2
tcgagatgtg gctcggctgg cgacgcaaaa gaagatgcgg ctgactgtcg aacaggagga      60
gcagagagcg gtac                                                       74

<210> SEQ ID NO 3
<211> LENGTH: 27
<212> TYPE: DNA
<213> ORGANISM: Artificial Sequence
<220> FEATURE:
<223> OTHER INFORMATION: primer

<400> SEQUENCE: 3
aaggaattcg acccctggac caccagc                                         27

<210> SEQ ID NO 4
<211> LENGTH: 28
<212> TYPE: DNA
<213> ORGANISM: Artificial Sequence
<220> FEATURE:
<223> OTHER INFORMATION: primer

<400> SEQUENCE: 4
ttttctagaa ctggttgagc acagggta                                        28

<210> SEQ ID NO 5
<211> LENGTH: 30
<212> TYPE: DNA
<213> ORGANISM: Artificial Sequence
<220> FEATURE:
<223> OTHER INFORMATION: primer
```

```
<400> SEQUENCE: 5
ttaggtaccg gtgcgcgggg aggtggaggg                                      30

<210> SEQ ID NO 6
<211> LENGTH: 30
<212> TYPE: DNA
<213> ORGANISM: Artificial Sequence
<220> FEATURE:
<223> OTHER INFORMATION: primer

<400> SEQUENCE: 6
tgcctcgagc ttgcttctcc tgccgccgtc                                      30

<210> SEQ ID NO 7
<211> LENGTH: 30
<212> TYPE: DNA
<213> ORGANISM: Artificial Sequence
<220> FEATURE:
<223> OTHER INFORMATION: primer

<400> SEQUENCE: 7
agggaattca ttgcttaaac tttgaacaac                                      30

<210> SEQ ID NO 8
<211> LENGTH: 30
<212> TYPE: DNA
<213> ORGANISM: Artificial Sequence
<220> FEATURE:
<223> OTHER INFORMATION: primer

<400> SEQUENCE: 8
ttttctagaa atgattgatc tgatgttcct                                      30

<210> SEQ ID NO 9
<211> LENGTH: 30
<212> TYPE: DNA
<213> ORGANISM: Artificial Sequence
<220> FEATURE:
<223> OTHER INFORMATION: primer

<400> SEQUENCE: 9
aacggtaccc ccctcctccc tccttgcaga                                      30

<210> SEQ ID NO 10
<211> LENGTH: 30
<212> TYPE: DNA
<213> ORGANISM: Artificial Sequence
<220> FEATURE:
<223> OTHER INFORMATION: primer

<400> SEQUENCE: 10
agtctcgagt ttgcacagga gagagaaggc                                      30

<210> SEQ ID NO 11
<211> LENGTH: 30
<212> TYPE: DNA
<213> ORGANISM: Artificial Sequence
<220> FEATURE:
<223> OTHER INFORMATION: primer

<400> SEQUENCE: 11
gacgaattcc tagtgagctc taggctgtag                                      30

<210> SEQ ID NO 12
<211> LENGTH: 30
```

```
<212> TYPE: DNA
<213> ORGANISM: Artificial Sequence
<220> FEATURE:
<223> OTHER INFORMATION: primer

<400> SEQUENCE: 12
ttttctagac acactacaat agttaatttt                                         30

<210> SEQ ID NO 13
<211> LENGTH: 68
<212> TYPE: DNA
<213> ORGANISM: Artificial Sequence
<220> FEATURE:
<223> OTHER INFORMATION: primer

<400> SEQUENCE: 13
aattatgtgg ctcggctggc gacgcaaaag aagatgcggc tgactgtcga acaggaggag        60
cagagagc                                                                 68

<210> SEQ ID NO 14
<211> LENGTH: 68
<212> TYPE: DNA
<213> ORGANISM: Artificial Sequence
<220> FEATURE:
<223> OTHER INFORMATION: primer

<400> SEQUENCE: 14
ctaggctctc tgctcctcct gttcgacagt cagccgcatc ttcttttgcg tcgccagccg        60
agccacat                                                                 68

<210> SEQ ID NO 15
<211> LENGTH: 68
<212> TYPE: DNA
<213> ORGANISM: Artificial Sequence
<220> FEATURE:
<223> OTHER INFORMATION: primer

<400> SEQUENCE: 15
aattatgtgg ctcggctggg gacgcaaaag aagatccggc tgactgtcga agaggaggag        60
cagagagg                                                                 68

<210> SEQ ID NO 16
<211> LENGTH: 68
<212> TYPE: DNA
<213> ORGANISM: Artificial Sequence
<220> FEATURE:
<223> OTHER INFORMATION: primer

<400> SEQUENCE: 16
ctagcctctc tgctcctcct cttcgacagt cagccggatc ttcttttgcg tccccagccg        60
agccacat                                                                 68

<210> SEQ ID NO 17
<211> LENGTH: 68
<212> TYPE: DNA
<213> ORGANISM: Artificial Sequence
<220> FEATURE:
<223> OTHER INFORMATION: primer

<400> SEQUENCE: 17
aattatgtgg cacggctggg gacgcaacag aagatccggc tgagtgtcga agaggaggaa        60
cagagagg                                                                 68
```

<210> SEQ ID NO 18
<211> LENGTH: 68
<212> TYPE: DNA
<213> ORGANISM: Artificial Sequence
<220> FEATURE:
<223> OTHER INFORMATION: primer

<400> SEQUENCE: 18
ctagcctctc tgttcctcct cttcgacact cagccggatc ttctgttgcg tccccagccg    60
tgccacat                                                              68

<210> SEQ ID NO 19
<211> LENGTH: 68
<212> TYPE: DNA
<213> ORGANISM: Artificial Sequence
<220> FEATURE:
<223> OTHER INFORMATION: primer

<400> SEQUENCE: 19
aattatgcgg cacggatgga gactcaacag acgatccgga tgagtgtaga agaggcggaa    60
cagtgagg                                                              68

<210> SEQ ID NO 20
<211> LENGTH: 30
<212> TYPE: DNA
<213> ORGANISM: Artificial Sequence
<220> FEATURE:
<223> OTHER INFORMATION:
      CTAGCCTCACTGTTCCGCCTCTTCTACACTCATCCGGATCGTCTGTTGAGTCTCCATCCGTGCCG
      CAT

<400> SEQUENCE: 20
agtctcgagt ttgcacagga gagagaaggc                                      30

<210> SEQ ID NO 21
<211> LENGTH: 68
<212> TYPE: DNA
<213> ORGANISM: Artificial Sequence
<220> FEATURE:
<223> OTHER INFORMATION: primer

<400> SEQUENCE: 21
aattacgcga cacagatcga gtctctacat acgctccaga tcagtctagt agacgcgcaa    60
ctgtgcgg                                                              68

<210> SEQ ID NO 22
<211> LENGTH: 68
<212> TYPE: DNA
<213> ORGANISM: Artificial Sequence
<220> FEATURE:
<223> OTHER INFORMATION: primer

<400> SEQUENCE: 22
ctagccgcac agttgcgcgt ctactagact gatctggagc gtatgtagag actcgatctg    60
tgtcgcgt                                                              68

<210> SEQ ID NO 23
<211> LENGTH: 68
<212> TYPE: DNA
<213> ORGANISM: Artificial Sequence
<220> FEATURE:
<223> OTHER INFORMATION: primer

<400> SEQUENCE: 23

-continued aattacacga aacacatcaa gtgtctccat tcgccccaaa tctgtcaagt tgacacgcta    60
ctttgcag                                                              68

<210> SEQ ID NO 24
<211> LENGTH: 68
<212> TYPE: DNA
<213> ORGANISM: Artificial Sequence
<220> FEATURE:
<223> OTHER INFORMATION: primer

<400> SEQUENCE: 24
ctagctgcaa agtagcgtgt caacttgaca gatttggggc gaatggagac acttgatgtg    60
tttcgtgt                                                              68

<210> SEQ ID NO 25
<211> LENGTH: 28
<212> TYPE: DNA
<213> ORGANISM: Artificial Sequence
<220> FEATURE:
<223> OTHER INFORMATION: primer

<400> SEQUENCE: 25
tgcaagcttt cagtctgagt caggccct                                        28

<210> SEQ ID NO 26
<211> LENGTH: 28
<212> TYPE: DNA
<213> ORGANISM: Artificial Sequence
<220> FEATURE:
<223> OTHER INFORMATION: primer

<400> SEQUENCE: 26
gtcaagctta tggaggagcc gcagtcag                                        28

<210> SEQ ID NO 27
<211> LENGTH: 64
<212> TYPE: RNA
<213> ORGANISM: Homo sapiens

<400> SEQUENCE: 27
gcucucugcu ccuccuguuc gacagucagc cgcaucuucu uuugcgucgc cagccgagcc    60
acau                                                                  64

<210> SEQ ID NO 28
<211> LENGTH: 203
<212> TYPE: RNA
<213> ORGANISM: Homo sapiens

<400> SEQUENCE: 28
gaccccugga ccaccagccc cagcaagagc acaagaggaa gagagagacc cucacugcug    60
gggagucccu gccacacuca gucccccacc acacugaauc uccccuccuc acaguugcca   120
uguagacccc uugaagaggg gaggggccua gggagccgca ccuugucaug uaccaucaau   180
aaaguacccu gugcucaacc agu                                            203

<210> SEQ ID NO 29
<211> LENGTH: 131
<212> TYPE: RNA
<213> ORGANISM: Homo sapiens

<400> SEQUENCE: 29

```
ggugcgcggg gagguggagg gcgaggggcg gggcuaccuc aggucccgcc cgcggcaggc    60
cugugggcug cgaggaggag cuuugccuag cuugcaggca gcgcagggca gacggcggca   120
ggagaagcaa g                                                        131
```

<210> SEQ ID NO 30
<211> LENGTH: 224
<212> TYPE: RNA
<213> ORGANISM: Homo sapiens

<400> SEQUENCE: 30

```
auugcuuaaa cuugaacaa ccucaauuuc uuuuuaaacu aauaaaguac uagguugcaa    60
uaugugaaau cagaggacca aaguacagau ggaaaccauu uccacauca caaaaaccca   120 aguuuacagc uugacuuua cuuuaaugug uaauacucaa cucaagguac aagacaauug   180
cauuuaacau uguuauaaau aaaaggaaca ucagaucaau cauu                   224
```

<210> SEQ ID NO 31
<211> LENGTH: 111
<212> TYPE: RNA
<213> ORGANISM: Homo sapiens

<400> SEQUENCE: 31

```
ccccuccucc cuccuugcag agccggcgcc ggaggagacg cacgcagcug acuuugucuu    60
cuccgcacga cuguuacaga ggucuccaga gccuucucuc uccugugcaa a            111
```

<210> SEQ ID NO 32
<211> LENGTH: 200
<212> TYPE: RNA
<213> ORGANISM: Homo sapiens

<400> SEQUENCE: 32

```
cuagugagcu cuaggcugua gaaauuuaaa aacuacaaug ugauuaacuc gagccuuuag    60
uuuucaucca guacaugga ucacaguuug cuuugaucuu cuucaauaug ugaauuuggg   120
cucacagaau caaagccuau gcuugguuua augcuugcaa ucgagcucu ugaacaaaua   180 aaauuaacua uuguagugug                                              200
```

<210> SEQ ID NO 33
<211> LENGTH: 64
<212> TYPE: RNA
<213> ORGANISM: Homo sapiens

<400> SEQUENCE: 33

```
auguggcucg gcuggcgacg caaaagaaga ugcggcugac ugucgaacag gaggagcaga    60
gagc                                                                64
```

<210> SEQ ID NO 34
<211> LENGTH: 64
<212> TYPE: RNA
<213> ORGANISM: Homo sapiens

<400> SEQUENCE: 34

```
auguggcucg gcuggggacg caaaagaaga uccggcugac ugucgaagag gaggagcaga    60
gagg                                                                64
```

<210> SEQ ID NO 35
<211> LENGTH: 64
<212> TYPE: RNA
<213> ORGANISM: Homo sapiens

<400> SEQUENCE: 35
auguggcacg gcuggggacg caacagaaga uccggcugag ugucgaagag gaggaacaga    60
gagg                                                                 64

<210> SEQ ID NO 36
<211> LENGTH: 64
<212> TYPE: RNA
<213> ORGANISM: Homo sapiens

<400> SEQUENCE: 36
augcggcacg gauggagacu caacagacga uccggaugag uguagaagag gcggaacagu    60
gagg                                                                 64

<210> SEQ ID NO 37
<211> LENGTH: 64
<212> TYPE: RNA
<213> ORGANISM: Homo sapiens

<400> SEQUENCE: 37
acgcgacaca gaucgagucu cuacauacgc uccagaucag ucuaguagac gcgcaacugu    60
gcgg                                                                 64

<210> SEQ ID NO 38
<211> LENGTH: 64
<212> TYPE: RNA
<213> ORGANISM: Homo sapiens

<400> SEQUENCE: 38
acacgaaaca caucaagugu cuccauucgc cccaaaucug ucaaguugac acgcuacuuu    60
gcag                                                                 64

<210> SEQ ID NO 39
<211> LENGTH: 1182
<212> TYPE: DNA
<213> ORGANISM: Homo sapiens

<400> SEQUENCE: 39
atggaggagc cgcagtcaga tcctagcgtc gagccccctc tgagtcagga aacattttca    60
gacctatgga aactacttcc tgaaaacaac gttctgtccc ccttgccgtc ccaagcaatg   120
gatgatttga tgctgtcccc ggacgatatt gaacaatggt tcactgaaga cccaggtcca   180
gatgaagctc ccagaatgcc agaggctgct cccccgtgg ccctgcacc agcagctcct   240 acaccggcgg cccctgcacc agccccctcc tggcccctgt catcttctgt cccttcccag   300
aaaacctacc agggcagcta cggtttccgt ctgggcttct tgcattctgg gacagccaag   360
tctgtgactt gcacgtactc ccctgccctc aacaagatgt ttgccaact ggccaagacc   420 tgccctgtgc agctgtgggt tgattccaca ccccgcccg caccgcgt ccgcgccatg   480 gccatctaca gcagtcaca gcacatgacg gaggttgtga ggcgctgccc ccaccatgag   540
cgctgctcag atagcgatgg tctggcccct cctcagcatc ttatccgagt ggaaggaaat   600
ttgcgtgtga agtatttgga tgacagaaac acttttcgac atagtgtggt ggtgccctat   660
gagccgcctg aggttggctc tgactgtacc accatccact acaactacat gtgtaacagt   720
tcctgcatgg gcggcatgaa ccggaggccc atcctcacca tcatcacact ggaagactcc   780
agtggtaatc tactgggacg gaacagcttt gaggtgcgtg tttgtgcctg tcctgggaga   840

```
gaccggcgca cagaggaaga gaatctccgc aagaaggggg agcctcacca cgagctgccc    900
ccagggagca ctaagcgagc actgcccaac aacaccagct cctctcccca gccaaagaag    960
aaaccactgg atggagaata tttcacccct cagatccgtg ggcgtgagcg cttcgagatg   1020
ttccgagagc tgaatgaggc cttggaactc aaggatgccc aggctgggaa ggagccaggg   1080
gggagcaggg ctcactccag ccacctgaag tccaaaaagg gtcagtctac ctcccgccat   1140
aaaaaactca tgttcaagac agaagggcct gactcagact ga                       1182
```

<210> SEQ ID NO 40
<211> LENGTH: 393
<212> TYPE: PRT
<213> ORGANISM: Homo sapiens

<400> SEQUENCE: 40

```
Met Glu Glu Pro Gln Ser Asp Pro Ser Val Glu Pro Pro Leu Ser Gln
1               5                   10                  15

Glu Thr Phe Ser Asp Leu Trp Lys Leu Leu Pro Glu Asn Asn Val Leu
            20                  25                  30

Ser Pro Leu Pro Ser Gln Ala Met Asp Asp Leu Met Leu Ser Pro Asp
        35                  40                  45

Asp Ile Glu Gln Trp Phe Thr Glu Asp Pro Gly Pro Asp Glu Ala Pro
    50                  55                  60

Arg Met Pro Glu Ala Ala Pro Pro Val Ala Pro Ala Pro Ala Ala Pro
65                  70                  75                  80

Thr Pro Ala Ala Pro Ala Pro Ala Pro Ser Trp Pro Leu Ser Ser Ser
                85                  90                  95

Val Pro Ser Gln Lys Thr Tyr Gln Gly Ser Tyr Gly Phe Arg Leu Gly
            100                 105                 110

Phe Leu His Ser Gly Thr Ala Lys Ser Val Thr Cys Thr Tyr Ser Pro
        115                 120                 125

Ala Leu Asn Lys Met Phe Cys Gln Leu Ala Lys Thr Cys Pro Val Gln
    130                 135                 140

Leu Trp Val Asp Ser Thr Pro Pro Pro Gly Thr Arg Val Arg Ala Met
145                 150                 155                 160

Ala Ile Tyr Lys Gln Ser Gln His Met Thr Glu Val Val Arg Arg Cys
                165                 170                 175

Pro His His Glu Arg Cys Ser Asp Ser Asp Gly Leu Ala Pro Pro Gln
            180                 185                 190

His Leu Ile Arg Val Glu Gly Asn Leu Arg Val Glu Tyr Leu Asp Asp
        195                 200                 205

Arg Asn Thr Phe Arg His Ser Val Val Val Pro Tyr Glu Pro Pro Glu
    210                 215                 220

Val Gly Ser Asp Cys Thr Thr Ile His Tyr Asn Tyr Met Cys Asn Ser
225                 230                 235                 240

Ser Cys Met Gly Gly Met Asn Arg Arg Pro Ile Leu Thr Ile Ile Thr
                245                 250                 255

Leu Glu Asp Ser Ser Gly Asn Leu Leu Gly Arg Asn Ser Phe Glu Val
            260                 265                 270

Arg Val Cys Ala Cys Pro Gly Arg Asp Arg Arg Thr Glu Glu Glu Asn
        275                 280                 285

Leu Arg Lys Lys Gly Glu Pro His His Glu Leu Pro Pro Gly Ser Thr
    290                 295                 300

Lys Arg Ala Leu Pro Asn Asn Thr Ser Ser Ser Pro Gln Pro Lys Lys
305                 310                 315                 320
```

```
Lys Pro Leu Asp Gly Glu Tyr Phe Thr Leu Gln Ile Arg Gly Arg Glu
                325                 330                 335
Arg Phe Glu Met Phe Arg Glu Leu Asn Glu Ala Leu Glu Leu Lys Asp
            340                 345                 350
Ala Gln Ala Gly Lys Glu Pro Gly Gly Ser Arg Ala His Ser Ser His
        355                 360                 365
Leu Lys Ser Lys Lys Gly Gln Ser Thr Ser Arg His Lys Lys Leu Met
    370                 375                 380
Phe Lys Thr Glu Gly Pro Asp Ser Asp
385                 390

<210> SEQ ID NO 41
<211> LENGTH: 50
<212> TYPE: DNA
<213> ORGANISM: Artificial Sequence
<220> FEATURE:
<223> OTHER INFORMATION: primer

<400> SEQUENCE: 41
acatttgctt ctgacacaac tgtgttcact agcaacctca aacagacacc              50

<210> SEQ ID NO 42
<211> LENGTH: 58
<212> TYPE: DNA
<213> ORGANISM: Artificial Sequence
<220> FEATURE:
<223> OTHER INFORMATION: primer

<400> SEQUENCE: 42
tcgaggtgtc tgtttgaggt tgctagtgaa cacagttgtg tcagaagcaa atgtgtac    58

<210> SEQ ID NO 43
<211> LENGTH: 54
<212> TYPE: DNA
<213> ORGANISM: Artificial Sequence
<220> FEATURE:
<223> OTHER INFORMATION: primer

<400> SEQUENCE: 43
aattggtgtc tgtttgaggt tgctagtgaa cacagttgtg tcagaagcaa atgt        54

<210> SEQ ID NO 44
<211> LENGTH: 54
<212> TYPE: DNA
<213> ORGANISM: Artificial Sequence
<220> FEATURE:
<223> OTHER INFORMATION: primer

<400> SEQUENCE: 44
ctagacattt gcttctgaca caactgtgtt cactagcaac ctcaaacaga cacc        54

<210> SEQ ID NO 45
<211> LENGTH: 54
<212> TYPE: DNA
<213> ORGANISM: Artificial Sequence
<220> FEATURE:
<223> OTHER INFORMATION: primer

<400> SEQUENCE: 45
aattgctgtc tgtttgaggt tactagtgaa cacagttctg tcagaagcaa atgc        54

<210> SEQ ID NO 46
<211> LENGTH: 54
```

<212> TYPE: DNA
<213> ORGANISM: Artificial Sequence
<220> FEATURE:
<223> OTHER INFORMATION: primer

<400> SEQUENCE: 46
ctaggcattt gcttctgaca gaactgtgtt cactagtaac ctcaaacaga cagc      54

<210> SEQ ID NO 47
<211> LENGTH: 54
<212> TYPE: DNA
<213> ORGANISM: Artificial Sequence
<220> FEATURE:
<223> OTHER INFORMATION: primer

<400> SEQUENCE: 47
aattgctgtc tgtgtgaggt tactagtgat cacagttctg tcagacgcaa atgc      54

<210> SEQ ID NO 48
<211> LENGTH: 54
<212> TYPE: DNA
<213> ORGANISM: Artificial Sequence
<220> FEATURE:
<223> OTHER INFORMATION: primer

<400> SEQUENCE: 48
ctaggcattt gcgtctgaca gaactgtgat cactagtaac ctcacacaga cagc      54

<210> SEQ ID NO 49
<211> LENGTH: 54
<212> TYPE: DNA
<213> ORGANISM: Artificial Sequence
<220> FEATURE:
<223> OTHER INFORMATION: primer

<400> SEQUENCE: 49
aattgctgta tgtgtgatgt tactactgat caccgttctg taagacgcac atgc      54

<210> SEQ ID NO 50
<211> LENGTH: 54
<212> TYPE: DNA
<213> ORGANISM: Artificial Sequence
<220> FEATURE:
<223> OTHER INFORMATION: primer

<400> SEQUENCE: 50
ctaggcatgt gcgtcttaca gaacggtgat cagtagtaac atcacacata cagc      54

<210> SEQ ID NO 51
<211> LENGTH: 54
<212> TYPE: DNA
<213> ORGANISM: Artificial Sequence
<220> FEATURE:
<223> OTHER INFORMATION: primer

<400> SEQUENCE: 51
aattgctata tctgtcatgc tacgactcat ctccgatctc taacacggac acgc      54

<210> SEQ ID NO 52
<211> LENGTH: 54
<212> TYPE: DNA
<213> ORGANISM: Artificial Sequence
<220> FEATURE:
<223> OTHER INFORMATION: primer

<400> SEQUENCE: 52

```
ctaggcgtgt ccgtgttaga gatcggagat gagtcgtagc atgacagata tagc         54
```

<210> SEQ ID NO 53
<211> LENGTH: 54
<212> TYPE: DNA
<213> ORGANISM: Artificial Sequence
<220> FEATURE:
<223> OTHER INFORMATION: primer

<400> SEQUENCE: 53

```
aattgctaga tcagtcttgc aacgcctcat ctgcgagctc gaactcggtc actc         54
```

<210> SEQ ID NO 54
<211> LENGTH: 54
<212> TYPE: DNA
<213> ORGANISM: Artificial Sequence
<220> FEATURE:
<223> OTHER INFORMATION: primer

<400> SEQUENCE: 54

```
ctaggagtga ccgagttcga gctcgcagat gaggcgttgc aagactgatc tagc         54
```

<210> SEQ ID NO 55
<211> LENGTH: 57
<212> TYPE: DNA
<213> ORGANISM: Artificial Sequence
<220> FEATURE:
<223> OTHER INFORMATION: primer

<400> SEQUENCE: 55

```
gttttacaaa ccgaaccgtg aatctttgcg gtttctcttt ccagccagcg ccgagcg      57
```

<210> SEQ ID NO 56
<211> LENGTH: 65
<212> TYPE: DNA
<213> ORGANISM: Artificial Sequence
<220> FEATURE:
<223> OTHER INFORMATION: primer

<400> SEQUENCE: 56

```
tcgacgctcg gcgctggctg gaaagagaaa ccgcaaagat tcacggttcg gtttgtaaaa   60
cgtac                                                               65
```

<210> SEQ ID NO 57
<211> LENGTH: 60
<212> TYPE: DNA
<213> ORGANISM: Artificial Sequence
<220> FEATURE:
<223> OTHER INFORMATION: primer

<400> SEQUENCE: 57

```
aattcgctcg gcgctggctg gaaagagaaa ccgcaaagat tcacggttcg gtttgtaaaa   60
```

<210> SEQ ID NO 58
<211> LENGTH: 60
<212> TYPE: DNA
<213> ORGANISM: Artificial Sequence
<220> FEATURE:
<223> OTHER INFORMATION: primer

<400> SEQUENCE: 58

```
ctagttttac aaaccgaacc gtgaatcttt gcggtttctc tttccagcca gcgccgagcg   60
```

<210> SEQ ID NO 59
<211> LENGTH: 60

```
<212> TYPE: DNA
<213> ORGANISM: Artificial Sequence
<220> FEATURE:
<223> OTHER INFORMATION: primer

<400> SEQUENCE: 59
aattagctcg gcgctggcag gaaagagaaa cctcaaagat tcacggctcg gtttgtaaaa    60

<210> SEQ ID NO 60
<211> LENGTH: 60
<212> TYPE: DNA
<213> ORGANISM: Artificial Sequence
<220> FEATURE:
<223> OTHER INFORMATION: primer

<400> SEQUENCE: 60
ctagttttac aaaccgagcc gtgaatcttt gaggtttctc tttcctgcca gcgccgagct    60

<210> SEQ ID NO 61
<211> LENGTH: 60
<212> TYPE: DNA
<213> ORGANISM: Artificial Sequence
<220> FEATURE:
<223> OTHER INFORMATION: primer

<400> SEQUENCE: 61
aattagctcg gagctggcag gaaagcgaaa cctcaaagac tcacggctcg gttcgtaaaa    60

<210> SEQ ID NO 62
<211> LENGTH: 60
<212> TYPE: DNA
<213> ORGANISM: Artificial Sequence
<220> FEATURE:
<223> OTHER INFORMATION: primer

<400> SEQUENCE: 62
ctagttttac gaaccgagcc gtgagtcttt gaggtttcgc tttcctgcca gctccgagct    60

<210> SEQ ID NO 63
<211> LENGTH: 60
<212> TYPE: DNA
<213> ORGANISM: Artificial Sequence
<220> FEATURE:
<223> OTHER INFORMATION: primer

<400> SEQUENCE: 63
aattagctgg gagcttgcag gatagcgaat cctcaatgac tcaaggctcg cttcgtacaa    60

<210> SEQ ID NO 64
<211> LENGTH: 60
<212> TYPE: DNA
<213> ORGANISM: Artificial Sequence
<220> FEATURE:
<223> OTHER INFORMATION: primer

<400> SEQUENCE: 64
ctagttgtac gaagcgagcc ttgagtcatt gaggattcgc tatcctgcaa gctcccagct    60

<210> SEQ ID NO 65
<211> LENGTH: 60
<212> TYPE: DNA
<213> ORGANISM: Artificial Sequence
<220> FEATURE:
<223> OTHER INFORMATION: primer

<400> SEQUENCE: 65
```
aattagatgt gagattgcag cattgcgcat cctccatcac tgaaggctag cgtcgcacaa        60

<210> SEQ ID NO 66
<211> LENGTH: 60
<212> TYPE: DNA
<213> ORGANISM: Artificial Sequence
<220> FEATURE:
<223> OTHER INFORMATION: primer

<400> SEQUENCE: 66
ctagttgtgc gacgctagcc ttcagtgatg gaggatgcgc aatgctgcaa tctcacatct        60

<210> SEQ ID NO 67
<211> LENGTH: 60
<212> TYPE: DNA
<213> ORGANISM: Artificial Sequence
<220> FEATURE:
<223> OTHER INFORMATION: primer

<400> SEQUENCE: 67
aattatatgt gatattccac cattgcacat gcttcatcac ggaatgcgag cgtcacacta        60

<210> SEQ ID NO 68
<211> LENGTH: 60
<212> TYPE: DNA
<213> ORGANISM: Artificial Sequence
<220> FEATURE:
<223> OTHER INFORMATION: primer

<400> SEQUENCE: 68
ctagtagtgt gacgctcgca ttccgtgatg aagcatgtgc aatggtggaa tatcacatat        60

<210> SEQ ID NO 69
<211> LENGTH: 60
<212> TYPE: DNA
<213> ORGANISM: Artificial Sequence
<220> FEATURE:
<223> OTHER INFORMATION: primer

<400> SEQUENCE: 69
aattataggt gatagtccac ccttgcactt gcttcctcac ggcatgcgat cgtcactcta        60

<210> SEQ ID NO 70
<211> LENGTH: 60
<212> TYPE: DNA
<213> ORGANISM: Artificial Sequence
<220> FEATURE:
<223> OTHER INFORMATION: primer

<400> SEQUENCE: 70
ctagtagagt gacgatcgca tgccgtgagg aagcaagtgc aagggtggac tatcacctat        60

<210> SEQ ID NO 71
<211> LENGTH: 64
<212> TYPE: DNA
<213> ORGANISM: Artificial Sequence
<220> FEATURE:
<223> OTHER INFORMATION: primer

<400> SEQUENCE: 71
aattcagtcg tgcggagaag acaaagtcag ctgcgtgggt ctcctccggc gccggctctg        60
caag                                                                    64

<210> SEQ ID NO 72
<211> LENGTH: 64

```
<212> TYPE: DNA
<213> ORGANISM: Artificial Sequence
<220> FEATURE:
<223> OTHER INFORMATION: primer

<400> SEQUENCE: 72
ctagcttgca gagccggcgc cggaggagac ccacgcagct gactttgtct tctccgcacg    60
actg                                                                  64

<210> SEQ ID NO 73
<211> LENGTH: 64
<212> TYPE: DNA
<213> ORGANISM: Artificial Sequence
<220> FEATURE:
<223> OTHER INFORMATION: primer

<400> SEQUENCE: 73
aattcagtcg tgcggagatg acaaagtcag ctgggtgggt ctcctccgac gccggctctg    60
caac                                                                  64

<210> SEQ ID NO 74
<211> LENGTH: 64
<212> TYPE: DNA
<213> ORGANISM: Artificial Sequence
<220> FEATURE:
<223> OTHER INFORMATION: primer

<400> SEQUENCE: 74
ctaggttgca gagccggcgt cggaggagac ccacccagct gactttgtca tctccgcacg    60
actg                                                                  64

<210> SEQ ID NO 75
<211> LENGTH: 64
<212> TYPE: DNA
<213> ORGANISM: Artificial Sequence
<220> FEATURE:
<223> OTHER INFORMATION: primer

<400> SEQUENCE: 75
aattcagacg tgcggtgaag acacagtcag cagcgtgggg ctcctcctgc gccggatctg    60
caac                                                                  64

<210> SEQ ID NO 76
<211> LENGTH: 64
<212> TYPE: DNA
<213> ORGANISM: Artificial Sequence
<220> FEATURE:
<223> OTHER INFORMATION: primer

<400> SEQUENCE: 76
ctaggttgca gatccggcgc aggaggagcc ccacgctgct gactgtgtct tcaccgcacg    60
tctg                                                                  64

<210> SEQ ID NO 77
<211> LENGTH: 64
<212> TYPE: DNA
<213> ORGANISM: Artificial Sequence
<220> FEATURE:
<223> OTHER INFORMATION: primer

<400> SEQUENCE: 77
aattcaggcg tacggcgaac acacagtgag cagcgcggga ctcgtcctgc ggcggatcta    60
```

| | |
|---|---|
| caac | 64 |

\<210> SEQ ID NO 78
\<211> LENGTH: 64
\<212> TYPE: DNA
\<213> ORGANISM: Artificial Sequence
\<220> FEATURE:
\<223> OTHER INFORMATION: primer

\<400> SEQUENCE: 78

| | |
|---|---|
| ctaggttgta gatccgccgc aggacgagtc ccgcgctgct cactgtgtgt tcgccgtacg | 60 |
| cctg | 64 |

\<210> SEQ ID NO 79
\<211> LENGTH: 64
\<212> TYPE: DNA
\<213> ORGANISM: Artificial Sequence
\<220> FEATURE:
\<223> OTHER INFORMATION: primer

\<400> SEQUENCE: 79

| | |
|---|---|
| aattccggcc taccgcgtac agacagtgac cagagcgcga cgcgtactgg ggcagatgta | 60 |
| ctac | 64 |

\<210> SEQ ID NO 80
\<211> LENGTH: 64
\<212> TYPE: DNA
\<213> ORGANISM: Artificial Sequence
\<220> FEATURE:
\<223> OTHER INFORMATION: primer

\<400> SEQUENCE: 80

| | |
|---|---|
| ctaggtagta catctgcccc agtacgcgtc gcgctctggt cactgtctgt acgcggtagg | 60 |
| ccgg | 64 |

\<210> SEQ ID NO 81
\<211> LENGTH: 64
\<212> TYPE: DNA
\<213> ORGANISM: Artificial Sequence
\<220> FEATURE:
\<223> OTHER INFORMATION: primer

\<400> SEQUENCE: 81

| | |
|---|---|
| aattccagcc aaccacgttc agccagggac aagaccgcca cgggtagtgg cgcaaatgga | 60 |
| cttc | 64 |

\<210> SEQ ID NO 82
\<211> LENGTH: 64
\<212> TYPE: DNA
\<213> ORGANISM: Artificial Sequence
\<220> FEATURE:
\<223> OTHER INFORMATION: primer

\<400> SEQUENCE: 82

| | |
|---|---|
| ctaggaagtc catttgcgcc actacccgtg gcggtcttgt ccctggctga acgtggttgg | 60 |
| ctgg | 64 |

\<210> SEQ ID NO 83
\<211> LENGTH: 30
\<212> TYPE: DNA
\<213> ORGANISM: Artificial Sequence
\<220> FEATURE:
\<223> OTHER INFORMATION: primer -continued

<400> SEQUENCE: 83
atggacaaga agtactccat tgggctcgat                                    30

<210> SEQ ID NO 84
<211> LENGTH: 27
<212> TYPE: DNA
<213> ORGANISM: Artificial Sequence
<220> FEATURE:
<223> OTHER INFORMATION: primer

<400> SEQUENCE: 84
gattcacacc ttcctcttct tcttggg                                       27

<210> SEQ ID NO 85
<211> LENGTH: 21
<212> TYPE: DNA
<213> ORGANISM: Artificial Sequence
<220> FEATURE:
<223> OTHER INFORMATION: primer

<400> SEQUENCE: 85
ccgggcctcc atggccatca g                                             21

<210> SEQ ID NO 86
<211> LENGTH: 56
<212> TYPE: DNA
<213> ORGANISM: Artificial Sequence
<220> FEATURE:
<223> OTHER INFORMATION: primer

<400> SEQUENCE: 86
catcttcttt tgcgtcgcca gccgagccac atctcgagcc caccatggca tcaatg       56

<210> SEQ ID NO 87
<211> LENGTH: 56
<212> TYPE: DNA
<213> ORGANISM: Artificial Sequence
<220> FEATURE:
<223> OTHER INFORMATION: primer

<400> SEQUENCE: 87
cggctgactg tcgaacagga ggagcagaga gcggtaccca attcgcccta tagtga       56

<210> SEQ ID NO 88
<211> LENGTH: 60
<212> TYPE: DNA
<213> ORGANISM: Artificial Sequence
<220> FEATURE:
<223> OTHER INFORMATION: primer

<400> SEQUENCE: 88
cggatgagtg tagaagaggc ggaacagtga ggcatttatt ttcattgcaa tgatgtctag   60

<210> SEQ ID NO 89
<211> LENGTH: 56
<212> TYPE: DNA
<213> ORGANISM: Artificial Sequence
<220> FEATURE:
<223> OTHER INFORMATION: primer

<400> SEQUENCE: 89
gatcgtctgt tgagtctcca tccgtgccgc attcacacct tcctcttctt cttggg       56

<210> SEQ ID NO 90

```
<211> LENGTH: 60
<212> TYPE: DNA
<213> ORGANISM: Artificial Sequence
<220> FEATURE:
<223> OTHER INFORMATION: primer

<400> SEQUENCE: 90
cagatcagtc tagtagacgc gcaactgtgc ggcatttatt ttcattgcaa tgatgtctag      60

<210> SEQ ID NO 91
<211> LENGTH: 56
<212> TYPE: DNA
<213> ORGANISM: Artificial Sequence
<220> FEATURE:
<223> OTHER INFORMATION: primer

<400> SEQUENCE: 91
gagcgtatgt agagactcga tctgtgtcgc gttcacacct tcctcttctt cttggg         56

<210> SEQ ID NO 92
<211> LENGTH: 25
<212> TYPE: DNA
<213> ORGANISM: Artificial Sequence
<220> FEATURE:
<223> OTHER INFORMATION: primer

<400> SEQUENCE: 92
ccatttcctg gagccatctc tctcc                                            25

<210> SEQ ID NO 93
<211> LENGTH: 25
<212> TYPE: DNA
<213> ORGANISM: Artificial Sequence
<220> FEATURE:
<223> OTHER INFORMATION: primer

<400> SEQUENCE: 93
ctctcctggg cttgccaagg actca                                            25

<210> SEQ ID NO 94
<211> LENGTH: 50
<212> TYPE: RNA
<213> ORGANISM: Homo sapiens

<400> SEQUENCE: 94
acauuugcuu cugacacaac uguguucacu agcaaccuca aacagacacc                 50

<210> SEQ ID NO 95
<211> LENGTH: 50
<212> TYPE: RNA
<213> ORGANISM: Homo sapiens

<400> SEQUENCE: 95
ggugucuguu ugagguugcu agugaacaca guugugucag aagcaaaugu                 50

<210> SEQ ID NO 96
<211> LENGTH: 50
<212> TYPE: RNA
<213> ORGANISM: Homo sapiens

<400> SEQUENCE: 96
gcugucuguu ugagguuacu agugaacaca guucugucag aagcaaaugc                 50

<210> SEQ ID NO 97
<211> LENGTH: 50
```

```
<212> TYPE: RNA
<213> ORGANISM: Homo sapiens

<400> SEQUENCE: 97
gcugucugug ugagguuacu agugaucaca guucugucag acgcaaaugc         50

<210> SEQ ID NO 98
<211> LENGTH: 50
<212> TYPE: RNA
<213> ORGANISM: Homo sapiens

<400> SEQUENCE: 98
gcuguaugug ugauguuacu acugaucacc guucuguaag acgcacaugc         50

<210> SEQ ID NO 99
<211> LENGTH: 50
<212> TYPE: RNA
<213> ORGANISM: Homo sapiens

<400> SEQUENCE: 99
gcuauaucug ucaugcuacg acucaucucc gaucucuaac acggacacgc         50

<210> SEQ ID NO 100
<211> LENGTH: 50
<212> TYPE: RNA
<213> ORGANISM: Homo sapiens

<400> SEQUENCE: 100
gcuagaucag ucuugcaacg ccucaucugc gagcucgaac ucggucacuc         50

<210> SEQ ID NO 101
<211> LENGTH: 56
<212> TYPE: RNA
<213> ORGANISM: Homo sapiens

<400> SEQUENCE: 101
uuuuacaaac cgaaccguga aucuuugcgg uuucucuuuc cagccagcgc cgagcg    56

<210> SEQ ID NO 102
<211> LENGTH: 56
<212> TYPE: RNA
<213> ORGANISM: Homo sapiens

<400> SEQUENCE: 102
cgcucggcgc uggcuggaaa gagaaaccgc aaagauucac gguucgguuu guaaaa    56

<210> SEQ ID NO 103
<211> LENGTH: 56
<212> TYPE: RNA
<213> ORGANISM: Homo sapiens

<400> SEQUENCE: 103
agcucggcgc uggcaggaaa gagaaaccuc aaagauucac ggcucgguuu guaaaa    56

<210> SEQ ID NO 104
<211> LENGTH: 56
<212> TYPE: RNA
<213> ORGANISM: Homo sapiens

<400> SEQUENCE: 104
agcucggagc uggcaggaaa gcgaaaccuc aaagacucac ggcucgguuc guaaaa    56

<210> SEQ ID NO 105
```

```
<211> LENGTH: 56
<212> TYPE: RNA
<213> ORGANISM: Homo sapiens

<400> SEQUENCE: 105
agcugggagc uugcaggaua gcgaauccuc aaugacucaa ggcucgcuuc guacaa        56

<210> SEQ ID NO 106
<211> LENGTH: 56
<212> TYPE: RNA
<213> ORGANISM: Homo sapiens

<400> SEQUENCE: 106
agaugugaga uugcagcauu gcgcauccuc caucacugaa ggcuagcguc gcacaa        56

<210> SEQ ID NO 107
<211> LENGTH: 56
<212> TYPE: RNA
<213> ORGANISM: Homo sapiens

<400> SEQUENCE: 107
auaugugaua uuccaccauu gcacaugcuu caucacggaa ugcgagcguc acacua        56

<210> SEQ ID NO 108
<211> LENGTH: 56
<212> TYPE: RNA
<213> ORGANISM: Homo sapiens

<400> SEQUENCE: 108
auaggugaua guccacccuu gcacuugcuu ccucacggca ugcgaucguc acucua        56

<210> SEQ ID NO 109
<211> LENGTH: 60
<212> TYPE: RNA
<213> ORGANISM: Homo sapiens

<400> SEQUENCE: 109
cagucgugcg gagaagacaa agucagcugc gugggucucc uccggcgccg gcucugcaag    60

<210> SEQ ID NO 110
<211> LENGTH: 60
<212> TYPE: RNA
<213> ORGANISM: Homo sapiens

<400> SEQUENCE: 110
cagucgugcg gagaugacaa agucagcugg gugggucucc uccgacgccg gcucugcaac    60

<210> SEQ ID NO 111
<211> LENGTH: 60
<212> TYPE: RNA
<213> ORGANISM: Homo sapiens

<400> SEQUENCE: 111
cagacgugcg gugaagacac agucagcagc guggggcucc uccugcgccg gaucugcaac    60

<210> SEQ ID NO 112
<211> LENGTH: 60
<212> TYPE: RNA
<213> ORGANISM: Homo sapiens

<400> SEQUENCE: 112
caggcguacg gcgaacacac agugagcagc gcgggacucg uccugcggcg gaucuacaac    60
```

```
<210> SEQ ID NO 113
<211> LENGTH: 60
<212> TYPE: RNA
<213> ORGANISM: Homo sapiens

<400> SEQUENCE: 113
ccggccuacc gcguacagac agugaccaga gcgcgacgcg uacuggggca gauguacuac      60

<210> SEQ ID NO 114
<211> LENGTH: 60
<212> TYPE: RNA
<213> ORGANISM: Homo sapiens

<400> SEQUENCE: 114
ccagccaacc acguucagcc agggacaaga ccgccacggg uaguggcgca aauggacuuc      60

<210> SEQ ID NO 115
<211> LENGTH: 4140
<212> TYPE: DNA
<213> ORGANISM: Homo sapiens

<400> SEQUENCE: 115
atggacaaga agtactccat tgggctcgat atcggcacaa acagcgtcgg ctgggccgtc      60
attacggacg agtacaaggt gccgagcaaa aaattcaaag ttctgggcaa taccgatcgc     120
cacagcataa agaagaacct cattggcgcc ctcctgttcg actccgggga gacggccgaa     180
gccacgcggc tcaaaagaac agcacggcgc agatataccc gcagaaagaa tcggatctgc     240
tacctgcagg agatctttag taatgagatg gctaaggtgg atgactcttt cttccatagg     300
ctggaggagt cctttttggt ggaggaggat aaaaagcacg agcgccaccc aatctttggc     360
aatatcgtgg acgaggtggc gtaccatgaa agtacccaa ccatatatca tctgaggaag     420
aagcttgtag acagtactga taaggctgac ttgcggttga tctatctcgc gctggcgcat     480
atgatcaaat ttcggggaca cttcctcatc gagggggacc tgaacccaga caacagcgat     540
gtcgacaaac tctttatcca actggttcag acttacaatc agcttttcga agagaacccg     600
atcaacgcat ccggagttga cgccaaagca atcctgagcg ctaggctgtc caaatcccgg     660
cggctcgaaa acctcatcgc acagctccct ggggagaaga gaacggcct gtttggtaat     720 cttatcgccc tgtcactcgg gctgaccccc aactttaaat ctaacttcga cctggccgaa     780
gatgccaagc ttcaactgag caaagacacc tacgatgatg atctcgacaa tctgctggcc     840
cagatcggcg accagtacgc agacctttt ttggcggcaa agaacctgtc agacgccatt     900
ctgctgagtg atattctgcg agtgaacacg gagatcacca agctccgct gagcgctagt     960 atgatcaagc gctatgatga gcaccaccaa gacttgactt tgctgaaggc ccttgtcaga    1020
cagcaactgc ctgagaagta caaggaaatt ttcttcgatc agtctaaaaa tggctacgcc    1080
ggatacattg acggcggagc aagccaggag gaattttaca aatttattaa gcccatcttg    1140
gaaaaaatgg acggcaccga ggagctgctg gtaaagctta acagagaaga tctgttgcgc    1200
aaacagcgca cttttcgaca atggaagcat ccccaccaga ttcacctggg cgaactgcac    1260
gctatcctca ggcggcaaga ggatttctac cccttttttga agataacag ggaaaagatt    1320 gagaaaatcc tcacatttcg gataccctac tatgtaggcc cctcgcccg ggaaattcc    1380 agattcgcgt ggatgactcg caaatcagaa gagaccatca ctccctggaa cttcgaggaa    1440
gtcgtggata aggggcctc tgcccagtcc ttcatcgaaa ggatgactaa ctttgataaa    1500
aatctgccta acgaaaaggt gcttcctaaa cactctctgc tgtacgagta cttcacagtt    1560
```

```
tataacgagc tcaccaaggt caaatacgtc acagaaggga tgagaaagcc agcattcctg    1620
tctggagagc agaagaaagc tatcgtggac ctcctcttca agacgaaccg gaaagttacc    1680
gtgaaacagc tcaaagaaga ctatttcaaa aagattgaat gtttcgactc tgttgaaatc    1740
agcggagtgg aggatcgctt caacgcatcc ctgggaacgt atcacgatct cctgaaaatc    1800
attaaagaca aggacttcct ggacaatgag gagaacgagg acattcttga ggacattgtc    1860 ctcacccctta cgttgtttga agataggagag atgattgaag aacgcttgaa aacttacgct    1920
catctcttcg acgacaaagt catgaaacag ctcaagaggc gccgatatac aggatggggg    1980
cggctgtcaa gaaaactgat caatgggatc cgagacaagc agagtggaaa gacaatcctg    2040
gattttctta gtccgatgg atttgccaac cggaacttca tgcagttgat ccatgatgac    2100
tctctcacct ttaaggagga catccagaaa gcacaagttt ctggccaggg ggacagtctt    2160
cacgagcaca tcgctaatct tgcaggtagc ccagctatca aaaagggaat actgcagacc    2220
gttaaggtcg tggatgaact cgtcaaagta atgggaaggc ataagcccga gaatatcgtt    2280
atcgagatgg cccgagagaa ccaaactacc cagaagggac agaagaacag taggagaagg    2340
atgaagagga ttgaagaggg tataaaagaa ctggggtccc aaatccttaa ggaacaccca    2400
gttgaaaaca cccagcttca gaatgagaag ctctacctgt actacctgca gaacggcagg    2460
gacatgtacg tggatcagga actggacatc aatcggctct ccgactacga cgtggatcat    2520
atcgtgcccc agtcttttct caaagatgat tctattgata taaagtgtt gacaagatcc    2580 gataaaaata gagggaagag tgataacgtc ccctcagaag aagttgtcaa gaaaatgaaa    2640
aattattggc ggcagctgct gaacgccaaa ctgatcacac aacggaagtt cgataatctg    2700
actaaggctg aacgaggtgg cctgtctgag ttggataaag ccggcttcat caaaaggcag    2760
cttgttgaga cacgccagat caccaagcac gtggcccaaa ttctcgattc acgcatgaac    2820
accaagtacg atgaaaatga caaactgatt cgagaggtga agttattac tctgaagtct    2880 aagctggtct cagatttcag aaaggacttt cagtttata aggtgagaga gatcaacaat    2940
taccaccatg cgcatgatgc ctacctgaat gcagtggtag gcactgcact tatcaaaaaa    3000
tatcccaagc ttgaatctga atttgtttac ggagactata agtgtacga tgttaggaaa    3060 atgatcgcaa agtctgagca ggaaataggc aaggccaccg ctaagtactt cttttacagc    3120
aatattatga atttttttcaa gaccgagatt acactggcca atggagagat tcggaagcga    3180
ccacttatcg aaacaaacgg agaaacagga gaaatcgtgt gggacaaggg tagggatttc    3240
gcgacagtcc ggaaggtcct gtccatgccg caggtgaaca tcgttaaaaa gaccgaagta    3300
cagaccggag gcttctccaa ggaaagtatc ctcccgaaaa ggaacagcga caagctgatc    3360
gcacgcaaaa aagattggga ccccaagaaa tacggcggat tcgattctcc tacagtcgct    3420
tacagtgtac tggttgtggc caaagtggag aaagggaagt ctaaaaaact caaaagcgtc    3480
aaggaactgc tgggcatcac aatcatggag cgatcaagct tcgaaaaaaa ccccatcgac    3540
tttctcgagg cgaaaggata taagaggtc aaaaaagacc tcatcattaa gcttcccaag    3600
tactctctct ttgagcttga aaacggccgg aaacgaatgc tcgctagtgc gggcgagctg    3660
cagaaaggta cgagctggc actgccctct aaatacgtta atttcttgta tctgccagc    3720 cactatgaaa agctcaaagg gtctcccgaa gataatgagc agaagcagct gttcgtggaa    3780
caacacaaac actaccttga tgagatcatc gagcaaataa gcgaattctc caaaagagtg    3840
atcctcgccg acgctaacct cgataaggtg ctttctgctt acaataagca cagggataag    3900
cccatcaggg agcaggcaga aaacattatc cacttgttta ctctgaccaa cttgggcgcg    3960
```

```
cctgcagcct tcaagtactt cgacaccacc atagacagaa agcggtacac ctctacaaag   4020
gaggtcctgg acgccacact gattcatcag tcaattacgg ggctctatga aacaagaatc   4080
gacctctctc agctcggtgg agacagcagg gctgacccca agaagaagag gaaggtgtga   4140
```

<210> SEQ ID NO 116
<211> LENGTH: 1379
<212> TYPE: PRT
<213> ORGANISM: Homo sapiens

<400> SEQUENCE: 116

| Met | Asp | Lys | Lys | Tyr | Ser | Ile | Gly | Leu | Asp | Ile | Gly | Thr | Asn | Ser | Val |
|---|---|---|---|---|---|---|---|---|---|---|---|---|---|---|---|
| 1 | | | | 5 | | | | | 10 | | | | | 15 | |

Gly Trp Ala Val Ile Thr Asp Glu Tyr Lys Val Pro Ser Lys Lys Phe
                20                  25                  30

Lys Val Leu Gly Asn Thr Asp Arg His Ser Ile Lys Lys Asn Leu Ile
            35                  40                  45

Gly Ala Leu Leu Phe Asp Ser Gly Glu Thr Ala Glu Ala Thr Arg Leu
        50                  55                  60

Lys Arg Thr Ala Arg Arg Arg Tyr Thr Arg Arg Lys Asn Arg Ile Cys
65                  70                  75                  80

Tyr Leu Gln Glu Ile Phe Ser Asn Glu Met Ala Lys Val Asp Asp Ser
                85                  90                  95

Phe Phe His Arg Leu Glu Glu Ser Phe Leu Val Glu Glu Asp Lys Lys
            100                 105                 110

His Glu Arg His Pro Ile Phe Gly Asn Ile Val Asp Glu Val Ala Tyr
        115                 120                 125

His Glu Lys Tyr Pro Thr Ile Tyr His Leu Arg Lys Lys Leu Val Asp
    130                 135                 140

Ser Thr Asp Lys Ala Asp Leu Arg Leu Ile Tyr Leu Ala Leu Ala His
145                 150                 155                 160

Met Ile Lys Phe Arg Gly His Phe Leu Ile Glu Gly Asp Leu Asn Pro
                165                 170                 175

Asp Asn Ser Asp Val Asp Lys Leu Phe Ile Gln Leu Val Gln Thr Tyr
            180                 185                 190

Asn Gln Leu Phe Glu Glu Asn Pro Ile Asn Ala Ser Gly Val Asp Ala
        195                 200                 205

Lys Ala Ile Leu Ser Ala Arg Leu Ser Lys Ser Arg Arg Leu Glu Asn
    210                 215                 220

Leu Ile Ala Gln Leu Pro Gly Glu Lys Lys Asn Gly Leu Phe Gly Asn
225                 230                 235                 240

Leu Ile Ala Leu Ser Leu Gly Leu Thr Pro Asn Phe Lys Ser Asn Phe
                245                 250                 255

Asp Leu Ala Glu Asp Ala Lys Leu Gln Leu Ser Lys Asp Thr Tyr Asp
            260                 265                 270

Asp Asp Leu Asp Asn Leu Leu Ala Gln Ile Gly Asp Gln Tyr Ala Asp
        275                 280                 285

Leu Phe Leu Ala Ala Lys Asn Leu Ser Asp Ala Ile Leu Leu Ser Asp
    290                 295                 300

Ile Leu Arg Val Asn Thr Glu Ile Thr Lys Ala Pro Leu Ser Ala Ser
305                 310                 315                 320

Met Ile Lys Arg Tyr Asp Glu His His Gln Asp Leu Thr Leu Leu Lys
                325                 330                 335

Ala Leu Val Arg Gln Gln Leu Pro Glu Lys Tyr Lys Glu Ile Phe Phe

```
                340             345             350
Asp Gln Ser Lys Asn Gly Tyr Ala Gly Tyr Ile Asp Gly Gly Ala Ser
            355             360             365
Gln Glu Glu Phe Tyr Lys Phe Ile Lys Pro Ile Leu Glu Lys Met Asp
        370             375             380
Gly Thr Glu Glu Leu Leu Val Lys Leu Asn Arg Glu Asp Leu Leu Arg
385             390             395             400
Lys Gln Arg Thr Phe Asp Asn Gly Ser Ile Pro His Gln Ile His Leu
                405             410             415
Gly Glu Leu His Ala Ile Leu Arg Arg Gln Glu Asp Phe Tyr Pro Phe
            420             425             430
Leu Lys Asp Asn Arg Glu Lys Ile Glu Lys Ile Leu Thr Phe Arg Ile
        435             440             445
Pro Tyr Tyr Val Gly Pro Leu Ala Arg Gly Asn Ser Arg Phe Ala Trp
    450             455             460
Met Thr Arg Lys Ser Glu Glu Thr Ile Thr Pro Trp Asn Phe Glu Glu
465             470             475             480
Val Val Asp Lys Gly Ala Ser Ala Gln Ser Phe Ile Glu Arg Met Thr
                485             490             495
Asn Phe Asp Lys Asn Leu Pro Asn Glu Lys Val Leu Pro Lys His Ser
            500             505             510
Leu Leu Tyr Glu Tyr Phe Thr Val Tyr Asn Glu Leu Thr Lys Val Lys
        515             520             525
Tyr Val Thr Glu Gly Met Arg Lys Pro Ala Phe Leu Ser Gly Glu Gln
    530             535             540
Lys Lys Ala Ile Val Asp Leu Leu Phe Lys Thr Asn Arg Lys Val Thr
545             550             555             560
Val Lys Gln Leu Lys Glu Asp Tyr Phe Lys Lys Ile Glu Cys Phe Asp
                565             570             575
Ser Val Glu Ile Ser Gly Val Glu Asp Arg Phe Asn Ala Ser Leu Gly
            580             585             590
Thr Tyr His Asp Leu Leu Lys Ile Ile Lys Asp Lys Asp Phe Leu Asp
        595             600             605
Asn Glu Glu Asn Glu Asp Ile Leu Glu Asp Ile Val Leu Thr Leu Thr
    610             615             620
Leu Phe Glu Asp Arg Glu Met Ile Glu Glu Arg Leu Lys Thr Tyr Ala
625             630             635             640
His Leu Phe Asp Asp Lys Val Met Lys Gln Leu Lys Arg Arg Arg Tyr
                645             650             655
Thr Gly Trp Gly Arg Leu Ser Arg Lys Leu Ile Asn Gly Ile Arg Asp
            660             665             670
Lys Gln Ser Gly Lys Thr Ile Leu Asp Phe Leu Lys Ser Asp Gly Phe
        675             680             685
Ala Asn Arg Asn Phe Met Gln Leu Ile His Asp Asp Ser Leu Thr Phe
    690             695             700
Lys Glu Asp Ile Gln Lys Ala Gln Val Ser Gly Gln Gly Asp Ser Leu
705             710             715             720
His Glu His Ile Ala Asn Leu Ala Gly Ser Pro Ala Ile Lys Lys Gly
                725             730             735
Ile Leu Gln Thr Val Lys Val Val Asp Glu Leu Val Lys Val Met Gly
            740             745             750
Arg His Lys Pro Glu Asn Ile Val Ile Glu Met Ala Arg Glu Asn Gln
        755             760             765
```

-continued

Thr Thr Gln Lys Gly Gln Lys Asn Ser Arg Glu Arg Met Lys Arg Ile
770             775             780

Glu Glu Gly Ile Lys Glu Leu Gly Ser Gln Ile Leu Lys Glu His Pro
785             790             795             800

Val Glu Asn Thr Gln Leu Gln Asn Glu Lys Leu Tyr Leu Tyr Tyr Leu
        805             810             815

Gln Asn Gly Arg Asp Met Tyr Val Asp Gln Glu Leu Asp Ile Asn Arg
    820             825             830

Leu Ser Asp Tyr Asp Val Asp His Ile Val Pro Gln Ser Phe Leu Lys
        835             840             845

Asp Asp Ser Ile Asp Asn Lys Val Leu Thr Arg Ser Asp Lys Asn Arg
850             855             860

Gly Lys Ser Asp Asn Val Pro Ser Glu Val Val Lys Lys Met Lys
865             870             875             880

Asn Tyr Trp Arg Gln Leu Leu Asn Ala Lys Leu Ile Thr Gln Arg Lys
            885             890             895

Phe Asp Asn Leu Thr Lys Ala Glu Arg Gly Gly Leu Ser Glu Leu Asp
            900             905             910

Lys Ala Gly Phe Ile Lys Arg Gln Leu Val Glu Thr Arg Gln Ile Thr
        915             920             925

Lys His Val Ala Gln Ile Leu Asp Ser Arg Met Asn Thr Lys Tyr Asp
930             935             940

Glu Asn Asp Lys Leu Ile Arg Glu Val Lys Val Ile Thr Leu Lys Ser
945             950             955             960

Lys Leu Val Ser Asp Phe Arg Lys Asp Phe Gln Phe Tyr Lys Val Arg
            965             970             975

Glu Ile Asn Asn Tyr His His Ala His Asp Ala Tyr Leu Asn Ala Val
            980             985             990

Val Gly Thr Ala Leu Ile Lys Lys Tyr Pro Lys Leu Glu Ser Glu Phe
        995             1000            1005

Val Tyr Gly Asp Tyr Lys Val Tyr Asp Val Arg Lys Met Ile Ala
        1010            1015            1020

Lys Ser Glu Gln Glu Ile Gly Lys Ala Thr Ala Lys Tyr Phe Phe
    1025            1030            1035

Tyr Ser Asn Ile Met Asn Phe Phe Lys Thr Glu Ile Thr Leu Ala
    1040            1045            1050

Asn Gly Glu Ile Arg Lys Arg Pro Leu Ile Glu Thr Asn Gly Glu
    1055            1060            1065

Thr Gly Glu Ile Val Trp Asp Lys Gly Arg Asp Phe Ala Thr Val
    1070            1075            1080

Arg Lys Val Leu Ser Met Pro Gln Val Asn Ile Val Lys Lys Thr
    1085            1090            1095

Glu Val Gln Thr Gly Gly Phe Ser Lys Glu Ser Ile Leu Pro Lys
    1100            1105            1110

Arg Asn Ser Asp Lys Leu Ile Ala Arg Lys Lys Asp Trp Asp Pro
    1115            1120            1125

Lys Lys Tyr Gly Gly Phe Asp Ser Pro Thr Val Ala Tyr Ser Val
    1130            1135            1140

Leu Val Val Ala Lys Val Glu Lys Gly Lys Ser Lys Lys Leu Lys
    1145            1150            1155

Ser Val Lys Glu Leu Leu Gly Ile Thr Ile Met Glu Arg Ser Ser
    1160            1165            1170

```
Phe Glu Lys Asn Pro Ile Asp Phe Leu Glu Ala Lys       Gly Tyr Lys
    1175            1180                1185

Glu Val Lys Lys Asp Leu Ile Ile Lys Leu Pro Lys       Tyr Ser Leu
    1190            1195                1200

Phe Glu Leu Glu Asn Gly Arg Lys Arg Met Leu Ala       Ser Ala Gly
    1205            1210                1215

Glu Leu Gln Lys Gly Asn Glu Leu Ala Leu Pro Ser       Lys Tyr Val
    1220            1225                1230

Asn Phe Leu Tyr Leu Ala Ser His Tyr Glu Lys Leu       Lys Gly Ser
    1235            1240                1245

Pro Glu Asp Asn Glu Gln Lys Gln Leu Phe Val Glu       Gln His Lys
    1250            1255                1260

His Tyr Leu Asp Glu Ile Ile Glu Gln Ile Ser Glu       Phe Ser Lys
    1265            1270                1275

Arg Val Ile Leu Ala Asp Ala Asn Leu Asp Lys Val       Leu Ser Ala
    1280            1285                1290

Tyr Asn Lys His Arg Asp Lys Pro Ile Arg Glu Gln       Ala Glu Asn
    1295            1300                1305

Ile Ile His Leu Phe Thr Leu Thr Asn Leu Gly Ala       Pro Ala Ala
    1310            1315                1320

Phe Lys Tyr Phe Asp Thr Thr Ile Asp Arg Lys Arg       Tyr Thr Ser
    1325            1330                1335

Thr Lys Glu Val Leu Asp Ala Thr Leu Ile His Gln       Ser Ile Thr
    1340            1345                1350

Gly Leu Tyr Glu Thr Arg Ile Asp Leu Ser Gln Leu       Gly Gly Asp
    1355            1360                1365

Ser Arg Ala Asp Pro Lys Lys Lys Arg Lys Val
    1370            1375

<210> SEQ ID NO 117
<211> LENGTH: 28
<212> TYPE: RNA
<213> ORGANISM: Artificial Sequence
<220> FEATURE:
<223> OTHER INFORMATION: Synthetic

<400> SEQUENCE: 117
gcucucugcu ccuccuguuc gacaguca                                            28

<210> SEQ ID NO 118
<211> LENGTH: 31
<212> TYPE: RNA
<213> ORGANISM: Artificial Sequence
<220> FEATURE:
<223> OTHER INFORMATION: Synthetic

<400> SEQUENCE: 118
cagcaagagc acaagaggaa gagagagacc c                                        31
```